United States Patent
Fontoura et al.

(10) Patent No.: US 7,544,669 B2
(45) Date of Patent: Jun. 9, 2009

(54) POLYNUCLEOTIDE THERAPY

(75) Inventors: Paulo Fontoura, Mountain View, CA (US); Hideki Garren, Palo Alto, CA (US); William H. Robinson, Menlo Park, CA (US); Lawrence Steinman, Stanford, CA (US); Pedro Jose Ruiz, Redwood City, CA (US); Paul J. Utz, Portola Valley, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 481 days.

(21) Appl. No.: 10/302,098

(22) Filed: Nov. 21, 2002

(65) Prior Publication Data

US 2003/0148983 A1    Aug. 7, 2003

Related U.S. Application Data

(60) Provisional application No. 60/332,070, filed on Nov. 21, 2001.

(51) Int. Cl.
    *A61K 31/70*      (2006.01)
    *C12N 5/00*      (2006.01)
    *C12N 15/00*      (2006.01)
    *A61K 48/00*      (2006.01)

(52) U.S. Cl. .................. 514/44; 435/320.1; 435/325; 435/455; 424/93.1; 424/93.2

(58) Field of Classification Search .................. None
See application file for complete search history.

(56) References Cited

U.S. PATENT DOCUMENTS 5,939,400 A * 8/1999 Steinman et al. ............... 514/44
6,884,785 B2 * 4/2005 von Herrath .................. 514/44
7,030,098 B2      4/2006 Steinman et al.

FOREIGN PATENT DOCUMENTS

| WO | WO 86/01540 | 3/1986 |
| WO | WO 97/45144 | 12/1997 |
| WO | WO 97 45144 | 12/1997 |
| WO | WO 97 46253 A | 12/1997 |
| WO | WO 00/53019 A1 | 9/2000 |
| WO | WO 00/78360 | 12/2000 |

OTHER PUBLICATIONS

Qing-Wen et al Zhongguo Mianyixue Zazhi 17(9): 478-481, 2001.*
Chernavosky et al., Genes and Immunity 1:295-307, 2001.*
von Herrath Nature, 435(7039):151-2.2005.*
Chen et al JI 167:4926-4935, 2001.*
Goncalves, Bioessays. 27(5):506-517, 2005.*
Uengst, BMJ, 326:1410-11, 2003.*
Check Nature 422:7, 2003.*
Couzin et al, Science 307:1028, 2005.*
Rosenberg et al, Science 287:1751, 2000.*
Touchette, Nat. Med. 2(1) 7-8, 1996.*
Solvason et al, J Immunol. 81(12):8298-307, 2008.*
Steinman, Science. 305(5681):212-6, 2004.*
Irene Urbanek-Ruiz, et al.; Immunization with DNA Encoding an Immunodominat Peptide of Insulin Prevents Diabetes in NOD Mic; Clinical Immunology; Journal, August, 164-171,vol. 100, No. 2, Aug. 2001; Academic Press; USA.
Pedro J. Ruiz, et al. Suppressive Immunization with DNA Encoding a Self-Peptide Prevents Autoimmune Disease: Modulation of T Cell Costimulation; The Journal of Immunology, Mar. 15, 1999, 162: 3336-3341, USA.
Prud'Homme Gerald J., et al; Immunoinhibitory DNA Vaccine Protects Against Autoimmune Diabetes Through cDNA Encoding A Selective CTLA-4 (CD152) Ligand; Human Gene Therapy, Feb. 10, 2002, 395-406, v 13, No. 3; McGill University, Canada.
Jindal et al., Prevention of Diabetes in the NOD Mouse by Intra-Muscular Injection of Recombinant Adeno-Associated Virus Containing the Preproinsulin II Gene, International Journal of Experimental Diabetes Research, 2001, 2; 129-138.
Rapoport et al., Interleukin 4 Reverses T Cell Proliferative Unresponsiveness and Prevents the Onset of Diabetes in Nonobese Diabetic Mice, J Exp Med, 1993, 178; 87-99.
Wicker et al., Naturally Processed T Cell Epitopes From Human Glutamic Acid Decarboxylase Identified Using Mice Transgenic for the Type 1 Diabetes-Associated Human MHC Class II Allele, DRB1*0401, J Clin Invest, 1996, 98(11); 2597-2603.
Anderton et al., Hierarchy in the Ability of T Cell Epitopes to Induce Peripheral Tolerance to Antigens from Myelin, European Journal of Immunology, (1998), vol. 28:1251-1261.
Barnett et al., Virus Encoding an Encephalitogenic Peptide Protects Mice from Experimental Allergic Encephalomyelitis, Journal of Neuroimmunology, vol. 64:163-173.
Bebo et al., Male SJL Mice do not Relapse After Induction of EAE With PLP 139-151, Journal of Neuroscience Research, vol. 45:680-689.
Brocke, S. et al., Treatment of Experimental Encephalomyelitis with a Peptide Analogue of Myelin Basic Protein, Nature, (1996), 379, 343-6.

(Continued)

*Primary Examiner*—Sumesh Kaushal
(74) *Attorney, Agent, or Firm*—Townsend and Townsend and Crew LLP

(57) ABSTRACT

This invention provides a method of treating or preventing a disease in an animal associated with one or more self-protein(s), -polypeptide(s), or -peptide(s) that is present or involved in a non-physiologic process in the animal comprising administering to the animal a self-vector comprising a polynucleotide encoding the self-protein(s), -polypeptide(s) or -peptide(s) associated with the disease. Administration of the self-vector comprising a polynucleotide encoding the self-protein(s), -polypeptide(s) or -peptide(s) modulates an immune response to the self-protein(s), -polypeptide(s) or -peptide(s) expressed from administration of the self-vector. The invention also provides a composition comprising a polynucleotide encoding one or more self-protein(s), -polypeptide(s), or -peptide(s) that is present non-physiologically in a treated animal useful in treating or preventing a disease associated with the self-protein(s), -polypeptide(s), or -peptide(s) present in and/or the target of a non-physiologic process in the animal.

39 Claims, 10 Drawing Sheets

OTHER PUBLICATIONS

Bu Df et al., Two Human Glutamate Decarboxylases, 65-KDA GAD and 67-KDA GAD, are Each Encoded by a Single Gene, Proc Natl Acad Sci, (1992) USA 89(6): 2115-2119.

Cohen, et al., Exploring the Potential of DNA Vaccination, Hosp. Practice, (1997), pp. 169-177.

Coon et al., DNA Immunization to Prevent Autoimmune Diabetes, J. Clin. Invest, (1999), 104(2):189-94.

Davis, et al., DNA-Based Immunization Induces Continuous Secretion of Hepatitis B Surface Antigen and High Levels of Circulating Antibody, Human Mol. Genetics, (1993), V.11, pp. 1847-1851.

Davis, et al., Direct Gene Transfer in Skeletal Muscle: Plasmid DNA-Based Immunization Against the Hepatitis B Virus Surface Antigen, Vaccine, (1994), V. 12, No. 16, pp. 1503-1509.

Falo, et al., Giving DNA Vaccines a Helping Hand, Nature Medicine, V. 4, No. 11, (1998), pp. 1239-1240.

Garren, H. et al., Combination of Gene Delivery and DNA Vaccination to Protect From and Reverse TH1 Autoimmune Disease Via Deviation to the TH2 Pathway, Immunity, (2001), 15, 15-22.

Greer et al., Identification and Characterization of a Second Encephalitogenic Determinant of Myelin Proteolipid Protein (Residues 178-191) for SJL Mice, J. of Immunology, V. 149, (1992), pp. 783-788.

IFNB_MS_Study_Group, Interferon Beta-1B in the Treatment of Multiple Sclerosis: Final Outcome of the Randomized Controlled Trial, The IFNB Multiple Sclerosis Study Group and The University of British Columbia MS/MRI Analysis Group, (1995), Neurology 45, 1277-85.

Jacobs, Lawrence et al., Extended Observations on MS Patients Treated With IM Interfereon-β LA (Avonex™): Implications for Modern MS Trials and Therapeutics Presented in Part at Pathogenic and Regulatory Cells in Demyelinating Diseases, Rome, Italy, Sep. 12-15, 1999, Journal of Neuroimmunology, (2000), vol. 107, pp. 167-173.

Johnson, K. P et al., R. B. Copolymer 1 Reduces Relapse Rate and Improves Disability in Relapsing- Remitting Multiple Sclerosis: Results of a Phase III Multicenter, Double-Blind Placebo-Controlled Trial. The Copolymer 1 Multiple Sclerosis Study Group, Neurology, (1995), 45, 1268-76.

Kamholz J et al., Identification of Three Forms of Human Myelin Basic Protein by CDNA Cloning, 1986, Proc Natl Acad Sci USA, 83:4962-6.

Kappos et al., Induction of a Non-Encephalitogenic Type 2 T Helper-Cell Autoimmune Response in Multiple Sclerosis After Administration of an Altered Peptide Ligand in a Placebo-Controlled, Randomized Phase II Trial, The Altered Peptide Ligand in Relapsing MS Study Group, (2000), Nat Med 6, 1176-82.

Karin, N. et al., Reversal of Experimental Autoimmune Encephalomyelitis by a Soluble Peptide Variant of a Myelin Basic Protein Epitope: T Cell Receptor Antagonism and Reduction of Interferon Gamma and Tumor Necrosis Factor Alpha Production, (1994), J Exp Med 180, 2227-37.

Kerlero de Rosbo, et al., T-Cell Responses T Myelin Antigens in Multiple Sclerosis; Relevance of the Predominant Autoimmune Reactivity to Myelin Oligodendrocyte Glycoprotein, J. of Autoimmunity, (1998), V. 11, pp. 287-299.

King et al., DNA Vaccines With Single-Chain FV Fused to Fragment C of Tetanus Toxin Induce Protective Immunity Against Lymphoma and Myeloma, Nature Medicine, V. 4, No. 11, (1998), pp. 1281-1286.

Krieg et al., The Role of CPG Dinucleotides in DNA Vaccines, Trends in Microbiology, V. 6, No. 1, (1998), pp. 23-27.

Le et al., Safety, Tolerability and Humoral Immune Responses After Intramuscular Administration of a Malaria DNA Vaccine to Healthy Adult Volunteers, Vaccine 18, (2000), 1893-901.

Leadbetter et al., Experimental Autoimmune Encephalomyelitis Induced With a Combination of Myelin Basic Protein and Myelin Oligodendrocyte Glycoprotein is Ameliorated by Administration of a Single Myelin Basic Protein Peptide, J. of Immunology, (1998), 161, pp. 504-512.

Ledley, FD., Pharmaceutical Approach to Somatic Gene Therapy, Pharmaceutical Research, vol. 13:1595-1613.

Liblau RS et al., TH1 and TH2 CD4+ T Cells in the Pathogenesis of Organ-Specific Autoimmune Diseases, Immunol Today, (1995), Jan;16(1):34-8.

Lisak, R. P. et al., Effect of Treatment With Copolymer 1 (COP-1) on the In Vivo and In Vitro Manifestations of Experimental Allergic Encephalomyelitis, (EAE), J Neurol Sci, (1983), 62: 281-93.

Lobell, A. et al., Presence of CPG DNA and the Local Cytokine Milieu Determine the Efficacy of Suppressive DNA Vaccination in Experimental Autoimmune Encephalomyelitis, The Journal of Immunology, (1999), vol. 163, pp. 4754-4762.

Lobell, A. et al., Vaccination With DNA Encoding an Immunodominant Myelin Basic Protein Peptide Targeted to FC of Immunoglobulin G Suppresses Experimental Autoimmune Encephalomyelitis, J. Exp. Med. (1998), vol. 187-No. 9, pp. 1543-1548.

Mikol, et al., "Structure and Chromosomal Location of the Gene for the Oligodendrocyte-Myelin Glycoprotein", J. Cell Biol., (1990), 111(6 pt 1): 2673-2679.

Miller, A. et al., Orally Administered Myelin Basic Protein in Neonates Primes for Immune Responses and Enhances Experimental Autoimmune Encephalomyelitis in Adult Animals, Eur J Immunol, (1994), 24: 1026-32.

Mor et al., Complexity of the Cytokine and Antibody Response Elicited by Immunizing Mice With Plasmodium Yoelii Circumsporozoite Protein Plasmid DNA, Am. Assoc. of Immunologists, (1995), V. 155, pp. 2039-2046.

Nicholson et al., A T Cell Receptor Antagonist Peptide Induces T Cells That Mediate Bystander Suppression and Prevent Autoimmune Encephalomyelitis Induced With Multiple Myelin Antigens, Proc. Natl. Acad. Sci., V. 94, (1997), pp. 9279-9284.

Nowicka et al., Protective Effect of Naked DNA Immunization in Experimental Autoimmune Encephalitis, Journal, of Neuroimmunology, vol. 90, No. 1, (1998), p. 102, abstract 582 XP001068792 ISSN: 0165-5728.

Offner et al., Vaccination With BV8S2 Protein Amplifies TCR-Specific Regulation and Protection Against Experimental Autoimmune Encephalomyelitis in TCR BV8S2 Transgenic Mice, J. of Immunology, (1998), V. 161, pp. 2178-2186.

Oksenberg et al., The Role of MHC and T-Cell Receptor in Susceptiblity to Multiple Sclerosis, Curr. Opinion in Immunology, (1990), V. 2, pp. 619-621.

Oksenberg et al., Selection for T-Cell Receptor Vβ-Dβ-Jβ Gene Rearrangements With Specificity for a Myelin Basic Protein Peptide I Brain Lesions of Multiple Sclerosis, Nature, V. 362, (1993), pp. 68-70.

Pardoll et al., Exposing the Immunology of Naked DNA Vaccines, Immunity, V. 3, (1995), pp. 165-169.

Rawshaw or Ramshaw et al., DNA Vaccines for the Treatment of Autoimmune Disease, Immunology and Cell Biology, Vol. 75:409-413.

Robinson and Pertmer, DNA Vaccines for Viral Infections: Basic Studies and Applications, Adv Virus Res, (2000), 55: 1-74.

Robinson and Torres, DNA Vaccines, Semin Immunol, (1997), 9: 271-83.

Ruiz et al., Suppressive Immunization With DNA Encoding a Self-Peptide Prevents Autoimmune Disease: Modulation of T Cell Costimulation, Jornal of Immunoloy, vol. 162, No. 6, (1999), p. 3336-3341, XP002196043.

Sato et al., Immunostimulatory DNA Sequences Necessary for Effective Intradermal Gene Immunization, Science, vol. 273-352-354.

Sela, M. et al., Glatiramer Acetate in the Treatment of Multiple Sclerosis, Expert Opin Pharmacother, (2001), 2: 1149-65.

Simons R, et al., Human Myelin DM-20 Proteolipid Protein Deletion Defined by CDNA Sequence, Biochem Biophys Res Commun, (1987), 146(2): 666-671.

Spagnol G, et al., Molecular Cloning of Human Myelin-Associated Glycoprotine, J Neurosci Res, (1989), 24:137-42.

Steinman, The Use of Monoclonal Antibodies for Treatment of Autoimmune Disease, J. Clin. Immunol., (1990), 10(6):30S-38S; discussion 38S-39S.

Syrengelas, et al., DNA Immunization Induces Protective Immunity Against B-Cell Lymphoma, Nature Medicine, V. 2(9), (1996), pp. 1038-1041.

Tang, et al., Genetic Immunization is a Simple Method for Eliciting an Immune Response, Nature, V. 356, (1992), pp. 152-154.

Teitelbaum D. et al., Copolymer 1 Inhibits Chronic Relapsing Experimental Allergic Encephalomyelitis Induced by Proteolipid Protein (PLP) Peptides in Mice and Interferes with PLP-Specific T Cell Responses, J Neuroimmunology, (1995), 64: 209-217.

Timmerman et al., Idiotype-Encoding Recombinant Adenoviruses Provide Protective Immunity Against Murine B-Cell Lymphomas, Blood, (2001), 97:1370-1377.

Tsunoda et al., Enhancement of Experimental Allergic Encephalomyelitis (EAE) by DNA Immunization With Myelin Proteolipid Protein (PLP) Plasmid DNA, Journal of Neuropathology and Experimental Neurology vol. 57(8): 758-767.

Tubridy et al., The Effect of Anti-Alpha4 Integrin Antibody on Brain Lesion Activity in MS, The UK Antegren Study Group, Neurology, (1999), 53: 466-72.

Tuohy VK et al., Modulation of the IL-10/IL-12 Cytokine Circuit by Interferon-Beta Inhibits the Development of Epitope Spreading and Disease Progression in Murine Autoimmune Encephalomyelitis, J Neuroimmunol, (2000), 111,55-63.

Ulmer et al., DNA Vaccines, Current Opinion in Immunology, (1996), vol. 8, pp. 531-536.

Ulmer et al., Heterologous Protection Against Influenza by Injection of DNA Encoding a Viral Protein, Science, V. 259, (1993), pp. 1745-1749.

Urbanek-Ruiz, et al., Immunization With DNA Encoding an Immunodominant Peptide of Insulin Prevents Diabetes in NOD Mice, Clin. Immunol., (2001), 100:164-171.

Van Oosten et al., Treatment of Multiple Sclerosis With the Monoclonal Anti-CD4 Antibody CM-T412: Results of a Randomized, Double-Blind, Placebo-Controlled, MR-Monitored Phase II Trial, Neurology, (1997), 49:351-357.

Waisman et al., Suppressive Vaccination With DNA Encoding a Variable Region Gene of The T-Cell Receptor Prevents Autoimmune Encephalomyelitis and Activates TEH2 Immunity, Nature Medicine, V. 2(8), (1996), pp. 899-905.

Weiner H. L. et al., Oral Tolerance: Immunologic Mechanisms and Treatment of Animal and Human Organ-Specific Autoimmune Diseases by Oral Administration of Autoantigens, Annu Rev Immunol, (1994), 12, 809-37.

Wiest-Ladenburger et al., DNA Vaccination With Glutamic Acid Decarboxylase (GAD) Generates a Strong Humoral Immune Response in BALB/C, C57BL/6, and in Diabetes-Prone NOD Mice, Horm. Metab., (1998), Res., 30(10):605-609.

Wildbaum et al., A Targeted DNA Vaccine Augments the Natural Immune Reponse to Self TNF-Alpha and Suppresses Ongoing Adjuvant Arthritis, Immunol, (2000), 165:5860-5866.

Wildbaum et al., A Targeted DNA Vaccine Encoding FAS Ligand Defines its Dual Role in the Regulation of Experimental Autoimmune Encephalomyelitis. J Clin Invest , (2000), 106:671-679.

Wildbaum et al., Neutralizing Antibodies to IFN-Inducing Factor Prevent Experimental Autoimmune Encephalomyelitis, J Immunol, (1998), 161:6368-7634.

Wlazlo et al., DNA Tumor Vaccines, Arch Immunol Ther, (2001), Exp 49:1-11.

Xu et al., Protection Against Leishmaniasis by Injection of DNA Encoding a Major Surface Glycopretein, GP63 of L. Major, Immunology, V. 84, (1995), pp. 173-176.

Yasuda et al., Interferon Beta Modulates Experimental Autoimmune Encephalomyelitis by Altering the Pattern of Cytokine Secretion, Immunol. Invest. 28:115-126.

Yednock T.A. et al., Prevention of Experimental Autoimmune Encephalomyelitis by Antibodies Against Alpha 4 Beta 1 Integrin, Nature, (1992) 356: 63-6.

Youssef et al., Prevention of Experimental Autoimmune Encephalomyelitis by MIP-1 Alpha and MCP-1 Naked DNA Vaccines, J Autoimmun, (1999), 13:21-9.

Youssef et al., C-C Chemokine-Encoding DNA Vaccines Enhance Breakdown of Tolerance to Their Gene Products and Treat Ongoing Adjuvant Arthritis, J Clin Invest , (2000), 106:361-371.

Yu et al., Interferon-Beta Inhibits Progression of Relapsing-Remitting Experimental Autoimmune Encephalomyelitis, J. Neuroimmunology, (1996), 64: 91-100.

Aharoni, Rina, et al.; "Copolymer 1 induces T cells of the T helper type 2 that crossreact with myelin basic protein and suppress experimental autoimmune encephalomyelitis"; Proc. Natl. Acad. Sci.; Sep. 1997; pp. 10821-10826; vol. 94.

Baker et al ,Gene Therapy 10:844-853, 2003.

Concalves, M.; "A concise peer into the background, initial thoughts, and practices of human gene therapy"; 2005, BioEssays, vol. 27, pp. 506-517.

Crowe, Paul D., et al., "Differential signaling and hierarchical response thresholds induced by an immunodominant peptide of myelin basic protein and an altered peptide ligand in human T cells"; Human Immunology; 1998; pp. 679-689; vol. 59.

Diehl, Hans-Josef, et al.; "Individual exons encode the integral membrane domains of human myelin proteollpid protein", Proc. Natl. Acad. Sci.;1986, pp. 9807-9811, vol. 83.

Elliott E.; "Immune tolerance mediated by recombinant proteolipid prevents experimental autoimmune encephalomyelitis"; 1997, Journal of Neuroimmunology, vol. 79, pp. 1-11.

Ellmerich et al. (2005) High Incidence of Spontaneous Disease in an HLA and TCR Transgenic Multiple Sclerosis Model. J. Immunol. 174: 1938-1946.

Gaur, Amitabh, et al.; "Amelioration of relapsing experimental autoimmune encephalomyelitis with altered myelin basic protein peptides involves different cellular mechanisms", Journal of Neuroimmunology; 1997; pp. 149-158, vol. 74.

Harrison, L.; "The prospect of vaccination to prevent type I diabetes"; 2005, Human Vaccines, vol. 1, pp. 143-150.

Hilton, Adrienne A., et al.; "Characterization of cDNA and genomic clones encoding human myelin oligodendrocyte glycoprotein", J. Neurochemistry; 1995; pp. 309-316, vol. 65.

Karpus W.; "Inhibition of relapsing experimental autoimmune encephalomyelitis in SJL mice by feeding the immunodominant PLP139-151 peptide"; 1996, Journal of Neuroscience Res., vol. 45, pp. 410-423.

Klinman et al. The Journal of Immunology 158: 3635-3639, 1997.

Kuchroo, Vijay K., et al.; "A single TCR Antagonist peptide inhibits experimental allergic encephalomyelitis mediatged by a diverse T cell repertoire"; The Journal of Immunology; 1994; pp. 3326-3336; vol. 153.

Liu, M.; "Immunization of non-human primates with DNA vaccines"; 1997, vol. 15, pp. 909-912.

Martin, Roland, et al.; "Fine Specificity and HLA restrictions of myelin basic protein-specific cytotoxic T cell lines from multiple sclerosis patients and healthy individuals"; The Journal of Immunology; 1990; pp. 540-548; vol. 145.

Meinl, Edgar, et al.; "Myelin basic protein-specific T lymphocyte repertoire in multiple sclerosis —complexity of the response and dominance of nested epitopes due to recruitement of multiple T cell clones"; J. Clin. Invest.; 1993, pp. 2633-2643; vol. 92.

Parekh-Olmeda H.; "Gene therapy progress and prospects: targeted gene repair"; 2005, Gene Therapy, vol. 12, pp. 639-646.

Pham-Dinh, Danielle, et al.; "Characterization and expression of the cDNA coding for the human myelin/oligodendrocyte glycoprotein", J. Neurochemistry; 1994; pp. 2353-2356, vol. 63.

Ristori et al. (2000) Myelin Basic intramolecular spreading without disease progression in a patient with multiple sclerosis J. of Neuroimmunology. 110:240-243.

Sato, Shuzo, et al.; "cDNA cloning and amino acid sequence for human myelin-associated glycoprotein"; Biochemical and Biophysical Research Communications: Sep. 29, 1989; pp. 1473-1480; vol. 163, No. 3.

Sobel et al, Neurochem Res. 19:915-921, 1994.

Smilek, Dawn E., et al.; "A single amino acid change in a myelin basic protein peptide confers the capacity to prevent rather than induce experimental autoimmune encephalomyelitis", Proc. Natl. Acad. Sci.; Nov. 1991; pp. 9633-9637, vol. 88.

Takacs, Katalin, et al.; "The case against epitope spread in experimental allergic encephalomyelitis", Immunological Review; 1998; pp. 101-110; vol. 164.

Takacs, Katalin, et al.; "Relapsing and remitting experimental allergic encephalomyelitis: a focused response to the encephalitogenic peptide rather than epitope spread"; Eur. J. Immunol.; 1997; pp. 2927-2934; vol. 27.

Trotter, John L., et al.; "T cell recognition of myelin proteolipid protein and myelin proteolipid protein peptides in the peripheral blood of multiple sclerosis and control subjects", Journal of Neuroimmunology; 1998; pp. 172-178; vol. 84.

Tuohy, Vincent K., et al.; "The epitope spreading cascade during progression of experimental autoimmune encephalomyelitis and mulitple sclerosis"; Immunological Reviews; 1998; pp. 93-100; vol. 164.

Tuohy, Vincent, et al.; "Spontaneous regression of primary autoreactivity during chronic progression of experimental autoimmune encephalomyelitis and multiple sclerosis"; J. Exp. Med.; Apr. 5, 1999; pp. 1033-1042; vol. 189, No. 7.

Verma, I.M.; "Gene Therapy: Twenty-first century medicine"; 2005, Annu. Rev. Biochem., vol. 74, pp. 711-738.

Wallstrom, Erik, et al.; "Increased reactivity to myelin oligodendrocyte peptides and epitope mapping in HLA DR2(15)+multiple sclerosis", Eur. J. Immunol.; 1996; pp. 3329-3335, vol. 28.

Warren, K. G., et al.; "Tolerance induction to myelin basic protein by intravenous synthetic peptides containing epitope P.sub.85VVHFFKNIVTP.sub.96 in chronic progressive multiple sclerosis"; Journal of Neurological Sciences; 1997; pp. 31-38; vol. 152.

Davis, Heather L., "Plasmid DNA Expression Systems for the Purpose of Immunization," *Curr Opin Biotechnol*. Oct. 1997;8(5) pp. 635-640.

* cited by examiner

POLYNUCLEOTIDE THERAPY

BACKGROUND OF THE INVENTION

1. Field of the Invention

The present invention relates to methods and compositions for treating diseases in a subject associated with one or more self-protein(s), -polypeptide(s) or -peptide(s) that are present in the subject and involved in a non-physiological state. The present invention also relates to methods and compositions for preventing diseases in a subject associated with one or more self-protein(s), -polypeptide(s) or -peptide(s) that are present in the subject and involved in a non-physiological state. The invention further relates to the identification of a self-protein(s), -polypeptide(s) or -peptide(s) present in a non-physiological state and associated with a disease. The invention also relates to the administration of a polynucleotide encoding a self-protein(s), -polypeptide(s) or -peptide(s) present in a non-physiological state and associated with a disease. The invention also relates to modulating an immune response to a self-protein(s), -polypeptide(s) or -peptide(s) present in an animal and involved in a non-physiological state and associated with a disease. The invention is more particularly related to the methods and compositions for treating or preventing autoimmune diseases associated with one or more self-protein(s), -polypeptide(s) or -peptide(s) present in the animal in a non-physiological state such as in multiple sclerosis, rheumatoid arthritis, insulin dependent diabetes mellitus, autoimmune uveitis, primary biliary cirrhosis, myasthenia gravis, Sjogren's syndrome, pemphigus vulgaris, scleroderma, pernicious anemia, systemic lupus erythematosus (SLE) and Grave's disease. The invention is also particularly related to the methods and compositions for treating or preventing neurodegenerative diseases associated with one or more self-protein(s), -polypeptide(s) or -peptide(s) present in the animal in a non-physiological state such as Alzheimer's disease, Parkinson's disease, Huntington's disease, and transmissable spongiform encephalopathy (prion disease with the most common form referred to as Creutzfeldt-Jakob disease). The invention is further particularly related to other diseases associated with one or more self-protein(s), -polypeptide(s) or -peptide(s) present in the animal in a non-physiological state such as osteoarthritis, spinal cord injury, obesity, hypertension, peptic ulcer disease, depression, gout, migraine headaches, hyperlipidemia and coronary artery disease. The invention is further particularly related to disease(s) such as disseminated encephalomyelitis associated with one or more self-proteins(s), -polypeptides arising out of the administration of, for example, smallpox vaccine. The invention is also related to the means and methods for treating or preventing disease associated with self-protein(s), -polypeptide(s), or -peptide(s) that are present in an animal that is in a non-physiological state. The invention is further related to the treatment of animals comprising the administration of a polynucleotide encoding self-protein(s), -polypeptide(s), or -peptide(s) that are present non-physiologically or involved in a non-physiologic process in the animal.

2. Autoimmune Disease and Modulation of the Immune Response

Autoimmune disease is any disease caused by adaptive immunity that becomes misdirected at healthy cells and/or tissues of the body. Autoimmune disease affects 3% of the U.S. population and likely a similar percentage of the industrialized world population. (Jacobson et al., Clin Immunol Immunopathol 84, 223-43, 1997). Autoimmune diseases are characterized by T and B lymphocytes that aberrantly target self-proteins, -polypeptides, -peptides, and/or other self-molecules causing injury and or malfunction of an organ, tissue, or cell-type within the body (for example, pancreas, brain, thyroid or gastrointestinal tract) to cause the clinical manifestations of the disease (Marrack et al., Nat Med 7, 899-905, 2001). Autoimmune diseases include diseases that affect specific tissues as well as diseases that can affect multiple tissues. This may, in part, for some diseases depend on whether the autoimmune responses are directed to an antigen confined to a particular tissue or to an antigen that is widely distributed in the body. The characteristic feature of tissue-specific autoimmunity is the selective targeting of a single tissue or individual cell type. Nevertheless, certain autoimmune diseases that target ubiquitous self-proteins can also affect specific tissues. For example, in polymyositis the autoimmune response targets the ubiquitous protein histidyl-tRNA synthetase, yet the clinical manifestations primarily involved are autoimmune destruction of muscle.

The immune system employs a highly complex mechanism designed to generate responses to protect mammals against a variety of foreign pathogens while at the same time preventing responses against self-antigens. In addition to deciding whether to respond (antigen specificity), the immune system must also choose appropriate effector functions to deal with each pathogen (effector specificity). A cell critical in mediating and regulating these effector functions is the CD4$^+$ T cell. Furthermore, it is the elaboration of specific cytokines from CD4$^+$ T cells that appears to be the major mechanism by which T cells mediate their functions. Thus, characterizing the types of cytokines made by CD4$^+$ T cells as well as how their secretion is controlled is extremely important in understanding how the immune response is regulated.

The characterization of cytokine production from longterm mouse CD4$^+$ T cell clones was first published more than 10 years ago (Mosmann et al., J. Immunol. 136:2348-2357, 1986). In these studies, it was shown that CD4$^+$ T cells produced two distinct patterns of cytokine production, which were designated T helper 1 (Th1) and T helper 2 (Th2). Th1 cells were found to predominantly produce interleukin-2 (IL-2), interferon-γ (IFN-γ) and lymphotoxin (LT), while Th2 clones predominantly produced IL-4, IL-5, IL-6, and IL-13 (Cherwinski et al., J. Exp. Med. 169:1229-1244, 1987). Somewhat later, additional cytokines, IL-9 and IL-10, were isolated from Th2 clones (Van Snick et al:, J. Exp: Med. 169:363-368, 1989) (Fiorentino et al., J. Exp. Med. 170: 2081-2095, 1989). Finally, additional cytokines, such as IL-3, granulocyte macrophage colony-stimulating factor (GM-CSF), and tumor necrosis factor-α (TNF-α) were found to be secreted by both Th1 and Th2 cells.

Autoimmune disease encompasses a wide spectrum of diseases that can affect many different organs and tissues within the body as outlined in the table above. (See e.g. Paul, W. E. (1999) Fundamental Immunology, Fourth Edition, Lippincott-Raven, New York.)

TABLE I

| Primary Organ(s) Targeted | Disease |
| --- | --- |
| thyroid | Hashimoto's Disease |
| thyroid | Primary myxodaema |
| thyroid | Thyrotoxicosis |
| stomach | Pernicious anemia |
| stomach | Atrophic gastritis |
| adrenal glands | Addison's disease |
| pancreatic islets | Insulin dependent diabetes mellitus |
| kidneys | Goodpasture's syndrome |
| neuromuscular junction | Myasthenia gravis |

TABLE I-continued

| Primary Organ(s) Targeted | Disease |
|---|---|
| leydig cells | Male infertility |
| skin | Pemphigus vulgaris |
| skin | Pemphioid |
| eyes | Sympathetic ophthalmia |
| eyes | Phacogenic uveitis |
| brain | Multiple sclerosis |
| red blood cells | Hemolytic anemia |
| platelets | Idiopathic thrombocytopenic purpura |
| white blood cells | Idiopathic leucopenia |
| biliary tree | Primary biliary cirrhosis |
| bowel | Ulcerative colitis |
| arteries | Atherosclerosis |
| salivary and lacrimal glands | Sjogren's syndrome |
| synovial joints | Rheumatoid arthritis |
| muscle | Polymyositis |
| muscle and skin | Dermatomyositis |
| skin | Scleroderma |
| skin, joints, muscle, blood cells | Mixed connective tissue disease |
| clotting factors | Anti-phospholipid disease |
| skin | Discoid lupus erythematosus |
| skin, joints, kidneys, brain, blood cells | Systemic lupus erythematosus (SLE) |

Current therapies for human autoimmune disease, include glucocorticoids, cytotoxic agents, and recently developed biological therapeutics. In general, the management of human systemic autoimmune disease is empirical and unsatisfactory. For the most part, broadly immunosuppressive drugs, such as corticosteroids, are used in a wide variety of severe autoimmune and inflammatory disorders. In addition to corticosteroids, other immunosuppressive agents are used in management of the systemic autoimmune diseases. Cyclophosphamide is an alkylating agent that causes profound depletion of both T- and B-lymphocytes and impairment of cell-mediated immunity. Cyclosporine, tacrolimus, and mycophenolate mofetil are natural products with specific properties of T-lymphocyte suppression, and they have been used to treat SLE, RA and, to a limited extent, in vasculitis and myositis. These drugs are associated with significant renal toxicity. Methotrexate is also used as a "second line" agent in RA, with the goal of reducing disease progression. It is also used in polymyositis and other connective-tissue diseases. Other approaches that have been tried include monoclonal antibodies intended to block the action of cytokines or to deplete lymphocytes. (Fox, D. A. Am. J. Med; 99:82-88 1995). Treatments for multiple sclerosis (MS) include interferon β and copolymer 1, which reduce relapse rate by 20-30% and only have a modest impact on disease progression. MS is also treated with immunosuppressive agents including methylprednisolone, other steroids, methotrexate, cladribine and cyclophosphamide. These immunosuppressive agents have minimal efficacy in treating MS. Current therapy for rheumatoid arthritis (RA) utilizes agents that non-specifically suppress or modulate immune function such as methotrexate, sulfasalazine, hydroxychloroquine, leuflonamide, prednisone, as well as the recently developed TNFα antagonists etanercept and infliximab (Moreland et al., J Rheumatol 28, 1431-52., 2001). Etanercept and infliximab globally block TNFα, making patients more susceptible to death from sepsis, aggravation of chronic mycobacterial infections, and development of demyelinating events.

In the case of organ-specific autoimmunity, a number of different therapeutic approaches have been tried. Soluble protein antigens have been administered systemically to inhibit the subsequent immune response to that antigen. Such therapies include delivery of myelin basic protein, its dominant peptide, or a mixture of myelin proteins to animals with experimental autoimmune encephalomyelitis and humans with multiple sclerosis (Brocke et al., Nature 379, 343-6, 1996; Critchfield et al., Science 263, 1139-43., 1994; Weiner et al., Annu Rev Immunol 12, 809-37, 1994), administration of type II collagen or a mixture of collagen proteins to animals with collagen-induced arthritis and humans with rheumatoid arthritis (Gumanovskaya et al., Immunology 97, 466-73., 1999); (McKown et al., Arthritis Rheum 42, 1204-8., 1999); (Trentham et al., Science 261, 1727-30., 1993), delivery of insulin to animals and humans with autoimmune diabetes (Pozzilli and Gisella Cavallo, Diabetes Metab Res Rev 16, 306-7., 2000), and delivery of S-antigen to animals and humans with autoimmune uveitis (Nussenblatt et al., Am J Ophthalmol 123, 583-92., 1997). A problem associated with this approach is T-cell unresponsiveness induced by systemic injection of antigen.

Another approach is the attempt to design rational therapeutic strategies for the systemic administration of a peptide antigen based on the specific interaction between the T-cell receptors and peptides bound to MHC molecules. One study using the peptide approach in an animal model of diabetes, resulted in the development of antibody production to the peptide (Hurtenbach, U et al. J Exp. Med 177:1499, 1993). Another approach is the administration of T cell receptor (TCR) peptide immunization. See for example (Vandenbark A A et al., Nature 341:541, 1989). Still another approach is the induction of oral tolerance by ingestion of peptide or protein antigens. See for example (Weiner H L, Immmunol Today, 18:335 1997).

Immune responses are currently altered by delivering proteins, polypeptides, or peptides, alone or in combination with adjuvants (immunostimulatory agents). For example, the hepatitis B virus vaccine contains recombinant hepatitis B virus surface antigen, a non-self antigen, formulated in aluminum hydroxide, which serves as an adjuvant. This vaccine induces an immune response against hepatitis B virus surface antigen to protect against infection. An alternative approach involves delivery of an attenuated, replication deficient, and/or non-pathogenic form of a virus or bacterium, each non-self antigens, to elicit a host protective immune response against the pathogen. For example, the oral polio vaccine is composed of a live attenuated virus, a non-self antigen, which infects cells and replicates in the vaccinated individual to induce effective immunity against polio virus, a foreign or non-self antigen, without causing clinical disease. Alternatively, the inactivated polio vaccine contains an inactivated or 'killed' virus that is incapable of infecting or replicating and is administered subcutaneously to induce protective immunity against polio virus.

3. Neurodegenerative Diseases

Neurodegenerative diseases are a broad category of diseases of the central nervous system which are all characterized by a slowly progressive destruction or degeneration of nerve cells (Temlett, Curr Opin Neurol 9, 303-7, 1996); (Dickson, Curr Opin Neurol 14, 423-32, 2001); (Kaye, Neurology 51, S45-52; discussion S65-7, 1998); (Prusiner, Proc Natl Acad Sci U S A 95, 13363-83, 1998); (Cummings et al., Neurology 51, S2-17; discussion S65-7, 1998); (Lin et al., Neuron 24, 499-502, 1999); (Chesebro, Neuron 24, 503-6., 1999); (Ross, Neuron 19, 1147-50., 1997); (Yankner, Neuron 16, 921-32., 1996); (Selkoe, Neuron 6, 487-98., 1991). The degeneration of neurons in the brain or spinal cord leads to devastating permanent clinical symptoms including in some cases profound dementia, abnormal movements, tremor, gait ataxia, or epileptiform activity. Common to nearly all of the neurodegenerative diseases is the progressive dementia which can manifest itself as a complete inability to care for oneself and a total lack of recognition of friends and family.

Another common feature of these diseases is the lack of an effective therapy for any of them. Most of the treatments available today focus on supportive care of the late symptoms and none are directed at the underlying pathophysiologic causes of these diseases. For example, for Parkinson's disease medications are directed at and are usually effective in temporarily controlling the tremor associated with the disease, but no medications are effective in halting the progressive dementia and destruction of neurons within the substantia nigra of the brain (Jankovic, Neurology 55, S2-6, 2000). As another example, in Alzheimer's disease until recently no treatments were available for the progressive dementia that characterizes this disease. Several cholinesterase inhibitors have now been approved for use in Alzheimer's disease (Farlow and Evans, Neurology 51, S36-44; discussion S65-7, 1998) (Hake, Cleve Clin J Med 68, 608-9, 613-4, 616, 2001). These drugs presumably increase the amount of the neurotransmitter acetylcholine available in the brain, leading to improved function of those particular neurons that use acetylcholine as a transmitter. All of these drugs, as a whole, show only miniscule efficacy in clinical trials with the primary endpoint being improvement in cognitive testing. These drugs are also not directed at the primary pathophysiology of Alzheimer's disease, namely the destruction of the cholinergic neurons within the brain. Therefore, no current therapy aimed at the primary pathologic cause exists for any of the neurodegenerative diseases.

The majority of neurodegenerative disease also have in common the finding of aggregated or accumulated substances within the areas of the central nervous system that are most affected by the degenerative process. These abnormal accumulations, that can be found either extra- or intra-cellularly, may contribute to the death and destruction of the relevant neurons. Furthermore, the features and composition of the accumulations are specific for a particular disease. For example, the aggregates in Alzheimer's disease consist of a protein called amyloid beta (Aβ), whereas for Parkinson's disease they are composed of a protein called alpha-synuclein (Dickson, Curr Opin Neurol 14:423-432, 2001); (Cummings et al., Neurology 51, S2-17; discussion S65-7, 1998). The neurodegenerative diseases characterized by the development and accumulation of such aggregates include Alzheimer's disease, Parkinson's disease, Huntington's disease, and prion disease (Yankner, Neuron 16:921-32, 1996); (Ross, Neuron 19:1147-50, 1997) (Chesebro, Neuron 24:503-506, 1999); (Dickson, Curr Opin Neurol 14:423-32, 2001).

4. Polynucleotide Therapy

Gene Therapy. Polynucleotide therapeutics, including naked DNA encoding peptides and/or polypeptides, DNA formulated in precipitation- and transfection-facilitating agents, and viral vectors have been used for "gene therapy." Gene therapy is the delivery of a polynucleotide to provide expression of a protein or peptide, to replace a defective or absent protein or peptide in the host and/or to augment a desired physiologic function. Gene therapy includes methods that result in the integration of DNA into the genome of an individual for therapeutic purposes. Examples of gene therapy include the delivery of DNA encoding clotting factors for hemophilia, adenosine deaminase for severe combined immunodeficiency, low-density lipoprotein receptor for familial hypercholesterolemia, glucocerebrosidase for Gaucher's disease, $\alpha_1$-antitrypsin for $\alpha_1$-antitrypsin deficiency, α- or β-globin genes for hemoglobinopathies, and chloride channels for cystic fibrosis (Verma and Somia, Nature 389, 239-42, 1997).

DNA immunization to treat infection. In DNA immunization a non-replicating transcription unit can provide the template for the synthesis of proteins or protein segments that induce or provide specific immune responses in the host. Injection of naked DNA promotes vaccination against a variety of microbes and tumors (Robinson and Torres, Semin Immunol 9, 271-83., 1997). DNA vaccines encoding specific proteins, present in viruses (hepatitis B virus, human immunodeficiency virus, rotavirus, and influenza virus), bacteria (*mycobacterium tuberculosis*), and parasites (Malaria), all non-self antigens, are being developed to prevent and treat these infections (Le et al., Vaccine 18, 1893-901., 2000); (Robinson and Pertmer, Adv Virus Res 55, 1-74, 2000).

DNA to treat neoplasia. DNA vaccines encoding major histocompatibility antigen class I, cytokines (IL-2, IL-12 and IFN-γ), and tumor antigens are being developed to treat neoplasia (Wlazlo and Ertl, Arch Immunol Ther Exp 49:1-11, 2001). For example, viral DNA encoding the B cell immunoglobulin idiotype (antigen binding region) has been administered to eliminate and protect against B cell-lymphomas (Timmerman et al., Blood 97:1370-1377, 2001).

DNA immunization to treat autoimmune disease. Others have described DNA therapies encoding immune molecules to treat autoimmune diseases. Such DNA therapies include DNA encoding the antigen-binding regions of the T cell receptor to alter levels of autoreactive T cells driving the autoimmune response (Waisman et al., Nat Med 2:899-905, 1996) (U.S. Pat. No. 5,939,400). DNA encoding autoantigens were attached to particles and delivered by gene gun to the skin to prevent multiple sclerosis and collagen induced arthritis. (Patent WO 97/46253; Ramshaw et al. Immunol. and Cell Bio. 75:409-413, 1997). DNA encoding adhesion molecules, cytokines (TNFα), chemokines (C-C chemokines), and other immune molecules (Fas-ligand) have been used in animal models of autoimmune disease (Youssef et al., J Clin Invest 106:361-371, 2000); (Wildbaum et al., J Clin Invest 106:671-679, 2000); (Wildbaum et al, J Immunol 165:5860-5866, 2000); (Wildbaum et al., J Immunol 161:6368-7634, 1998); (Youssef et al., J Autoimmun 13:21-9, 1999).

It is an object of the present invention to provide a method of treating or preventing a disease associated with self-protein(s), -polypeptide(s), or -peptide(s) that are present and involved in a non-physiological process in an animal. Another object of this invention is to provide a specific method for treating or preventing autoimmune diseases that does not impair the immune system generally. Still another object of the present invention is to provide a specific method for treating or preventing neurodegenerative diseases. Yet another object of the present invention is to provide a composition for treating or preventing a disease associated with self-protein(s), -polypeptide(s), or -peptide(s) that is present non-physiologically in an animal. Still another object of this invention is to identify self-protein(s), -polypeptide(s), or -peptide(s) that are present non-physiologically and associated with a disease. These and other objects of this invention will be apparent from the specification as a whole.

SUMMARY OF THE INVENTION

Objects of the present invention are accomplished by a novel method of treating or preventing a disease in an animal associated with one or more self-protein(s), -polypeptide(s), or -peptide(s) that is present in the animal nonphysiologically, comprising administering to the animal a self-vector comprising a polynucleotide encoding the self-protein(s), -polypeptide(s) or -peptide(s) associated with the disease. Administration of the self-vector comprising a polynucleotide encoding the self-protein(s), -polypeptide(s) or -peptide(s) modulates an immune response to the self-protein(s), -polypeptide(s) or -peptide(s) that is expressed by the self-vector. A composition comprising a polynucleotide encoding one or more self-protein(s), -polypeptide(s), or -peptide(s) that is present non-physiologically in a treated animal is useful in treating a disease associated with the self-protein(s), -polypeptide(s), or -peptide(s) present in and/or the target of a non-physiologic process in the animal. It was the discovery of this invention that administration of a polynucleotide encoding a self-protein(s), -polypeptide(s), or -peptide(s) that is present non-physiologically or targeted by a non-physiologic process modulates an immune response to the self-protein(s), -polypeptide(s), or -peptide(s) to treat the disease associated with the self-protein(s), -polypeptide(s), or peptide(s) involved non-physiologically in the animal.

In one aspect of the invention there is provided a method for treating or preventing autoimmune diseases such as multiple sclerosis, rheumatoid arthritis, insulin dependent diabetes mellitus, autoimmune uveitis, primary biliary cirrhosis, myasthenia gravis, Sjogren's syndrome, pemphigus vulgaris, scleroderma, pernicious anemia, systemic lupus erythematosus (SLE) and Grave's disease comprising administering to the animal a self-vector comprising a polynucleotide encoding a self-protein(s), -polypeptide(s) or -peptide(s) associated with the autoimmune disease. Administration of the self-vector comprising a polynucleotide encoding the self-protein(s), -polypeptide(s), or -peptide(s) modulates an immune response to the self-protein(s), -polypeptide(s) or -peptide(s) expressed by the self-vector. In one aspect of the invention the route of administration of self-vector comprising a polynucleotide encoding a self-protein(s), -polypeptide(s) or -peptide(s) for prevention of an autoimmune disease is other than particle mediated gene gun delivery to the skin.

In one aspect of the invention there is provided a method for treating neurodegenerative diseases such as Alzheimer's disease, Parkinson's disease, Huntington's disease, and transmissable spongiform encephalopathy (prion disease with the most common form referred to as Creutzfeldt-Jakob disease) comprising administering to the animal a self-vector comprising a polynucleotide encoding a self-protein(s), -polypeptide(s) or -peptide(s) associated with the neurodegenerative disease. Administration of the self-vector comprising a polynucleotide encoding the self-protein(s), -polypeptide(s) or -peptide(s) modulates an immune response to the self-protein(s), -polypeptide(s) or -peptide(s) expressed by the self-vector.

This invention also provides the means and methods for identification of self-protein(s), -polypeptide(s) or -peptide(s) associated with a disease and for modulating an immune response to the self-protein(s), -polypeptide(s) or -peptide(s).

The invention also provides the means and methods for diagnosing and monitoring disease associated with self-protein(s), -polypeptide(s), or -peptide(s) that are present non-physiologically in an animal.

The invention also provides the means and methods for monitoring therapy comprising the administration of a polynucleotide encoding self-protein(s), -polypeptide(s), or -peptide(s) that are present non-physiologically in the animal.

DETAILED DESCRIPTION OF THE INVENTION

Figure 1A:
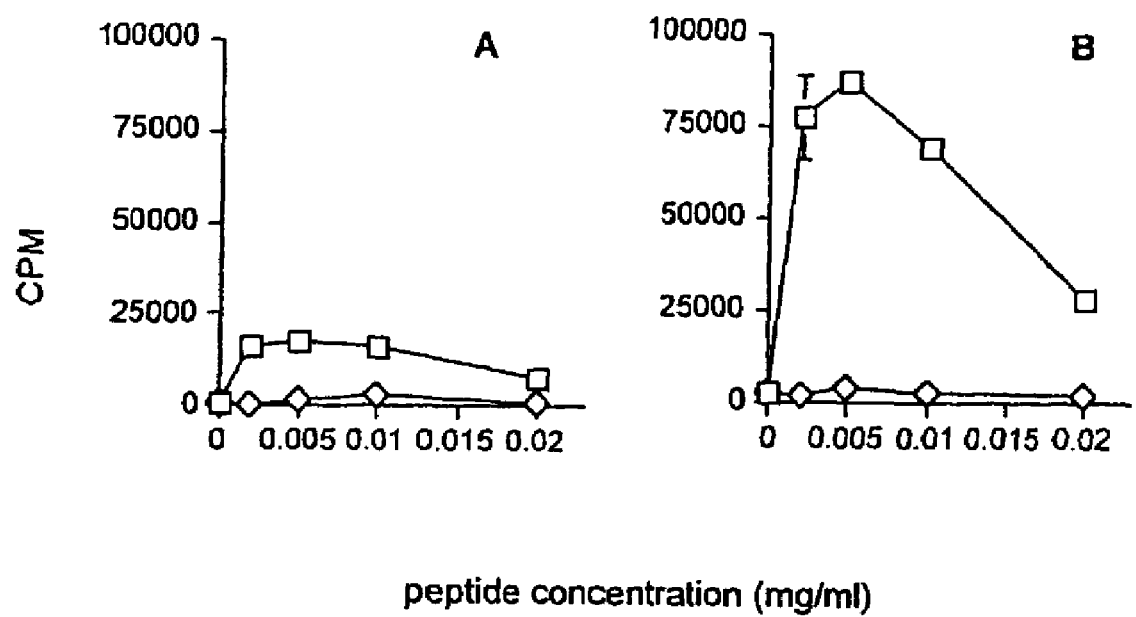
FIG. 1A. DNA encoding a peptide from the self-protein proteolipid protein (PLP) reduces T cell proliferative responses. Lymph node cell (LNC) proliferative responses to PLP139-151 were reduced in DNA vaccinated mice. After recovery from the acute phase of disease animals injected either with DNA coding for PLP139-151 (A) or control vector, pTarget (B) were sacrified and, draining LNC were isolated. Cells were tested in vitro by stimulation with different concentrations of the peptide PLP139-151 (squares) or the control peptide PLP178-191(triangles). Proliferative responses from pooled LNC of groups of five animals are shown as mean CPM±SD of triplicate wells. CPM of Concanavalin A (0.001 mg/ml) stimulated LNC were 102401 for group A and 76702 for group B.

In order that the invention described herein may be more fully understood, the following description is set forth.

The present invention provides a method of treating or preventing a disease in an animal associated with one or more self-protein(s), -polypeptide(s) or -peptide(s) present in the animal non-physiologically or involved in a non-physiologic state comprising administering to the animal a self-vector comprising a polynucleotide encoding the self-protein(s), -polypeptide(s) or -peptide(s) associated with the disease. Administration of the self-vector comprising a polynucleotide encoding the self-protein(s), -polypeptide(s) or -peptide(s) modulates an immune response to the self-protein(s), -polypeptide(s) or -peptide(s) expressed from the self-vector.

The method of treatment or prevention of this invention can be used for any disease associated with a self-protein(s), -polypeptide(s) or -peptide(s) that is present non-physiologically and/or involved in a non-physiologic process within the animal.

Autoimmune Diseases

Several examples of autoimmune diseases associated with self-protein(s), -polypeptide(s) or -peptide(s) present in the animal non-physiologically is set forth in the table below and is described below.

TABLE 2

| Autoimmune Disease | Tissue Targeted | Self-Protein(s) Associated With An Autoimmune Disease |
|---|---|---|
| Multiple sclerosis | central nervous system | myelin basic protein, proteolipid protein, myelin associated glycoprotein, cyclic nucleotide phosphodiesterase, myelin-associated glycoprotein, myelin-associated oligodendrocytic basic protein, myelin oligodendrocyte glycoprotein, alpha-B-crystalin |
| Guillian Barre Syndrome | peripheral nerv. sys. | peripheral myelin protein I and others |
| Insulin Dependent Diabetes Mellitus | β cells in islets of pancreas | tyrosine phosphatase IA2, IA-2β; glutamic acid decarboxylase (65 and 67 kDa forms), carboxypeptidase H, insulin, proinsulin, pre-proinsulin, heat shock proteins, glima 38, islet cell antigen 69 KDa, p52, , islet cell glucose transporter GLUT-2 |
| Rheumatoid Arthritis | synovial joints | Immunoglobulin, fibrin, filaggrin, type I, II, III, IV, V, IX, and XI collagens, GP-39, hnRNPs |
| Autoimmune Uveitis | eye, uvea | S-antigen, interphotoreceptor retinoid binding protein (IRBP), rhodopsin, recoverin |
| Primary Biliary Cirrhosis | biliary tree of liver | pyruvate dehydrogenase complexes (2-oxoacid dehydrogenase) |
| Autoimmune Hepatitis | Liver | Hepatocyte antigens, cytochrome P450 |
| Pemphigus vulgaris | Skin | Desmoglein-1, -3, and others |
| Myasthenia Gravis | nerve-muscle junct. | acetylcholine receptor |
| Autoimmune gastritis | stomach/parietal cells | $H^+/K^+$ ATPase, intrinsic factor |
| Pernicious Anemia | Stomach | intrinsic factor |
| Polymyositis | Muscle | histidyl tRNA synthetase, other synthetases, other nuclear antigens |
| Autoimmune Thyroiditis | Thyroid | Thyroglobulin, thyroid peroxidase |
| Graves's Disease | Thyroid | Thyroid-stimulating hormone receptor |
| Psoriasis | Skin | Unknown |
| Vitiligo | Skin | Tyrosinase, tyrosinase-related protein-2 |
| Systemic Lupus Eryth. | Systemic | nuclear antigens: DNA, histones, ribonucleoproteins |
| Celiac Disease | Small bowel | Transglutaminase |

Multiple Sclerosis Multiple sclerosis (MS) is the most common demyelinating disorder of the CNS and affects 350,000 Americans and one million people worldwide. Onset of symptoms typically occurs between 20 and 40 years of age and manifests as an acute or sub-acute attack of unilateral visual impairment, muscle weakness, paresthesias, ataxia, vertigo, urinary incontinence, dysarthria, or mental disturbance (in order of decreasing frequency). Such symptoms result from focal lesions of demyelination which cause both negative conduction abnormalities due to slowed axonal conduction, and positive conduction abnormalities due to ectopic impulse generation (e.g. Lhermitte's symptom). Diagnosis of MS is based upon a history including at least two distinct attacks of neurologic dysfunction that are separated in time, produce objective clinical evidence of neurologic dysfunction, and involve separate areas of the CNS white matter. Laboratory studies providing additional objective evidence supporting the diagnosis of MS include magnetic resonance imaging (MRI) of CNS white matter lesions, cerebral spinal fluid (CSF) oligoclonal banding of IgG, and abnormal evoked responses. Although most patients experience a gradually progressive relapsing remitting disease course, the clinical course of MS varies greatly between individuals and can range from being limited to several mild attacks over a lifetime to fulminant chronic progressive disease. A quantitative increase in myelin-autoreactive T cells with the capacity to secrete IFN-gamma is associated with the pathogenesis of MS and EAE.

The self-protein, -polypeptide or -peptide targets of the autoimmune response in autoimmune demyelinating diseases, such as multiple sclerosis and experimental autoimmune encephalomyelitis (EAE), may comprise epitopes from proteolipid protein (PLP); myelin basic protein (MBP); myelin oligodendrocyte glycoprotein (MOG); cyclic nucleotide phosphodiesterase (CNPase); myelin-associated glycoprotein (MAG), and myelin-associated oligodendrocytic basic protein (MBOP); alpha-B-crystalin (a heat shock protein); viral and bacterial mimicry peptides, e.g. influenza, herpes viruses, hepatitis B virus, etc.; OSP (oligodendrocyte specific-protein); citrulline-modified MBP (the C8 isoform of MBP in which 6 arginines have been de-imminated to citrulline); etc. The integral membrane protein PLP is a dominant autoantigen of myelin. Determinants of PLP antigenicity have been identified in several mouse strains, and include residues 139-151, 103-116, 215-232, 43-64 and 178-191. At least 26 MBP epitopes have been reported (Meinl et al., J Clin Invest 92, 2633-43, 1993). Notable are residues 1-11, 59-76 and 87-99. Immunodominant MOG epitopes that have been identified in several mouse strains include residues 1-22, 35-55, 64-96. As used herein the term "epitope" is understood to mean a portion of a self-protein, -polypeptide, or -peptide having a particular shape or structure that is recognized by either B-cells or T-cells of the animal's immune system.

In human MS patients the following myelin proteins and epitopes were identified as targets of the autoimmune T and B cell response. Antibody eluted from MS brain plaques recognized myelin basic protein (MBP) peptide 83-97 (Wucherpfennig et al., J Clin Invest 100:1114-1122, 1997). Another study found approximately 50% of MS patients having peripheral blood lymphocyte (PBL) T cell reactivity against myelin oligodendrocyte glycoprotein (MOG) (6-10% control), 20% reactive against MBP (8-12% control), 8% reactive against PLP (0% control), 0% reactive MAG (0% control). In this study 7 of 10 MOG reactive patients had T cell proliferative responses focused on one of 3 peptide epitopes, including MOG 1-22, MOG 34-56, MOG 64-96 (Kerlero de Rosbo et al., Eur J Immunol 27, 3059-69, 1997). T and B cell (brain lesion-eluted Ab) response focused on MBP 87-99 (Oksenberg et al., Nature 362, 68-70, 1993). In MBP 87-99, the amino acid motif HFFK (SEQ ID NO:6) is a dominant target of both the T and B cell response (Wucherpfennig et al., J Clin Invest 100, 1114-22, 1997). Another study observed lymphocyte reactivity against myelin-associated oligodendrocytic basic protein (MOBP), including residues MOBP 21-39 and MOBP 37-60 (Holz et al., J Immunol 164, 1103-9, 2000). Using immunogold conjugates of MOG and MBP peptides to stain MS and control brains both MBP and MOG peptides were recognized by MS plaque-bound Abs (Genain and Hauser, Methods 10, 420-34, 1996).

Rheumatoid Arthritis Rheumatoid arthritis (RA) is a chronic autoimmune inflammatory synovitis affecting 0.8% of the world population. It is characterized by chronic inflammatory synovitis that causes erosive joint destruction. RA is mediated by T cells, B cells and macrophages.

Evidence that T cells play a critical role in RA includes the (1) predominance of CD4+ T cells infiltrating the synovium, (2) clinical improvement associated with suppression of T cell function with drugs such as cyclosporine, and (3) the association of RA with certain HLA-DR alleles. The HLA-DR alleles associated with RA contain a similar sequence of amino acids at positions 67-74 in the third hypervariable region of the β chain that are involved in peptide binding and presentation to T cells. RA is mediated by autoreactive T cells that recognize a self-protein, or modified self-protein, present in synovial joints. Self-protein(s), -polypeptide(s) or -peptides of this invention also referred to as autoantigens are targeted in RA and comprise epitopes from type II collagen; hnRNP; A2/RA33; Sa; filaggrin; keratin; citrulline; cartilage proteins including gp39; collagens type I, III, IV, V, IX, XI; HSP-65/60; IgM (rheumatoid factor); RNA polymerase; hnRNP-B1; hnRNP-D; cardiolipin; aldolase A; citrulline-modified filaggrin and fibrin. Autoantibodies that recognize filaggrin peptides containing a modified arginine residue (deiminated to form citrulline) have been identified in the serum of a high proportion of RA patients. Autoreactive T and B cell responses are both directed against the same immunodominant type II collagen (CII) peptide 257-270 in some patients.

Insulin Dependent Diabetes Mellitus Human type I or insulin-dependent diabetes mellitus (IDDM) is characterized by autoimmune destruction of the β cells in the pancreatic islets of Langerhans. The depletion of β cells results in an inability to regulate levels of glucose in the blood. Overt diabetes occurs when the level of glucose in the blood rises above a specific level, usually about 250 mg/dl. In humans a long presymptomatic period precedes the onset of diabetes. During this period there is a gradual loss of pancreatic beta cell function. The development of disease is implicated by the presence of autoantibodies against insulin, glutamic acid decarboxylase, and the tyrosine phosphatase IA2 (IA2), each an example of a self-protein, -polypeptide or -peptide according to this invention.

Markers that may be evaluated during the presymptomatic stage are the presence of insulitis in the pancreas, the level and frequency of islet cell antibodies, islet cell surface antibodies, aberrant expression of Class II MHC molecules on pancreatic beta cells, glucose concentration in the blood, and the plasma concentration of insulin. An increase in the number of T lymphocytes in the pancreas, islet cell antibodies and blood glucose is indicative of the disease, as is a decrease in insulin concentration.

The Non-Obese Diabetic (NOD) mouse is an animal model with many clinical, immunological, and histopathological features in common with human IDDM. NOD mice spontaneously develop inflammation of the islets and destruction of the β cells, which leads to hyperglycemia and overt diabetes. Both $CD4^+$ and $CD8^+$ T cells are required for diabetes to develop, although the roles of each remain unclear. It has been shown that administration of insulin or GAD, as proteins, under tolerizing conditions to NOD mice prevents disease and down-regulates responses to the other self-antigens.

The presence of combinations of autoantibodies with various specificities in serum are highly sensitive and specific for human type I diabetes mellitus. For example, the presence of autoantibodies against GAD and/or IA-2 is approximately 98% sensitive and 99% specific for identifying type I diabetes mellitus from control serum. In non-diabetic first degree relatives of type I diabetes patients, the presence of autoantibodies specific for two of the three autoantigens including GAD, insulin and IA-2 conveys a positive predictive value of >90% for development of type I DM within 5 years.

Autoantigens targeted in human insulin dependent diabetes mellitus may include the self-protein(s), -polypeptide(s) or -peptide(s) tyrosine phosphatase IA-2; IA-2β; glutamic acid decarboxylase (GAD) both the 65 kDa and 67 kDa forms; carboxypeptidase H; insulin; proinsulin; heat shock proteins (HSP); glima 38; islet cell antigen 69 KDa (ICA69); p52; two ganglioside antigens (GT3 and GM2-1); and an islet cell glucose transporter (GLUT 2).

Human IDDM is currently treated by monitoring blood glucose levels to guide injection, or pump-based delivery, of recombinant insulin. Diet and exercise regimens contribute to achieving adequate blood glucose control.

Autoimmune Uveitis Autoimmune uveitis is an autoimmune disease of the eye that is estimated to affect 400,000 people, with an incidence of 43,000 new cases per year in the U.S. Autoimmune uveitis is currently treated with steroids, immunosuppressive agents such as methotrexate and cyclosporin, intravenous immunoglobulin, and TNFα-antagonists.

Experimental autoimmune uveitis (EAU) is a T cell-mediated autoimmune disease that targets neural retina, uvea, and related tissues in the eye. EAU shares many clinical and immunological features with human autoimmune uveitis, and is induced by peripheral administration of uveitogenic peptide emulsified in Complete Freund's Adjuvant (CFA).

Self-proteins targeted by the autoimmune response in human autoimmune uveitis may include S-antigen, interphotoreceptor retinoid binding protein (IRBP), rhodopsin, and recoverin.

Primary Billiary Cirrhosis Primary Biliary Cirrhosis (PBC) is an organ-specific autoimmune disease that predominantly affects women between 40-60 years of age. The prevalence reported among this group approaches 1 per 1,000. PBC is characterized by progressive destruction of intrahepatic biliary epithelial cells (IBEC) lining the small intrahepatic bile ducts. This leads to obstruction and interference with bile secretion, causing eventual cirrhosis. Association with other autoimmune diseases characterized by epithelium lining/secretory system damage has been reported, including Sjogren's Syndrome, CREST Syndrome, Autoimmune Thyroid Disease and Rheumatoid Arthritis. Attention regarding the driving antigen(s) has focused on the mitochondria for over 50 years, leading to the discovery of the antimitochondrial antibody (AMA) (Gershwin et al., Immunol Rev 174: 210-225, 2000); (Mackay et al., Immunol Rev 174:226-237, 2000). AMA soon became a cornerstone for laboratory diagnosis of PBC, present in serum of 90-95% patients long before clinical symptoms appear. Autoantigenic reactivities in the mitochondria were designated as M1 and M2. M2 reactivity is directed against a family of components of 48-74 kDa. M2 represents multiple autoantigenic subunits of enzymes of the 2-oxoacid dehydrogenase complex (2-OADC) and is another example of the self-protein, -polypeptide, or -peptide of the instant invention. Studies identifying the role of pyruvate dehydrogenase complex (PDC) antigens in the etiopathogenesis of PBC support the concept that PDC plays a central role in the induction of the disease (Gershwin et al., Immunol Rev 174:210-225, 2000); (Mackay et al., Immunol Rev 174:226-237, 2000). The most frequent reactivity in 95% of cases of PBC is the E2 74 kDa subunit, belonging to the PDC-E2. There exist related but distinct complexes including: 2-oxoglutarate dehydrogenase complex (OGDC) and branched-chain (BC) 2-OADC. Three constituent enzymes (E1,2,3) contribute to the catalytic function which is to transform the 2-oxoacid substrate to acyl co-enzyme A (CoA), with reduction of $NAD^+$ to NADH. Mammalian PDC contains an additional component, termed protein X or E-3 Binding protein (E3BP). In PBC patients; the major antigenic response is directed against PDC-E2 and E3BP. The E2 polypeptide contains two tandemly repeated lipoyl domains, while E3BP has a single lipoyl domain. The lipoyl domain is found in a number of autoantigen targets of PBC and is referred to herein as the "PBC lipoyl domain." PBC is treated with glucocorticoids and immunosuppressive agents including methotrexate and cyclosporin A.

A murine model of experimental autoimmune cholangitis (EAC) uses intraperitoneal (i.p.) sensitization with mammalian PDC in female SJL/J mice, inducing non-suppurative destructive cholangitis (NSDC) and production of AMA (Jones, J Clin Pathol 53:813-21, 2000).

Other Autoimmune Diseases And Associated Self-Protein(s), -Polypeptide(s) Or -Peptide(s). Autoantigens for myasthenia gravis may include epitopes within the acetylcholine receptor. Autoantigens targeted in pemphigus vulgaris may include desmoglein-3. Sjogren's syndrome antigens may include SSA (Ro); SSB (La); and fodrin. The dominant autoantigen for pemphigus vulgaris may include desmoglein-3. Panels for myositis may include tRNA synthetases (e.g., threonyl, histidyl, alanyl, isoleucyl, and glycyl); Ku; Scl; SSA; U1 Sn ribonuclear protein; Mi-1; Mi-1; Jo-1; Ku; and SRP. Panels for scieroderma may include Scl-70; centromere; U1 ribonuclear proteins; and fibrillarin. Panels for pernicious anemia may include intrinsic factor; and glycoprotein beta subunit of gastric H/K ATPase. Epitope Antigens for systemic lupus erythematosus (SLE) may include DNA; phospholipids; nuclear antigens; Ro; La; U1 ribonucleoprotein; Ro60 (SS-A); Ro52 (SS-A); La (SS-B); calreticulin; Grp78; Scl-70; histone; Sm protein; and chromatin, etc. For Grave's disease epitopes may include the Na+/l– symporter; thyrotropin receptor; Tg; and TPO.

Neurodegenerative Diseases

Several examples of neurodegenerative diseases associated with self-protein(s), -polypeptide(s) or -peptide(s) present in the animal non-physiologically is shown in the table and described below.

TABLE 3

| Neurodegenerative Disease | Pathologic Deformity | Self-Protein(S), -Polypepetide Or -Peptide Present Non-Physiologically |
|---|---|---|
| Alzheimer's disease | senile plaques | amyloid β protein |
| Parkinson's disease | Lewy bodies | α-synuclein |
| Huntington's disease | intranuclear inclusions | Huntingtin protein |
| Prion disease | Prion protein inclusions | Prion protein |

Alzheimer's Disease Alzheimer's disease (AD) is the most common neurodegenerative disease in the population (Cummings et al., Neurology 51, S2-17; discussion S65-7, 1998). AD affects approximately 10% of people over age 65 and almost 50% of people over age 85. It is estimated that by the year 2025, about 22 million individuals will be afflicted with AD. AD is characterized by a slowly progressive dementia.

The definitive diagnosis of AD is made if the triad of dementia, neurofibrillary tangles, and senile plaques are found postmortem. Senile plaques are invariably found in the brains of patients with Alzheimer disease. The principal constituent of senile plaques is amyloid beta protein (Aβ) (Iwatsubo et al., Neuron 13:45-53, 1994) (Lippa et al., Lancet 352:1117-1118, 1998) another example of a self-protein, -polypeptide or -peptide of this invention. Aβ is a 42 amino acid peptide that is derived from the amyloid precursor protein (APP), which is a transmembrane glycoprotein with a variety of physiologic roles, including cell proliferation, adhesion, cell signaling, and neurite outgrowth (Sinha et al., Ann N Y Acad Sci 920: 206-8, 2000). APP is normally cleaved within the Aβ domain to generate a secreted fragment. However, alternative processing leads to the cleavage of APP to generate soluble Aβ that can accumulate within senile plaques.

The current therapies for AD are limited in efficacy and are not targeted to the Aβ accumulation. The available drugs are central cholinesterase inhibitors aimed at increasing the concentration of postsynaptic acetylcholine in the brain (Farlow and Evans, Neurology 51, S36-44; discussion S65-7, 1998); (Hake, Cleve Clin J Med 68, 608-9:613-4, 616, 2001). These drugs provide minimal clinical benefit in only a few cognitive parameters. A mouse transgenic for human Aβ has been shown to have many features in common with human AD (Games et al., Nature 373:523-527, 1995); (Hsiao et al., Science 274:99-102, 1996). In these transgenic mice, immunization with the Aβ peptide has demonstrated efficacy in terms of cognitive improvement and reduced histopathology (Morgan et al., Nature 408:982-985, 2000); (Schenk et al., Nature 400:173-177, 1999). Studies have also shown that creating an antibody response against Aβ with a peptide vaccine in animal models of Alzheimer disease can reverse the abnormal histopathology as well as the behavioral changes observed in these models (Bard et al., Nat Med 6:916-19, 2000); (DeMattos et al., Proc Natl Acad Sci U S A 98:8850-8855, 2001).

Parkinson's Disease Parkinson's disease is a neurodegenerative disease of the extrapyramidal motor system that has a very high prevalence of 128-168 per 100,000 (Schrag et al., Bmj 321:21-22, 2000). The cardinal clinical features are resting tremor, bradykinesia, rigidity, and postural instability. Dementia also occurs in the majority of cases in its late stages. The pathophysiologic hallmark is the loss of neurons within the extrapyramidal system of the brain and especially within the substantia nigra. Many neurons within the brains of patients with Parkinson's disease have an intracellular inclusion known as a Lewy body (Forno and Norville, Acta Neuropathol (Berl) 34:183-197, 1976). It has been found that the major constituent of Lewy bodies is a protein known as α-synuclein, another example of a self-protein, -polypeptide, or -peptide of this invention (Dickson, Curr Opin Neurol 14:423-432, 2001). The accumulation of Lewy bodies containing α-synuclein has been correlated with the disease phenotype.

Current therapies for Parkinson's disease are directed at managing the resultant symptoms of the disease but not the underlying cause (Jankovic, Neurology 55:S2-6, 2000). The available drugs for Parkinson's disease are classified as dopaminergic agents (e.g., carbidopa/levodopa and selegiline), dopamine agonists (e.g., pergolide and ropinirole), and catechol-o-methyl-transferase or COMT inhibitors (e.g., entacapone and tolcapone). All of these therapies are directed at increasing the amount of dopamine available in the affected neurons. As a whole, these drugs are initially effective in most patients at reducing some of the motor symptoms such as tremor and rigiditiy, but are not effective in attenuating the progression of the neurodegenerative process that leads to destruction of the neurons of the substantia nigra.

Huntington's Disease Huntington's disease is a genetic disorder inherited in an autosomal dominant fashion and linked to an abnormal expansion in the length of a CAG trinucleotide repeat contained within a gene called huntingtin (Cell 72, 971-983 1993). The predominant clinical features consist of an abnormal uncontrollable movement called chorea and a progressive dementia. Pathophysiologically there is selective neuronal death and degeneration within the corpus striatum and cerebral cortex. The neurons within these regions have been shown to accumulate intracellular aggregates of mutant protein, huntingtin, another self-protein, -polypeptide or -peptide of this invention and this accumulation is correlated with disease phenotype (DiFiglia et al., Science 277: 1990-1993, 1997); (Scherzinger et al., Cell 90:549-558, 1997); (Davies et al., Cell 90:537-548, 1997).

There are currently no available treatments for either the symptoms of or the etiologic cause of Huntington's disease. As a result, these patients slowly progress to inevitable death on average 17 years after the first onset of symptoms.

Prion Disease Prion disease, also known as transmissible spongiform encephalopathy, is a potentially infectious disease which affects animals and humans and is characterized by a sponge-like degeneration of the brain (Prusiner, Proc Natl Acad Sci U S A 95, 13363-83, 1998). The most common form of this disorder is also termed Creutzfeldt-Jakob disease. Another form of the disease called new-variant Creutzfeldt-Jakob disease has major public health implications because it is felt to occur by cross-species transmission, for example from cattle to man. The clinical features of this group of disorders includes a rapidly progressive dementia, myoclonus, weakness, and ataxia. Pathophysiologically, it has been reported in the literature that a conformational change in the normal prion protein, a self-protein, polypeptide or peptide of this invention, causes the accumulation of the prion protein into a beta sheet type structure, leading to the degeneration seen within the central nervous system. Presently there are no treatments available for prion disease. The clinical course is rapid with inevitable death usually within two years of diagnosis and no intervention has been able to alter this course.

Other Diseases

Several examples of other diseases associated with self-protein(s), -polypeptide(s) or -peptide(s) present in the animal non-physiologically are set forth in the table and described below.

TABLE 4

| Disease | Abnormality | Self-Protein(s), Polypeptide(s) or Peptide(s) Associated With Disease And Present Non-Physiologically |
| --- | --- | --- |
| Obesity | weight gain due to energy intake > expenditure | syndecan-3, perilipin, Orexin, Galanin, glucogon-like peptide receptor, |
| Osteoarthritis | cartilage degeneration | cathepsins, plasmin, collagenases, metalloproteinases |
| Spinal cord injury | inhibition of regeneration | Nogo-1 |
| Hypertension | persistent high blood pressure | angiotensin-converting enzyme |
| Peptic ulcer disease | excess stomach acid | $H^+/K^+$ ATPase, gastrin |
| Aging | | superoxide dismutase |

TABLE 4-continued

| Disease | Abnormality | Self-Protein(s), Polypeptide(s) or Peptide(s) Associated With Disease And Present Non-Physiologically |
|---|---|---|
| Depression | excessive serotonin | serotonin 5HT2 receptor, $\alpha_1$-adrenergic receptor |
| Gout | Excess uric acid | Xanthine oxidase |
| Migraine headaches | vasospasm | serotonin $5HT_{1B}$ and $5HT_{1D}$ receptors |
| Hyperlipidemia | elevated lipids | HMG CoA-reductase, apolipoproteins A, B-100 |
| Coronary artery disease | obstruction of coronary arteries restricting blood flow | Angiotensin-converting enzyme, apolipoproteins A, B-100 |

Osteoarthritis and Degnerative Joint Diseases Osteoarthritis (OA) affects 30% of people over 60 years of age, and is the most common joint disease of humans. Osteoarthritis represents the degeneration and failure of synovial joints, and involves breakdown of the articular cartilage.

Cartilage is composed primarily of proteoglycans, which provide stiffness and ability to withstand load, and collagens that provide tensile and resistance to sheer strength. Chondrocytes turnover and remodel normal cartilage by producing and secreting latent collagenases, latent stromelysin, latent gelatinase, tissue plasminogen activator and other associated enzymes, each of which alone or in combination is a self-protein(s), -polypeptide or -peptide of this invention. Several inhibitors, including tissue inhibitor of metalloproteinase (TIMP) and plasminogen activator inhibitor (PAI-1), are also produced by chondrocytes and limit the degradative activity of neutral metalloproteinases, tissue plasminogen activator, and other enzymes. These degradative enzymes and inhibitors, alone or in combination are the self-protein(s), polypeptide(s) or peptide(s) of this invention. These degradative enzymes and inhibitors coordinate remodeling and maintenance of normal cartilage. In OA, dysregulation of this process results in the deterioration and degradation of cartilage.

In early OA there are abnormal alterations in the arrangement and size of collagen fibers. Metalloproteinases, cathepsins, and plasmin, alone or in combination are self-protein(s), -polypeptide(s), or -peptide(s) of this invention, cause significant cartilage matrix loss. Initially increased chondrocyte production of proteoglycans and cartilage results in the articular cartilage being thicker than normal. The articular cartilage then thins and softens as a result of the action of degradative enzymes including collagenases, stromelysin, gelatinase, tissue plasminogen activator and other related enzymes, alone or in combination are self-protein(s), -polypeptide(s), or -peptide(s) of this invention. IL-1, cathepsins, and plasmin may promote the degeneration and breakdown of cartilage alone or in combination and are self-protein(s), -polypeptide(s), or -peptide(s) of this invention. The softer and thinner cartilage is much more susceptible to damage by mechanical stress. These factors lead to the breakdown of the cartilage surface and the formation of vertical clefts (fibrillation). Erosions in the cartilage surface form, and extend to bone in end-stage disease. Chondrocytes initially replicate and form clusters, and at end-stage the cartilage is hypocelluar. Remodeling and hypertrophy of bone are significant features of OA.

Current therapies for OA include rest, physical therapy to strengthen muscles supporting the joint, braces and other supportive devices to stabilize the joint, non-steroidal anti-inflammatory agents, Tylenol, and other analgesics. In end-stage bone-on-bone OA of joints critical for activities of daily living, such as the knees or hips, surgical joint replacement is performed.

Obesity Obesity is a major health problem facing the United States and other industrialized countries. It is estimated that obesity affects 20% of the U.S. population. Obesity is the excess of adipose tissue. When prolonged energy intake exceeds expenditure for prolonged periods, excess calories are stored as adipose tissue resulting in obesity. Obesity can thus result from increased intake and/or decreased expenditure. Intake is dependent on eating behavior, which is a complex process controlled by the cerebral cortex. Discrete regions of the hypothalamus, including the feeding center and the satiety center send signals to the cerebral cortex to facilitate the regulation of feeding. Blood glucose, insulin, glycerol and other levels may be detected by the feeding and satiety centers in the hypothalamus to help regulate feeding behavior.

Humans can partially adapt to excessive intake of calories by several mechanisms. Excess intake of carbohydrate and protein can be, in part, compensated for by increasing the resting metabolic rate through mechanisms that increase plasma levels of triiodothyronine (T3) and decrease levels of reverse T3 (rT3). Increased central or peripheral sympathetic outflow also increase catecholamine-induced caloric usage and heat production. Dietary thermogenesis, or the body's thermal response to food involves increased heat and metabolic expenditure above the resting metabolic rate for several hours following ingestion of a meal and is greater for protein, than for carbohydrate or fat based meals.

Feeding behavior and adipogenesis are controlled by complex mechanisms. Molecules including syndecan-3 regulates feeding and increases feeding behavior in the hypothalamus (Reizes et al, Cell 106:105-116, 2001). Other molecules and receptors that impact food intake and metabolism include Orexin, Galanin, corticotrophin-releasing factor, melanin-concentrating hormone, leptin, cholecystokinin, somatostatin, enterostating, glucagons-like peptides 1 and 2, and bombesin, all of which either alone or in combination are the self-protein(s), -polypeptide(s) or -peptide(s) of this invention. (Chiesi et al, Trends Pharmacological Sciences, 22:247-54, 2001). In animal models of obesity, antagonists or agonists of several of these molecules have demonstrated efficacy in weight reduction (Chiesi et al, Trends Pharmacological Sciences, 22:247-54, 2001). Perilipin coats lipid droplets of adipocytes and regulates triacylglycerol hydrolysis, and interference with perilipin resulted in mice resistant to diet-induced obesity but with normal glucose tolerance (Tansey et al, Proc. Natl. Acad. Sci. USA, 98:6494-99).

When obesity is secondary to a secondary metabolic or other disease state, that secondary cause is treated. Primary obesity is treated by diet regimens and eating behavior modification to reduce caloric intake, and exercise regimens to increase expenditure. Anorexiants (amphetamine-like agents), thyroid hormone drugs, and human chorionic gonadotrophin have been used to treat obesity. Surgical small bowel bypass (jujunoileal shunts) is also used to treat severe cases of morbid obesity.

Spinal Cord Injury It is estimated that there are approximately 11,000 new cases of spinal cord injury every year in the U.S. and that the overall prevalence is a total of 183,000 to 230,000 cases in the U.S. presently (Stover et al., Arch Phys Med Rehabil 80, 1365-71, 1999). Recovery from spinal cord injury is very poor and results in devastating irreversible neurologic disability. Current treatment of acute spinal cord injury consists of mechanical stabilization of the injury site, for example by surgical intervention, and the administration of parenteral steroids. These interventions have done little to reduce the incidence of permanent paralysis following spinal cord injury. Treatment of chronic spinal cord injury is focused on maintenance of quality of life such as the management of pain, spasticity, and bladder function. No currently available treatment addresses the recovery of neurologic function.

One of the factors responsible for such poor recovery after spinal cord injury is the presence of axonal regrowth inhibitors in the myelin sheath. These factors are released shortly after injury and prevent axons from growing across the lesion to re-establish functional connections. One of these axonal regrowth inhibitors is a protein called Nogo-A, a self-protein, -polypeptide or -peptide of this invention (Huber and Schwab, Biol Chem 381, 407-19., 2000; Reilly, J Neurol 247, 239-40, 2000; Chen et al., Nature 403, 434-9, 2000). Nogo-A has been shown in vitro to inhibit neurite outgrowth, and neutralizing antibodies against Nogo-A have been shown to reverse this growth inhibitory property. Furthermore, monoclonal antibodies against Nogo-A have been shown to promote axonal regrowth in vivo in animal models of spinal cord injury (Raineteau et al., Proc Natl Acad Sci U S A 98, 6929-34., 2001; Merkler et al., J Neurosci 21, 3665-73, 2001; Blochlinger et al., J Comp Neurol 433, 426-36, 2001; Brosamle et al., J Neurosci 20, 8061-8, 2000). Nogo-A is a transmembrane protein expressed mainly in oligodendrocytes within the cerebral cortex and spinal cord. Two regions of the Nogo-A molecule the have been identified as potentially responsible for the inhibitory capacity of this molecule, namely an extracellular 66 amino acid loop and an intracytoplasmic C-terminal region termed AS472.

Graft Versus Host Disease One of the greatest limitations of tissue and organ transplantation in humans is rejection of the tissue transplant by the recipient's immune system. It is well established that the greater the matching of the MHC class I and II (HLA-A, HLA-B, and HLA-DR) alleles between donor and recipient the better the graft survival. Graft versus host disease (GVHD) causes significant morbidity and mortality in patients receiving transplants containing allogeneic hematopoietic cells. Hematopoietic cells are present in bone-marrow transplants, stem cell transplants, and other transplants. Approximately 50% of patients receiving a transplant from a HLA-matched sibling will develop moderate to severe GVHD, and the incidence is much higher in non-HLA-matched grafts. One-third of patients that develop moderate to severe GVHD will die as a result. T lymphocytes and other immune cell in the donor graft attack the recipients cells that express polypeptides variations in their amino acid sequences, particularly variations in proteins encoded in the major histocompatibility complex (MHC) gene complex on chromosome 6 in humans. The most influential proteins for GVHD in transplants involving allogeneic hematopoietic cells are the highly polymorphic (extensive amino acid variation between people) class I proteins (HLA-A, -B, and -C) and the class II proteins (DRB1, DQB1, and DPB1) (Appelbaum, Nature 411:385-389, 2001). Even when the MHC class I alleles are serologically 'matched' between donor and recipient, DNA sequencing reveals there are allele-level mismatches in 30% of cases providing a basis for class I-directed GVHD even in matched donor-recipient pairs (Appelbaum, Nature 411, 385-389, 2001). The minor histocompatibility self-antigens GVHD frequently causes damage to the skin, intestine, liver, lung, and pancreas. GVHD is treated with glucocorticoids, cyclosporine, methotrexate, fludarabine, and OKT3.

Tissue Transplant Rejection Immune rejection of tissue transplants, including lung, heart, liver, kidney, pancreas, and other organs and tissues, is mediated by immune responses in the transplant recipient directed against the transplanted organ. Allogeneic transplanted organs contain proteins with variations in their amino acid sequences when compared to the amino acid sequences of the transplant recipient. Because the amino acid sequences of the transplanted organ differ from those of the transplant recipient they frequently elicit an immune response in the recipient against the transplanted organ. Rejection of transplanted organs is a major complication and limitation of tissue transplant, and can cause failure of the transplanted organ in the recipient. The chronic inflammation that results from rejection frequently leads to dysfunction in the transplanted organ. Transplant recipients are currently treated with a variety of immunosuppressive agents to prevent and suppress rejection. These agents include glucocorticoids, cyclosporin A, Cellcept, FK-506, and OKT3.

Polynucleotide Therapy—Materials and Methods

Before describing the present invention in detail, it is to be understood that this invention is not limited to particular formulations or process parameters as they may, of course, vary. It is also to be understood that the terminology used herein is for the purpose of describing particular embodiments of the invention only, and is not intended to be limiting.

Although a number of materials and methods similar or equivalent to those described herein can be used in the practice of the present invention, the preferred materials and methods are described herein.

"Self-vector" means one or more vector(s) which taken together comprise a polynucleotide either DNA or RNA encoding one or more self-protein(s), -polypeptide(s), -peptide(s). Polynucleotide, as used herein is a series of either deoxyribonucleic acids including DNA or ribonucleic acids including RNA, and their derivatives, encoding a self-protein, -polypeptide, or -peptide of this invention. The self-protein, -polypeptide or -peptide coding sequence is inserted into an appropriate plasmid expression self-cassette. Once the polynucleotide encoding the self-protein, -polypeptide, or -peptide is inserted into the expression self-cassette the vector is then referred to as a "self-vector." In the case where polynucleotide encoding more than one self-protein(s), -polypeptide(s), or -peptide(s) is to be administered, a single self-vector may encode multiple separate self -protein(s), -polypeptide(s) or -peptide(s). In one embodiment, DNA encoding several self-protein(s), -polypeptide(s), or -peptide(s) are encoded sequentially in a single self-plasmid utilizing internal ribosomal re-entry sequences (IRES) or other methods to express multiple proteins from a single DNA molecule. The DNA expression self-vectors encoding the self-protein(s), -polypeptide(s), or -peptide(s) are prepared and isolated using commonly available techniques for isolation of plasmid DNA such as those commercially available from Qiagen Corporation. The DNA is purified free of bacterial endotoxin for delivery to humans as a therapeutic agent. Alternatively, each self-protein, -polypeptide or -peptide is encoded on a separate DNA expression vector.

"Self-protein, -polypeptide, or -peptide" as used herein refers to any protein, polypeptide, or peptide, or fragment or derivative thereof that: is encoded within the genome of the animal; is produced or generated in the animal; may be modified posttranslationally at some time during the life of the animal; and, is present in the animal non-physiologically. The term "non-physiological" or "non-physiologically" when used to describe the self-proteins, -polypeptides, or -peptides of this invention means a departure or deviation from the normal role or process in the animal for that self-protein, -polypeptide or -peptide. When referring to the self-protein, -polypeptide or -peptide as "associated with a disease" or "involved in a disease" it is understood to mean that the self-protein, -polypeptide, or -peptide may be modified in form or structure and thus be unable to perform its physiological role or process; or may be involved in the pathophysiology of the condition or disease either by inducing the pathophysiology, mediating or facilitating a pathophysiologic process; and/or by being the target of a pathophysiologic process. For example, in autoimmune disease, the immune system aberrantly attacks self-proteins causing damage and dysfunction of cells and tissues in which the self-protein is expressed and/or present. Alternatively, the self-protein, -polypeptide or -peptide can itself be expressed at non-physiological levels and/or function non-physiologically. For example in neurodegenerative diseases self-proteins are aberrantly expressed, and aggregate in lesions in the brain thereby causing neural dysfunction. In other cases, the self-protein aggravates an undesired condition or process. For example in osteoarthritis, self-proteins including collagenases and matrix metalloproteinases aberrantly degrade cartilage covering the articular surface of joints. Examples of posttranslational modifications of self-protein(s), -polypeptide(s) or -peptide(s) are glycosylation, addition of lipid groups, dephosphorylation by phosphatases, addition of dimethylarginine residues, citrullination of fillagrin and fibrin by peptidyl arginine deiminase (PAD); alpha B crystallin phosphorylation; citrullination of MBP; and SLE autoantigen proteolysis by caspases and granzymes). Immunologically, self-protein, -polypeptide or -peptide would all be considered host self-antigens and under normal physiological conditions are ignored by the host immune system through the elimination, inactivation, or lack of activation of immune cells that have the capacity to recognize self-antigens through a process designated "immune tolerance." Antigen refers to any molecule that can be recognized by the immune system that is by B cells or T cells, or both. Self-protein, -polypeptide, or -peptide does not include immune proteins, polypeptides, or peptides which are molecules expressed physiologically, specifically and exclusively by cells of the immune system for the purpose of regulating immune function. The immune system is the defense mechanism that provides the means to make rapid, highly specific, and protective responses against the myriad of potentially pathogenic microorganisms inhabiting the animal's world. Examples of immune protein(s), polypeptide(s) or peptide(s) are proteins comprising the T-cell receptor, immunoglobulins, cytokines including the type I interleukins, and the type II cytokines, including the interferons and IL-10, TNF, lymphotoxin, and the chemokines such as macrophage inflammatory protein-1alpha and beta, monocyte-chemotactic protein and RANTES, and other molecules directly involved in immune function such as Fas-ligand. There are certain immune proteins, polypeptide(s) or peptide(s) that are included in the self-protein, -polypeptide or -peptide of the invention and they are: class I MHC membrane glycoproteins, class II MHC glycoproteins and osteopontin. Self-protein, -polypeptide or -peptide does not include proteins, polypeptides, and peptides that are absent from the subject, either entirely or substantially, due to a genetic or acquired deficiency causing a metabolic or functional disorder, and are replaced either by administration of said protein, polypeptide, or peptide or by administration of a polynucleotide encoding said protein, polypeptide or peptide (gene therapy). Examples of such disorders include Duchenne' muscular dystrophy, Becker's muscular dystrophy, cystic fibrosis, phenylketonuria, galactosemia, maple syrup urine disease, and homocystinuria. Self-protein, -polypeptide or -peptide does not include proteins, polypeptides, and peptides expressed specifically and exclusively by cells which have characteristics that distinguish them from their normal counterparts, including: (1) clonality, representing proliferation of a single cell with a genetic alteration to form a clone of malignant cells, (2) autonomy, indicating that growth is not properly regulated, and (3) anaplasia, or the lack of normal coordinated cell differentiation. Cells have one or more of the foregoing three criteria are referred to either as neoplastic, cancer or malignant cells.

"Modulation of, modulating or altering an immune response" as used herein refers to any alteration of existing or potential immune response(s) against self-molecules, including but not limited to nucleic acids, lipids, phospholipids, carbohydrates, self-protein(s), -polypeptide(s), -peptide(s), protein complexes, ribonucleoprotein complexes, or derivative(s) thereof that occurs as a result of administration of a polynucleotide encoding a self-protein, -polypeptide, -peptide, nucleic acid, or a fragment or derivative thereof. Such modulation includes any alteration in presence, capacity or function of any immune cell involved in or capable of being involved in an immune response. Immune cells include B cells, T cells, NK cells, NK T cells, professional antigen-presenting cells, non-professional antigen-presenting cells, inflammatory cells, or any other cell capable of being involved in or influencing an immune response. Modulation includes any change imparted on an existing immune response, a developing immune response, a potential immune response, or the capacity to induce, regulate, influence, or respond to an immune response. Modulation includes any alteration in the expression and/or function of genes, proteins and/or other molecules in immune cells as part of an immune response.

Modulation of an immune response includes; but is not limited to: elimination, deletion, or sequestration of immune cells; induction or generation of immune cells that can modulate the functional capacity of other cells such as autoreactive lymphocytes, APCs, or inflamatory cells; induction of an unresponsive state in immune cells, termed anergy; increasing, decreasing or changing the activity or function of immune cells or the capacity to do so, including but not limited to altering the pattern of proteins expressed by these cells. Examples include altered production and/or secretion of certain classes of molecules such as cytokines, chemokines, growth factors, transcription factors, kinases, costimulatory molecules, or other cell surface receptors; or any combination of these modulatory events.

For example, polynucleotides encoding self-protein(s), -polypeptide(s), -peptide(s) can modulate immune responses by eliminating, sequestering, or turning-off immune cells mediating or capable of mediating an undesired immune response; inducing, generating, or turning on immune cells that mediate or are capable of mediating a protective immune response; changing the physical or functional properties of immune cells; or a combination of these effects. Examples of measurements of the modulation of an immune response include, but are not limited to, examination of the presence or absence of immune cell populations (using flow cytometry, immunohistochemistry, histology, electron microscopy, the polymerase chain reaction); measurement of the functional capacity of immune cells including ability or resistance to proliferate or divide in response to a signal (such as using T cell proliferation assays and pepscan analysis based on $^3$H-thymidine incorporation following stimulation with anti-CD3 antibody, anti-T cell receptor antibody, anti-CD28 antibody, calcium ionophores, PMA, antigen presenting cells loaded with a peptide or protein antigen; B cell proliferation assays); measurement of the ability to kill or lyse other cells (such as cytotoxic T cell assays); measurements of the cytokines, chemokines, cell surface molecules, antibodies and other products of the cells (by flow cytometry, enzyme-linked immunosorbent assays, Western blot analysis, protein microarray analysis, immunoprecipitation analysis); measurement of biochemical markers of activation of immune cells or signaling pathways within immune cells (Western blot and immunoprecipitation, analysis of tyrosine, serine or threonine phosphorylation, polypeptide cleavage, and formation or dissociation of protein complexes; protein array analysis; DNA transcriptional profiling using DNA arrays or subtractive hybridization); measurements of cell death by apoptosis, necrosis, or other mechanisms. (annexin V staining, TUNEL assays, gel electrophoresis to measure. DNA laddering, histology; fluorogenic caspase assays, Western blot analysis of caspase substratesy; measurement of the genes, proteins, and other molecules produced by immune cells (Northern blot analysis, polymerase chain reaction, DNA microarrays, protein microarrays, 2-dimentional gel electrophoresis, Western blot analysis, enzyme linked immunosorbent assays, flow cytometry); and measurement of clinical outcomes such as improvement of autoimmune, neurodegenerative, and other diseases involving non-physiologic self proteins (clinical scores, requirements for use of additional therapies, functional status, imaging studies).

"Immune Modulatory Sequences (IMSs)" as used herein refers to compounds consisting of deoxynucleotides, ribonucleotides, or analogs thereof that modulate an autoimmune or inflammatory disease. IMSs may be oligonucleotides or a sequence of nucleotides incorporated in a vector. "Oligonucleotide" means multiple nucleotides. Nucleotides are molecules comprising a sugar (preferably ribose or deoxyribose) linked to a phosphate group and an exchangeable organic base, which can be either a substituted purine (guanine (G), adenine (A), or inosine (I)) or a substituted pyrimidine (thymine (T), cytosine (C), or uracil (U)). Oligonucleotide refers to both oligoribonucleotides and to oligodeoxyribonucleotides, herein after referred to as ODNs. ODNs include oligonucleosides and other organic base containing polymers. Oligonucleotide encompasses any length of multiple nucleotides, from a chain of two or more linked nucleotides, and includes chromosomal material containing millions of linked nucleotides.

In one aspect, the immune modulatory sequences of the invention are synthesized oligonucleotides comprised of the following primary structure:
5'-purine-pyrimidine-[X]-[Y]-pyrimidine-pyrimidine-3'
or
5'-purine-purine-[X]-[Y]-pyrimidine-pyrimidine-3';
wherein X and Y are any naturally occurring or synthetic nucleotide, except that X and Y cannot be cytosine-guanine.

The core hexamer of IMSs can be flanked 5' and/or 3' by any composition or number of nucleotides or nucleosides. Preferably, IMSs range between 6 and 100 base pairs in length, and most preferably 16-50 base pairs in length. IMSs can also be delivered as part of larger pieces of DNA, ranging from 100 to 100,000 base pairs. IMSs can be incorporated in, or already occur in, DNA plasmids, viral vectors and genomic DNA. Most preferably IMSs can also range from 6 (no flanking sequences) to 10,000 base pairs, or larger, in size. Sequences present which flank the hexamer core can be constructed to substantially match flanking sequences present in any known immunoinhibitory sequences (IIS). For example, the flanking sequences TGACTGTG-Pu-Pu-X-Y-Pyr-Pyr-AGAGATGA (SEQ ID NO:1), where TGACTGTG and AGAGATGA are flanking sequences. Another preferred flanking sequence incorporates a series of pyrimidines (C, T, and U), either as an individual pyrimidine repeated two or more times, or a mixture of different pyrimidines two or more in length. Different flanking sequences have been used in testing inhibitory modulatory sequences. Further examples of flanking sequences for inhibitory oligonucleotides are contained in the following references: U.S. Pat. Nos. 6,225,292 and 6,339,068, and Zeuner et al., Arthritis and Rheumatism, 46:2219-24, 2002. Particular IMSs of the invention include oligonucleotides containing the following hexamer sequences:
5'-purine-pyrimidine-[X]-[Y]-pyrimidine-pyrimidine-3'
  IMSs containing GG dinucleotide cores: GTGGTT, ATGGTT, GCGGTT, ACGGTT, GTGGCT, ATGGCT, GCGGCT, ACGGCT, GTGGTC, ATGGTC, GCGGTC, ACGGTC, and so forth.
5'-purine-pyrimidine-[X]-[Y]-pyrimidine-pyrimidine-3'
  IMSs containing GC dinucleotides cores: GTGCTT, ATGCTT, GCGCTT, ACGCTT, GTGCCT, ATGCCT, GCGCCT, ACGCCT, GTGCTC, ATGCTC, GCGCTC, ACGGTC, and so forth.

Guanine and inosine substitutes for adenine and/or uridine substitutes for cytosine or thymine and those substitutions can be made as set forth based on the guidelines above.

A previously disclosed immune inhibitory sequence or IIS, was shown to inhibit immunostimulatory sequences (ISS) activity containing a core dinucleotide, CpG. U.S. Pat. No. 6,225,292. This IIS, in the absence of an ISS, was shown for the first time by this invention to prevent and treat autoimmune disease either alone or in combination with DNA polynucleotide therapy. This IIS contained the core hexamer AAGGTT. That sequence is referred to herein as an immune modulatory sequence or IMS. Other related IISs with a similar motif included within the IMSs of this invention are:
5'-purine-purine-[X]-[Y]-pyrimidine-pyrimidine-3'   IMSs containing GG dinucleotide cores: GGGGTT, AGGGTT, GAGGTT, AAGGTT, GGGGCT, AGGGCT, GAGGCT, MGGCT, GGGGTC, AGGGTC, GAGGTC, MGGTC, and so forth.
5'-purine-purine-[X]-[Y]-pyrimidine-pyrimidine-3'   IMSs containing GC dinucleotide cores: GGGCTT, AGGCTT, GAGCTT, MGCTT, GGGCCT, AGGCCT, GAGCCT, MGCCT, GGGCTC, AGGCTC, GAGCTC, AAGCTC, and so forth.
3. Guanine and inosine substitutions for adenine and/or uridine substitutions for cytosine or thymine can be made as set forth based on the guidelines above.

Oligonucleotides can be obtained from existing nucleic acid sources, including genomic DNA, plasmid DNA, viral DNA and cDNA, but are preferably synthetic oligonucleotides produced by oligonucleotide synthesis. IMS can be part of single-strand or double-stranded DNA, RNA and/or oligonucleosides.

IMSs are preferentially oligonucleotides that contain unmethylated GpG oligonucleotides. Alternative embodiments include IMSs in which one or more adenine or cytosine residues are methylated. In eukaryotic cells, typically cytosine and adenine residues can be methylated.

IMSs can be stabilized and/or unstabilized oligonucleotides. Stabilized oligonucleotides mean oligonucleotides that are relatively resistant to in vivo degradation by exonucleases, endonucleases and other degradation pathways. Preferred stabilized oligonucleotides have modified phophate backbones, and most preferred oligonucleotides have phophorothioate modified phosphate backbones in which at least one of the phosphate oxygens is replaced by sulfur. Backbone phosphate group modifications, including methylphosphonate, phosphorothioate, phophoroamidate and phosphorodithionate internucleotide linkages, can provide antimicrobial properties on IMSs. The IMSs are preferably stabilized oligonucleotides, preferentially using phosphorothioate stabilized oligonucleotides.

Alternative stabilized oligonucleotides include: alkylphosphotriesters and phosphodiesters, in which the charged oxygen is alkylated; arylphosphonates and alkylphosphonates, which are nonionic DNA analogs in which the charged phosphonate oxygen is replaced by an aryl or alkyl group; or/and oligonucleotides containing hexaethyleneglycol or tetraethyleneglycol, or another diol, at either or both termini. Alternative steric configurations can be used to attach sugar moieties to nucleoside bases in IMSs.

The nucleotide bases of the IMS which flank the modulating dinucleotides may be the known naturally occurring bases or synthetic non-natural bases. Oligonucleosides may be incorporated into the internal region and/or termini of the IMS-ON using conventional techniques for use as attachment points, that is as a means of attaching or linking other molecules, for other compounds, including self-lipids, self-protein(s), self-peptide(s), self-polypeptide(s), self-glycolipid(s), self-carbohydrate(s), self-glycoprotein(s), and posttranslationally-modified self-protein(s), peptide(s), polypeptide(s), or glycoprotein(s), or as attachment points for additional immune modulatory therapeutics. The base(s), sugar moiety, phosphate groups and termini of the IMS-ON may also be modified in any manner known to those of ordinary skill in the art to construct an IMS-ON having properties desired in addition to the modulatory activity of the IMS-ON. For example, sugar moieties may be attached to nucleotide bases of IMS-ON in any steric configuration.

The techniques for making these phosphate group modifications to oligonucleotides are known in the art and do not require detailed explanation. For review of one such useful technique, the intermediate phosphate triester for the target oligonucleotide product is prepared and oxidized to the naturally occurring phosphate triester with aqueous iodine or with other agents, such as anhydrous amines. The resulting oligonucleotide phosphoramidates can be treated with sulfur to yield phophorothioates. The same general technique (excepting the sulfur treatment step) can be applied to yield methylphosphoamidites from methylphosphonates. For more details concerning phosphate group modification techniques, those of ordinary skill in the art may wish to consult U.S. Pat. Nos. 4,425,732; 4,458,066; 5,218,103 and 5,453,496, as well as Tetrahedron Lett. at 21:4149 25 (1995), 7:5575 (1986), 25:1437 (1984) and Journal Am. ChemSoc., 93:6657 (1987), the disclosures of which are incorporated herein for the purpose of illustrating the level of knowledge in the art concerning the composition and preparation of IMSs.

A particularly useful phosphate group modification is the conversion to the phosphorothioate or phosphorodithioate forms of the IMS-ON oligonucleotides. Phosphorothioates and phosphorodithioates are more resistant to degradation in vivo than their unmodified oligonucleotide counterparts, making the IMS-ON of the invention more available to the host.

IMS-ON can be synthesized using techniques and nucleic acid synthesis equipment which are well-known in the art. For reference in this regard, see, e.g., Ausubel, et al., Current Protocols in Molecular Biology, Chs. 2 and 4 (Wiley Interscience, 1989); Maniatis, et al., Molecular Cloning: A Laboratory Manual (Cold Spring Harbor Lab., New York, 1982); U.S. Pat. No. 4,458,066 and U.S. Pat. No. 4,650,675. These references are incorporated herein by reference for the purpose of demonstrating the level of knowledge in the art concerning production of synthetic oligonucleotides.

Alternatively, IMS-ON can be obtained by mutation of isolated microbial ISS-ODN to substitute a competing dinucleotide for the naturally occurring CpG motif and the flanking nucleotides. Screening procedures which rely on nucleic acid hybridization make it possible to isolate any polynucleotide sequence from any organism, provided the appropriate probe or antibody is available. Oligonucleotide probes, which correspond to a part of the sequence encoding the protein in question, can be synthesized chemically. This requires that short, oligo-peptide stretches of amino acid sequence must be known. The DNA sequence encoding the protein can also be deduced from the genetic code, however, the degeneracy of the code must be taken into account.

For example, a cDNA library believed to contain an ISS-containing polynucleotide can be screened by injecting various mRNA derived from cDNAs into oocytes, allowing sufficient time for expression of the cDNA gene products to occur, and testing for the presence of the desired cDNA expression product, for example, by using antibody specific for a peptide encoded by the polynucleotide of interest or by using probes for the repeat motifs and a tissue expression pattern characteristic of a peptide encoded by the polynucelotide of interest. Alternatively, a cDNA library can be screened indirectly for expression of peptides of interest having at least one epitope using antibodies specific for the peptides. Such antibodies can be either polyclonally or monoclonally derived and used to detect expression product indicative of the presence of cDNA of interest.

Once the ISS-containing polynucleotide has been obtained, it can be shortened to the desired length by, for example, enzymatic digestion using conventional techniques. The CpG motif in the ISS-ODN oligonucleotide product is then mutated to substitute an "inhibiting" dinucleotide—identified using the methods of this invention—for the CpG motif. Techniques for making substitution mutations at particular sites in DNA having a known sequence are well known, for example M13 primer mutagenesis through PCR. Because the IMS is non-coding, there is no concern about maintaining an open reading frame in making the substitution mutation. However, for in vivo use, the polynucleotide starting material, ISS-ODN oligonucleotide intermediate or IMS mutation product should be rendered substantially pure (i.e., as free of naturally occurring contaminants and LPS as is possible using available techniques known to and chosen by one of ordinary skill in the art).

The IMS of the invention may be used alone or may be incorporated in cis or in trans into a recombinant self-vector (plasmid, cosmid, virus or retrovirus) which may in turn code for any self-protein(s), -polypeptide(s), or -peptide(s) deliverable by a recombinant expression vector. For the sake of convenience, the IMSs are preferably administered without incorporation into an expression vector. However, if incorporation into an expression vector is desired, such incorporation may be accomplished using conventional techniques as known to one of ordinary skill in the art. For review those of ordinary skill would consult Ausubel, Current Protocols in Molecular Biology, supra.

Briefly, construction of recombinant expression vectors employs standard ligation techniques. For analysis to confirm correct sequences in vectors constructed, the ligation mixtures may be used to transform a host cell and successful transformants selected by antibiotic resistance where appropriate. Vectors from the transformants are prepared, analyzed by restriction and/or sequenced by, for example, the method of Messing, et al., (Nucleic Acids Res., 9:309, 1981), the method of Maxam, et al., (Methods in Enzymology, 65:499, 1980), or other suitable methods which will be known to those skilled in the art. Size separation of cleaved fragments is performed using conventional gel electrophoresis as described, for example, by: Maniatis, et al., (Molecular Cloning, pp. 133-134, 1982).

Host cells may be transformed with the expression vectors of this invention and cultured in conventional nutrient media modified as is appropriate for inducing promoters, selecting transformants or amplifying genes. The culture conditions, such as temperature, pH and the like are those previously used with the host cell selected for expression, and will be apparent to the ordinarily skilled artisan.

If a recombinant expression vector is utilized as a carrier for the IMS-ON of the invention, plasmids and cosmids are particularly preferred for their lack of pathogenicity. However, plasmids and cosmids are subject to degradation in vivo more quickly than viruses and therefore may not deliver an adequate dosage of IMS-ON to prevent or treat an inflammatory or autoimmune disease.

Most of the techniques used to construct vectors, and transfect and infect cells, are widely practiced in the art, and most practitioners are familiar with the standard resource materials that describe specific conditions and procedures.

"Plasmids" and "vectors" are designated by a lower case p followed by letters and/or numbers. The starting plasmids are commercially available, publicly available on an unrestricted basis, or can be constructed from available plasmids in accord with published procedures. In addition, equivalent plasmids to those described are known in the art and will be apparent to the ordinarily skilled artisan. A "vector" or "plasmid" refers to any genetic element that is capable of replication by comprising proper control and regulatory elements when present in a host cell. For purposes of this invention examples of vectors or plasmids include, but are not limited to, plasmids, phage, transposons, cosmids, virus, etc.

Construction of the vectors of the invention employs standard ligation and restriction techniques which are well understood in the art (see Ausubel et al., (1987) Current Protocols in Molecular Biology, Wiley Interscience or Maniatis et al., (1992) in Molecular Cloning: A laboratory Manual, Cold Spring Harbor Laboratory, N.Y.). Isolated plasmids, DNA sequences, or synthesized oligonucleotides are cleaved, tailored, and relegated in the form desired. The sequences of all DNA constructs incorporating synthetic DNA were confirmed by DNA sequence analysis (Sanger et al. (1977) Proc. Natl. Acad. Sci. 74, 5463-5467).

"Digestion" of DNA refers to catalytic cleavage of the DNA with a restriction enzyme that acts only at certain sequences, restriction sites, in the DNA. The various restriction enzymes used herein are commercially available and their reaction conditions, cofactors and other requirements are known to the ordinarily skilled artisan. For analytical purposes, typically 1 µg of plasmid or DNA fragment is used with about 2 units of enzyme in about 20 µl of buffer solution. Alternatively, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in Methods of Enzymology 65:499-560 (1980).

Restriction cleaved fragments may be blunt ended by treating with the large fragment of E. coli DNA polymerase I (Klenow) in the presence of the four deoxynucleotide triphosphates (dNTPs) using incubation times of about 15 to 25 minutes at 20° C. in 50 mM Tris (ph7.6) 50 mM NaCl, 6 mM $MgCl_2$, 6 mM DTT and 5-10 µM dNTPs. The Klenow fragment fills in at 5' sticky ends but chews back protruding 3' single strands, even though the four dNTPs are present. If desired, selective repair can be performed by supplying only one of the dNTPs, or with selected dNTPs, within the limitations dictated by the nature of the sticky ends. After treatment with Klenow, the mixture is extracted with phenol/chloroform and ethanol precipitated. Treatment under appropriate conditions with S1 nuclease or Bal-31 results in hydrolysis of any single-stranded portion.

Ligations are performed in 15-50 µl volumes under the following standard conditions and temperatures: 20 mM Tris-Cl pH 7.5, 10 mM $MgCl_2$, 10 mM DTT, 33 mg/ml BSA, 10 mM-50 mM NaCl, and either 40 µm ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 33-100 µg/ml total DNA concentrations. Intermolecular blunt end ligations are performed employing a molar excess of linkersover ends.

The expression self-cassette will employ a promoter that is functional in host cells. In general, vectors containing promoters and control sequences that are derived from species compatible with the host cell are used with the particular host cell. Promoters suitable for use with prokaryotic hosts illustratively include the beta-lactamase and lactose promoter systems, alkaline phosphatase, the tryptophan (trp) promoter system and hybrid promoters such as tac promoter. However, other functional bacterial promoters are suitable. In addition to prokaryotes, eukaryotic microbes such as yeast cultures may also be used. Saccharomyces cerevisiae, or common baker's yeast is the most commonly used eukaryotic microorganism, although a number of other strains are commonly available. Promoters controlling transcription from vectors in mammalian host cells may be obtained from various sources, for example, the genomes of viruses such as: polyoma, simian virus 40 (SV40), adenovirus, retroviruses, hepatitis B virus and preferably cytomegalovirus, or from heterologous mammalian promoters, e.g. β-actin promoter. The early and late promoters of the SV 40 virus are conveniently obtained as an SV40 restriction fragment which also contains the SV40 viral origin of replication. The immediate early promoter of the human cytomegalovirus is conveniently obtained as a HindIII restriction fragment. Of course, promoters from the host cell or related species also are useful herein.

The vectors used herein may contain a selection gene, also termed a selectable marker. A selection gene encodes a protein, necessary for the survival or growth of a host cell transformed with the vector. Examples of suitable selectable markers for mammalian cells include the dihydrofolate reductase gene (DHFR), the ornithine decarboxylase gene, the multidrug resistance gene (mdr), the adenosine deaminase gene, and the glutamine synthase gene. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. The second category is referred to as dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin (Southern and Berg (1982) J. Molec. Appl. Genet. 1, 327), mycophenolic acid (Mulligan and Berg (1980) Science 209, 1422), or hygromycin (Sugden et al. (1985) Mol. Cell. Bio. 5, 410-413). The three examples given above employ bacterial genes under eukaryotic control to convey resistance to the appropriate drug neomycin (G418 or genticin), xgpt (mycophenolic acid) or hygromycin, respectively.

"Transfection" means introducing DNA into a host cell so that the DNA is expressed, whether functionally expressed or otherwise; the DNA may also replicate either as an extrachromosomal element or by chromosomal integration. Unless otherwise provided, the method used herein for transformation of the host cells is the calcium phosphate co-precipitation method of Graham and van der Eb (1973) Virology 52, 456-457. Alternative methods for transfection are electroporation, the DEAE-dextran method, lipofection and biolistics (Kriegler (1990) Gene Transfer and Expression: A Laboratory Manual, Stockton Press).

Self-vectors of this invention can be formulated as polynucleotide salts for use as pharmaceuticals. Polynucleotide salts can be prepared with non-toxic inorganic or organic bases. Inorganic base salts include sodium, potassium, zinc, calcium, aluminum, magnesium, etc. Organic non-toxic bases include salts of primary, secondary and tertiary amines, etc. Such self-DNA polynucleotide salts can be formulated in lyophilized form for reconstitution prior to delivery, such as sterile water or a salt solution. Alternatively, self-DNA polynucleotide salts can be formulated in solutions, suspensions, or emulsions involving water- or oil-based vehicles for delivery. In one preferred embodiment, the DNA is lyophilized in phosphate buffered saline with physiologic levels of calcium (0.9 mM) and then reconstituted with sterile water prior to administration. Alternatively the DNA is formulated in solutions containing higher quantities of Ca++, between 1 mM and 2M. The DNA can also be formulated in the absence of specific ion species.

As known to those ordinarily skilled in the art, a wide variety of methods exist to deliver polynucleotide to subjects, as defined herein. "Subjects" shall mean any animal, such as, for example, a human, non-human primate, horse, cow, dog, cat, mouse, rat, guinea pig or rabbit. The polynucleotide encoding self-protein(s), -polypeptide(s), or -peptide(s) can be formulated with cationic polymers including cationic liposomes. Other liposomes also represent effective means to formulate and deliver self-polynucleotide. Alternatively, the self DNA can be incorporated into a viral vector, viral particle, or bacterium for pharmacologic delivery. Viral vectors can be infection competent, attenuated (with mutations that reduce capacity to induce disease), or replication-deficient. Methods utilizing self-DNA to prevent the deposition, accumulation, or activity of pathogenic self proteins may be enhanced by use of viral vectors or other delivery systems that increase humoral responses against the encoded self-protein. In other embodiments, the DNA can be conjugated to solid supports including gold particles, polysaccharide-based supports, or other particles or beads that can be injected, inhaled, or delivered by particle bombardment (ballistic delivery).

Methods for delivering nucleic acid preparations are known in the art. See, e.g., U.S. Pat. Nos. 5,399,346, 5,580, 859, 5,589,466. A number of viral based systems have been developed for transfer into mammalian cells. For example, retroviral systems have been described (U.S. Pat. No. 5,219, 740; Miller et al., Biotechniques 7:980-990, 1989; Miller, A. D., Human Gene Therapy 1:5-14, 1990; Scarpa et al., Virology 180:849-852, 1991; Burns et al., Proc. Natl. Acad. Sci. USA 90:8033-8037, 1993; and, Boris-Lawrie and Temin, Cur. Opin. Genet. Develop. 3:102-109, 1993). A number of adenovirus vectors have also been described, see e.g., (Haj-Ahmad et al., J. Virol. 57:267-274, 1986; Bett et al., J. Virol. 67:5911-5921, 1993; Mittereder et al., Human Gene Therapy 5:717-729, 1994; Seth et al., J. Virol. 68:933-940, 1994; Barr et al., Gene Therapy 1:51-58, 1994; Berkner, K. L., Bio Techniques 6:616-629, 1988; and, Rich et al., Human Gene Therapy 4:461-476, 1993). Adeno-associated virus (AAV) vector 'systems have also been developed for nucleic acid delivery. AAV vectors can be readily constructed using techniques well known in the art. See, e.g., U.S. Pat. Nos. 5,173, 414 and 5,139,941; International Publication Nos. WO 92/01070 and WO 93/03769; Lebkowski et al., Molec. Cell. Biol. 8:3988-3996, 1988; Vincent et al., Vaccines 90 (Cold Spring Harbor Laboratory Press) 1990; Carter, B. J., Current Opinion in Biotechnology 3:533-539, 1992; Muzyczka, N., Current Topics in Microbiol. And Immunol. 158:97-129, 1992; Kotin, R. M., Human Gene Therapy 5:793-801, 1994; Shelling et al., Gene Therapy 1:165-169, 1994; and, Zhou et al., J. Exp. Med. 179:1867-1875, 1994).

The polynucleotide of this invention can also be delivered without a viral vector. For example, the molecule can be packaged in liposomes prior to delivery to the subject. Lipid encapsulation is generally accomplished using liposomes which are able to stably bind or entrap and retain nucleic acid. For a review of the use of liposomes as carriers for delivery of nucleic acids, see, (Hug et al., Biochim. Biophys. Acta. 1097: 1-17, 1991; Straubinger et al., in Methods of Enzymology, Vol. 101, pp. 512-527, 1983).

"Treating," "treatment," or "therapy" of a disease or disorder shall mean slowing, stopping or reversing the disease's progression, as evidenced by decreasing, cessation or elimination of either clinical or diagnostic symptoms, by administration of a polynucleotide encoding a self-protein(s), -polypeptide(s) or -peptide(s) either alone or in combination with another compound as described herein. "Treating," "treatment," or "therapy" also means a decrease in the severity of symptoms in an acute or chronic disease or disorder or a decrease in the relapse rate as for example in the case of a relapsing or remitting disease course. In the preferred embodiment, treating a disease means reversing or stopping the disease's progression, ideally to the point of eliminating the disease itself. As used herein, ameliorating a disease and treating a disease are equivalent.

"Preventing," "prophylaxis" or "prevention" of a disease or disorder as used in the context of this invention refers to the administration of a polynucleotide encoding a self-protein(s), -polypeptide(s), or -peptide(s) either alone or in combination with another compound as described herein, to prevent the occurrence or onset of a disease or disorder or some or all of the symptoms of a disease or disorder or to lessen the likelihood of the onset of a disease or disorder.

"Therapeutically effective amounts" of the self-vector comprising polynucleotide encoding one or more self-protein(s), -polypeptide(s) or -peptide(s) is administered in accord with the teaching of this invention and will be sufficient to treat or prevent the disease as for example by ameliorating or eliminating symptoms and/or the cause of the disease. For example, therapeutically effective amounts fall within broad-range(s) and are determined through clinical trials and for a particular patient is determined based upon factors known to the ordinarily skilled clinician including the severity of the disease, weight of the patient, age and other factors. Therapeutically effective amounts of self-vector are in the range of about 0.001 micrograms to about 1 gram. A preferred therapeutic amount of self-vector is in the range of about 10 micrograms to about 5 milligrams. A most preferred therapeutic amount of self-vector is in the range of about 0.025 mg to 5 mg. Polynucleotide therapy is delivered monthly for 6-12 months, and then every 3-12 months as a maintenance dose. Alternative treatment regimens may be developed and may range from daily, to weekly, to every other month, to yearly, to a one-time administration depending upon the severity of the disease, the age of the patient, the self-protein(s), -polypeptide(s) or -peptide(s) being administered and such other factors as would be considered by the ordinary treating physician.

In one embodiment the polynucleotide is delivered by intramuscular injection. In another embodiment the polynucleotide is delivered intranasally, orally, subcutaneously, intradermally, intravenously, mucosally, impressed through the skin, or attached to gold particles delivered to or through the dermis (see e.g. WO 97/46253). Alternatively, nucleic acid can be delivered into skin cells by topical application with or without liposomes or charged lipids (see e.g. U.S. Pat. No. 6,087,341). Yet another alternative is to deliver the nucleic acid as an inhaled agent. The polynucleotide is formulated in phosphate buffered saline with physiologic levels of calcium (0.9 mM). Alternatively the polynucleotide is formulated in solutions containing higher quantities of Ca++, between 1 mM and 2M. The polynucleotide may be formulated with other cations such as zinc, aluminum, and others. Alternatively, or in addition, the polynucleotide may be formulated either with a cationic polymer, cationic liposome-forming compounds, or in non-cationic liposomes. Examples of cationic liposomes for DNA delivery include liposomes generated using 1,2-bis(oleoyloxy)-3-(trimethylammionio) propane (DOTAP) and other such molecules.

Prior to delivery of the polynucleotide, the delivery site can be preconditioned by treatment with bupivicane, cardiotoxin or another agent that may enhance the delivery of subsequent polynucleotide therapy. Such preconditioning regimens are generally delivered 12 to 96 hours prior to delivery of therapeutic polynucleotide, more frequently 24 to 48 hours prior to delivery of the therapeutic DNA. Alternatively, no preconditioning treatment is given prior to DNA therapy.

In addition to the self-vector encoding self-protein(s), -polypeptide(s), or -peptide(s) an adjuvant for modulating the immune response consisting of CpG oligonucleotides may be co-administered in order to enhance the immune response. CpG oligonucleotides have been shown to enhance the antibody response of DNA vaccinations (Krieg et al., Nature 374:546-9, 1995). The CpG oligonucleotides will consist of a purified oligonucleotide of a backbone that is resistant to degradation in vivo such as a phosphorothioated backbone. The specific sequence contained within the oligonucleotide will be purine-purine-C-G-pyrimidine-pyrimidine or purine-pyrimidine-C-G-pyrimidine-pyrimidine. All of these constructs will be administered in a manner such that an immune response is generated against the encoded self-protein, -polypeptide(s) or -peptide(s). The immune response, typically an antibody response, will affect the non-physiological action or process associated with the self-protein, -polypepetide, or -peptide.

The self-vector comprising a polynucleotide encoding the self-protein(s), -polypeptide(s), or -peptide(s) can be administered in combination with other substances, such as pharmacological agents, adjuvants, cytokines, or in conjunction with delivery of vectors encoding cytokines. Furthermore, to avoid the possibility of eliciting unwanted anti-self cytokine responses when using cytokine codelivery, chemical immunodulatory agents such as the active form of vitamin D3 can also be used. In this regard, 1,25-dihydroxy vitamin D3 has been shown to exert an adjuvant effect via intramuscular DNA immunization.

Polynucleotide sequences coding for proteins, polypeptides or peptides known to stimulate, modify, or modulate a host's immune response, such as cytokines, can be coadministered with the self vector comprising a polynucleotide encoding the self-protein(s), -polypeptide(s), or -peptide(s). Thus, genes encoding one or more of the various cytokines (or functional fragments thereof), such as the interleukins, interferons, and colony stimulating factors, may be used in the instant invention. The gene sequences for a number of these substances are known. For example, the gene encoding IL-4 and IL-10 can be coadministered with the self vector comprising a polynucleotide encoding the self-protein(s), -polypeptide(s), or -peptide(s). Thus, in one embodiment of the invention, delivery of a self vector comprising a polynucleotide encoding the self-protein(s), -polypeptide(s), or -peptide(s) is coupled with coadministration of one or more of the following immunological response modifiers: IL-4; IL-10; IL-13 and IFN-γ.

Nucleotide sequences selected for use in the present invention can be derived from known sources, for example, by isolating the nucleic acid from cells containing a desired gene or nucleotide sequence using standard techniques. Similarly, the nucleotide sequences can be generated synthetically using standard modes of polynucleotide synthesis that are well known in the art. See, e.g., (Edge et al., Nature 292:756 1981); (Nambair et al., Science 223:1299 1984); (Jay et al., J. Biol. Chem. 259:6311 1984). Generally, synthetic oligonucleotides can be prepared by either the phosphotriester method as described by (Edge et al., (supra) and (Duckworth et al., Nucleic Acids Res. 9:1691 1981), or the phosphoramidite method as described by (Beaucage et al., Tet. Letts. 22:1859 1981), and (Matteucci et al., J. Am. Chem. Soc. 103:3185 1981).

Synthetic oligonucleotides can also be prepared using commercially available automated oligonucleotide synthesizers. The nucleotide sequences can thus be designed with appropriate codons for a particular amino acid sequence. In general, one will select preferred codons for expression in the intended host. The complete sequence is assembled from overlapping oligonucleotides prepared by standard methods and assembled into a complete coding sequence. See, e.g., Edge et al. (supra); Nambair et al. (supra) and Jay et al. (supra).

Another method for obtaining nucleic acid sequences for use herein is by recombinant means. Thus, a desired nucleotide sequence can be excised from a plasmid carrying the nucleic acid using standard restriction enzymes and procedures. Site specific DNA cleavage is performed by treating with the suitable restriction enzymes and procedures. Site specific DNA cleavage is performed by treating with the suitable restriction enzyme (or enzymes) under conditions which are generally understood in the art, and the particulars of which are specified by manufacturers of commercially available restriction enzymes. If desired, size separation of the cleaved fragments may be performed by polyacrylamide gel or agarose gel electrophoreses using standard techniques.

Yet another convenient method for isolating specific nucleic acid molecules is by the polymerase chain reaction (PCR). (Mullis et al., Methods Enzymol. 155:335-350 1987).

The following examples are specific embodiments for carrying out the present invention. The examples are offered for illustrative purposes only, and are not intended to limit the scope of the present invention in any way.

EXAMPLE 1

Polynucleotide Therapy Comprising Administration of DNA Encoding the Self-Protein PLP for Prevention of an Animal Model of Multiple Sclerosis PLP self-vector. A polynucleotide encoding an epitope of the PLP self-protein was constructed by annealing two oligonucleotides with a 16 mer overlapping complementary sequence (underlined), and extending with DNA polymerase and dNTPs: PLP (139-151):

5'-CTCGAGACCATGCATTGTTTGGGA<u>AAATGGCTAGGACAT</u>CCCGACA
AGTTTTCTAGATAGCTA-3' (SEQ ID NO:2);

PLP (139-151) L144/R147:

5'CTCGAGACCATGCATTGTTTGGGA<u>AAACTACTAGGACGC</u>CCCGACAA
GTTTTCTAGATAGCTA-3' (SEQ ID NO:3).

These oligonucleotide duplexes were designed to incorporate Xho I and Xba I restriction sites. The products were cloned into the multiple cloning region of pTARGET Vector (Promega, Madison, Wis., a mammalian expression vector driven by the CMV promoter. Positive clones were identified by color screening and correct orientation of the inserts was confirmed by DNA automatic sequencing. Purification of the plasmid DNA was done by Wizard plus Maxipreps (Promega) according to manufacturer instructions.

Polynucleotide therapy protocol. Experimental animals were injected in the left quadraceps with 0.1 ml of 0.25% bupivacaine-HCl (Sigma, St. Louis, Mo.) in PBS. Two and ten days later, mice were injected with 0.05 ml of plasmid DNA (1 mg/ml in PBS), in the same muscle.

EAE induction. PLP139-151 peptide was dissolved in PBS to a concentration of 2 mg/ml and emulsified with an equal volume of Incomplete Freund's Adjuvant supplemented with 4 mg/ml heat-killed *Mycobacterium tuberculosis* H37Ra (Difco Laboratories, Detroit, Mich.). Mice were injected subcutaneously with 0.1 ml of the peptide emulsion and, on the same day and 48 h later, intravenously with 0.1 ml of 4 µg/ml *Bordetella pertussis* toxin in PBS. Experimental animals were scored as follows: 0=no clinical disease; 1=tail weakness or paralysis; 2=hind limb weakness; 3=hind limb paralysis; 4=forelimb weakness or paralysis; 5=moribund or dead animal.

To determine whether injection of DNA encoding PLP sequences is effective in protecting mice from EAE induction, the PLP139-151 self-vector was injected, intramuscularly, twice, at one week intervals. Ten days after the last injection, mice were challenged with the PLP139-151 peptide emulsified in CFA. Amelioration of acute clinical disease is observed in the animals treated with the PLP139-151 self-vector, as compared with the control plasmid group. Onset of disease was delayed compared to the control plasmid group (11.5±0.5 days, p<0.008), mean peak disease severity was reduced (p<0.005), and mean disease score was reduced (p<0.0005). In addition, other groups were injected with either a) a self-vector comprising a polynucleotide encoding the altered peptide ligand PLP p139-151 (W144>L, H147>R), b) a self-vector comprising a polynucleotide encoding the PLP epitope p178-191. Onset of disease was delayed (11.6±0.5 days, p<0.009) and mean peak disease score was reduced (p<0.02) with the self-vector encoding the altered self-peptide ligand (W144, H147). Also, onset of disease was delayed (11.5±0.4 days, p<0.003), mean peak disease severity was reduced (p<0.007), and mean disease score was reduced (p<0.0001) with the self-vector comprising the polynucleotide encoding the PLP self-peptide p178-191.

Figure 1B:
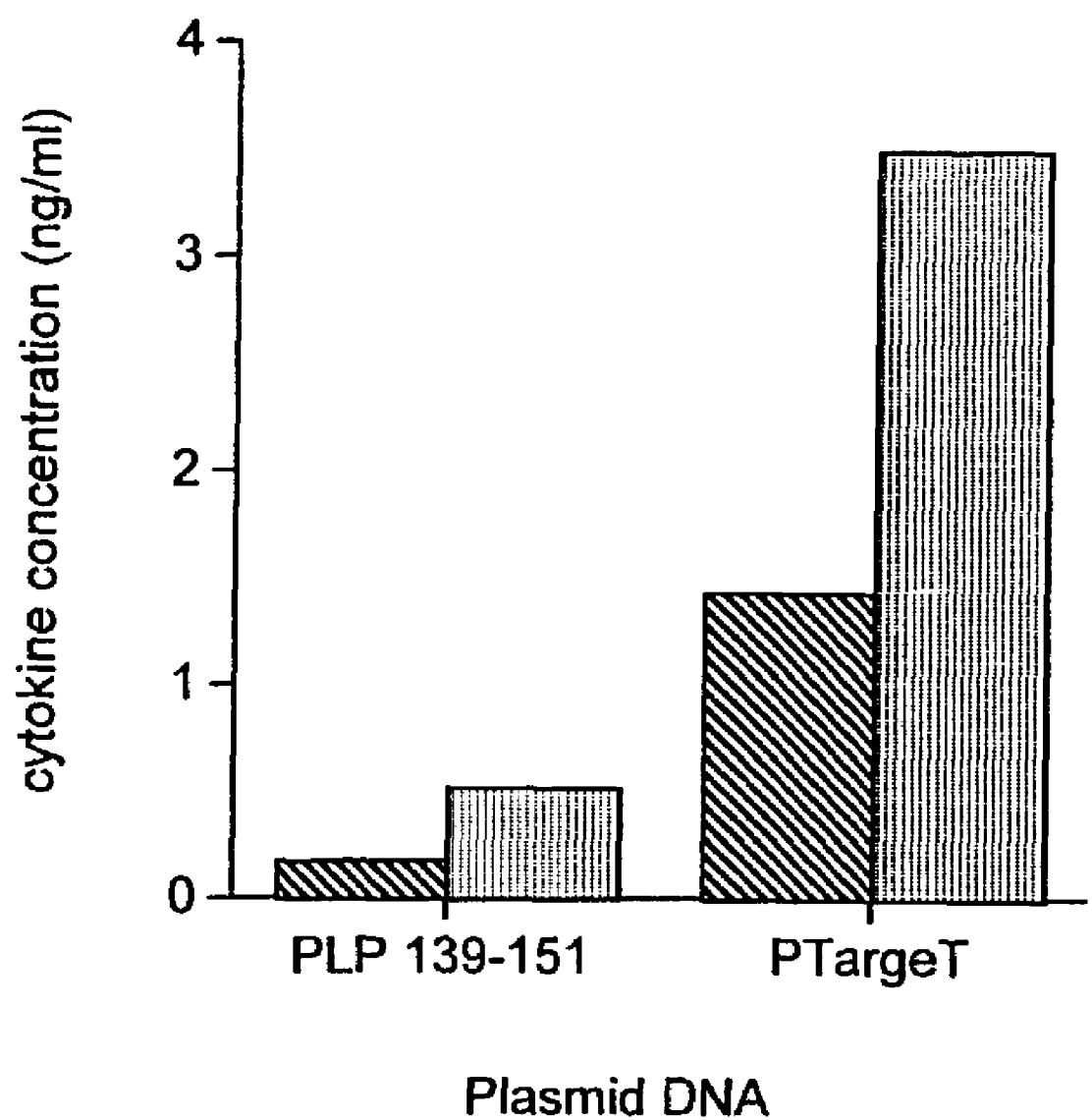
FIG. 1B. Cytokine levels are reduced in LNC from DNA immunized animals based on ELISA analysis. After the acute phase of EAE, LNC from groups of five animals vaccinated with either plasmid DNA coding for the PLP139-151 or vector alone (pTarget), were stimulated in vitro with the immunizing peptide PLP139-151. Levels of γ-interferon (striped bars) or IL-2 (dotted bars) were tested by ELISA in supernatants and compared to known standard controls. Results are expressed in ng/ml.
Figure 1C:
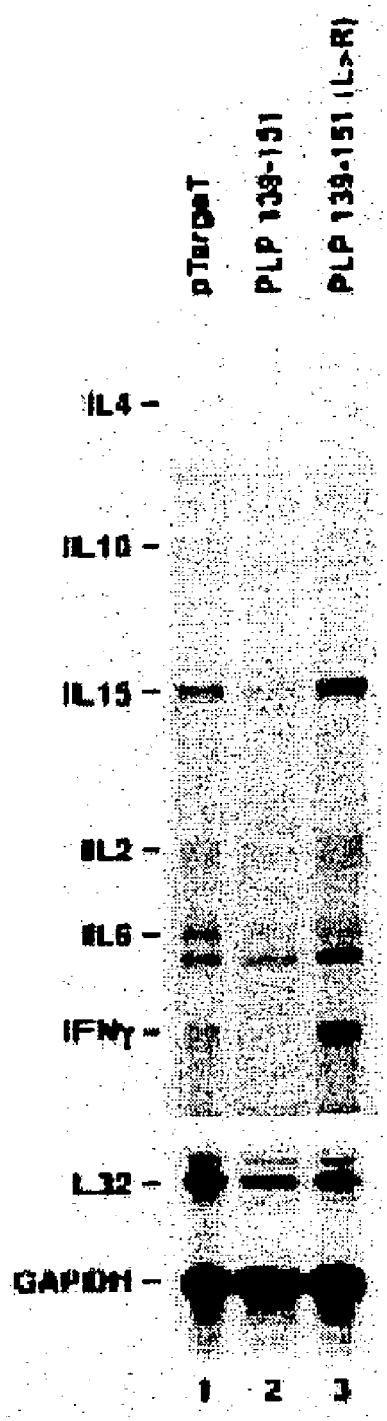
FIG. 1C. Cytokine levels are reduced in LNC from DNA immunized animals based on RNase Protection Assays. For cytokine mRNA detection, RNA samples from brains of experimental animals were tested using the Multi-Probe RNase Protection Assay and reactions were analyzed by 5% polyacrylamide gel electrophoresis. The gel was dried at the end of the run and exposed to x-ray film.

Mice, injected with DNA and further challenged with the encephalitogenic peptide PLP139-151, were sacrificed after resolution of the acute phase of the clinical disease. Draining LNC were restimulated in vitro with the PLP139-151 self-peptide and tested for their proliferative responses and cytokine production. FIG. 1A shows that LNC from mice injected with DNA coding for the PLP139-151 self-peptide had lower proliferative responses when compared with the LNC from control animals (p<0.01). FIG. 1(B) shows that, when stimulated with the PLP139-151, LNC from mice treated with the self-vector containing DNA coding for the PLP139-151 self-peptide secrete lower levels of IL-2 and γ-interferon in comparison with control groups. A ribonuclease protection assay on mRNA isolated from brain tissue was used to evaluate the levels of cytokine mRNA transcripts in inflamed brain. FIG. 1(C) reveals a reduction in mRNA levels of γ-interferon and IL-15 in mice treated with the self-vector comprising DNA encoding the PLP139-151 self-peptide. Therefore, a correlation between low incidence of clinical disease, reduced cellular responses, and low levels of IL-2, IL-15 and γ-interferon is evident in the PLP139-151 DNA treated mice. The relative expression levels of cytokine mRNA's bands shown in FIG. 1(C) were measured by densitometry. In order to correct for loading differences, the values were normalized according to the level of expression of the housekeeping gene, GAPDH, within each sample. Densitometric analysis confirmed reduction of expression level of the tested cytokines in brains of mice treated with the self-vector containing DNA encoding the PLP139-151 self-peptide compared to pTargeT and a self-vector containing DNA encoding PLP139-151 (L/R) self-peptide.

EXAMPLE 2

Polynucleotide Therapy Comprising Administration of DNA Encoding Multiple Self-Proteins for Treatment of an Animal Model of Multiple Sclerosis The same methodology described in example 1 was used to demonstrate that self-vector comprising DNA encoding four major myelin self-proteins, MBP, MOG, MAG, and PLP, was even more effective than DNA encoding a single self-peptide at treating established, on-going, relapsing EAE, the most representative animal model for human MS (Tables 5 and 6).

TABLE 5

Polynucleotide Therapy Comprising DNA Encoding Multiple Myelin Self-Proteins Treats Established On-Going EAE

|  | MOG/MBP/MAG/PLP DNA (Multiple Self-Proteins) | DNA Vector | PBS |
|---|---|---|---|
| # SJL/J mice (induced with PLPp139-151 in CFA) | 16 | 16 | 17 |
| Exacerbation rate | 1.6 | 3.9 | 2.9 |
| p value (student's T test; cocktail vs. pTarget or PBS) |  | <0.0001 | <0.0064 |

TABLE 5-continued

Polynucleotide Therapy Comprising DNA Encoding Multiple Myelin Self-Proteins Treats Established On-Going EAE

|  | MOG/MBP/<br>MAG/PLP DNA<br>(Multiple Self-Proteins) | DNA Vector | PBS |
|---|---|---|---|
| #/% animals with ≦ 1 relapse | 9/56% | 1/6.2% | 4/23% |

[1] The self-vector containing DNA encoding multiple self-proteins was administered to mice intramuscularly on a once per week basis at a dose of 50 μg of each of the four self-vectors encoding MBP, MOG, MAG, and PLP. Treatment was begun after recovery from the initial acute onset of EAE (e.g. after recovery from first episode of clinical paralysis following disease induction). The exacerbation rate indicates the number of clinical paralytic relapses occurring by day 87. p value calculated using Student's two-tailed unpaired t test.

EXAMPLE 3

Polynucleotide Therapy Comprising Administration of DNA Encoding Self-Peptide or Self-Proteins Plus DNA Encoding Cytokine for Treatment of an Animal Model of Multiple Sclerosis The methods described in example 1 were followed with the modification that the self-vector encoded a PLP self-peptide or multiple myelin proteins. DNA expression constructs encoding the cytokine IL-4 was concomitantly administered. DNA therapy by administration of a self-vector encoding both myelin self-peptide or myelin self-proteins in combination with DNA encoding the cytokine IL-4 further enhanced the protective effects (Table 6).

TABLE 6

Co-Treatment With DNA Encoding Self-Peptide or Self-Proteins Plus DNA Encoding And IL-4 Enhances The Therapeutic Effect Of DNA Therapy In Treating Established On-Going EAE.

| DNA Tolerizing Therapy | n | Mean Relapse Rate | p Value Compared To Multiple Self-Peptide/IL-4 |
|---|---|---|---|
| vehicle | 20 | 2.45 | 0.0018 |
| IL-4 | 14 | 2.93 | 0.0003 |
| PLP139-151 + IL-4 | 17 | 1.94 | 0.0158 |
| Multiple Self-Proteins (MBP, MAG, MOG, PLP) | 18 | 1.44 | 0.1714 |
| Multiple self-peptide + IL-4 | 17 | 0.94 | — |

[1] The DNA therapies were administered to mice intramuscularly on a once per week basis at a dose of 25 μg of each of four DNA plasmids encoding MBP, MOG, MAG, and PLP. All other DNA was given at a dose of 50 μg of plasmid per animal on a once weekly basis. Treatment was begun after recovery from the initial acute onset of EAE (e.g. after recovery from first episode of clinical paralysis following disease induction). Clinical relapses were counted to day 81. p value calculated using Student's two-tailed unpaired t test.

EXAMPLE 4

Polynucleotide Therapy Comprising Administration of DNA Encoding Self-Protein(s), -Polypeptide(s) and -Peptide(s) to Treat Human Multiple Sclerosis Polynucleotide therapy to treat human multiple sclerosis is carried out as follows. A self-vector is constructed comprising the cytomegalovirus or another effective transcriptional promoter; a polyadenylation signal derived from the SV40 large T antigen, bovine growth hormone, or another effective polyadenylation signal sequence known to the ordinarily skilled artisan; and, a kanamycin or other FDA-acceptable resistance gene to enable efficient growth of the plasmid.

DNA sequences encoding one or more of the human myelin self-proteins were cloned into the DNA self-vector. DNA encoding those myelin self-proteins targeted by the autoimmune response in MS patients including myelin basic protein (MBP), proteolipid protein (PLP), myelin-associated oligodendrocytic basic protein (MOBP) is cloned into the self-vector. Selection of a particular autoantigen for inclusion in polynucleotide therapy is based on various factors using the teaching of this invention and includes such factors as the presence of pathogenic autoantibodies in a subject. In one embodiment each myelin self-protein is encoded in a separate or distinct self-plasmid. In another embodiment, DNA encoding several myelin self-proteins are encoded sequentially in a single self-plasmid utilizing internal ribosomal re-entry sequences (IRESs) or other methods to express multiple proteins from a single plasmid DNA. The DNA expression self-plasmids encoding the myelin proteins were prepared and isolated using commonly available techniques for isolation of plasmid DNA such as those commercially available from Qiagen Corporation. The DNA was purified free of bacterial endotoxin for delivery to humans as a therapeutic agent. In one embodiment self-vector DNA encoding only MBP is administered to treat patients with multiple sclerosis. In another embodiment multiple self-plasmids encoding two or more myelin self-protein(s), -polypeptide(s) or -peptide(s) is administered. Therapeutically effective amounts of the self-vector comprising polynucleotide encoding one or more self-protein(s), -polypeptide(s) or -peptide(s) is administered in accord with the teaching of this invention. For example, therapeutically effective amounts of self-vector are in the range of about 0.001 micrograms to about 1 gram. A preferred therapeutic amount of self-vector is in the range of about 10 micrograms to about 5 milligrams. A most preferred therapeutic amount of self-vector is in the range of about 0.025 mg to 5 mg. The polynucleotide therapy is delivered monthly for 6-12 months, and then every 3-12 months as a maintenance dose. Alternative treatment regimens may be developed and may range from daily, to weekly, to every other month, to yearly, to a one-time administration depending upon the severity of the disease, the age of the patient, the self-protein(s), -polypeptide(s) or -peptide(s) being administered and such other factors as would be considered by the ordinary treating physician.

In one embodiment the DNA is delivered by intramuscular injection. In another embodiment the DNA is delivered as an inhaled agent, intranasally, orally, subcutaneously, intradermally, intravenously, impressed through the skin, or attached to particles or beads delivered to or through the dermis. Such particles or beads can be gold, other metals, polystyrene, or other particles. In one embodiment, the DNA is formulated in phosphate buffered saline with physiologic levels of calcium (0.9 mM). Alternatively the DNA is formulated in solutions containing higher quantities of Ca++, between 1 mM and 2M. In another embodiment, the DNA is formulated with other cations such as zinc, aluminum, and others. The DNA could also be formulated with a cationic polymer, with a cationic liposome, or in other liposomes. The DNA could also be delivered encoded in a viral vector, viral particle, or bacterium.

Human MS patients treated with the disclosed DNA therapy will be monitored for disease activity based on the number of clinical relapses and MRI monitoring for the number of new gadolinium-enhancing lesions and the volume of the enhancing lesions.

EXAMPLE 5

Polynucleotide Therapy Comprising Administration of DNA Encoding the Self-Peptide of the Insulin β chain for Prevention of Insulin Dependent Diabetes Mellitus NOD mice develop spontaneous autoimmune diabetes, and share many clinical, immunological, and histopathological features with human IDDM. A self-vector comprising a DNA encoding the self-peptide of amino acids 9-23 of the insulin B chain, the immunodominant epitope of insulin, was administered to NOD mice. The control was a vector comprising DNA encoding a corresponding peptide on the A chain of insulin. Overlapping oligonucleotide primers encoding the self-peptide were inserted into an expression self-cassette, pcDNA. Treatment with self-vector encoding the self-peptide insulin B (9-23) (insB-pcDNA) effectively protected animals from developing diabetes. Disease onset occurred at a markedly decreased rate, and significantly fewer animals developed disease at all. InsB-pcDNA induced a shift in the cytokine expression by insulin B-specific cells in the pancreas: IL-10 and IFN-γ expression was downregulated in pancreatic lymph node cells cultured with insulin B (9-23) peptide. The nucleotide sequence of the insulin A (+) strand is:

5'CCGGAATTCGCCATGTGCACGTCAATCTGTTCACTGTACCAGCTAGA
GAACTACTGCAACTAGTCTAQGAGC-3' (SEQ ID NO:4);

the sequence of the insulin B (+) strand is:

5'-CCGGAATTCGCCATGAGCCACCTAGTAGAAGCACTATACCTCGTAT
GCGGCGAACGAGGTTAGTCTAGAGC-3' (SEQ ID NO:5).

These polynucleotides were designed to incorporate EcoRI and XbaI restriction sites for cloning. The products were cloned into the multiple cloning region of expression self-cassette pcDNA3.1+ (Invitrogen, Carlsbad, Calif.). Purification of the self-plasmid DNA was carried out using Qiagen Endo-free Mega-prep kits (Qiagen, Valencia, Calif.).

Three- to four-week-old female NOD mice Were purchased from Taconic Farms (Germantown, N.Y.). Experimental animals were injected at 3 to 4 weeks of-age in the quadricep with 0.1 ml of 0.25% bupivicaine-HCL (Sigma, St. Louis, Mo.) in PBS (0.05 ml per quadricep). Two days following, mice were injected with 0.05 ml of plasmid DNA at 1.0 mg/ml in each quadricep. The plasmid DNA was injected two more times at ten-day intervals. Mice were tested weekly for glucosuria by Chemstrip (Boehringer Mannheim Co., Indianapolis, Ind.), and diabetes was confirmed by plasma glucose measurement using the One Touch II meter (Johnson & Johnson, Milpitas, Calif.). Animals having repeated plasma glucose levels greater than 250 mg/dl were considered diabetic. The pancreata were removed from experimental and control animals, fixed in 10% formaldehyde, and embedded in paraffin. Thin sections at three levels, 50 μm apart, were cut for staining with hematoxylin and eosin. The severity of infiltration was assessed by light microscopy. Three and five animals from each group were analyzed for two individual experiments, respectively. At least 25 islets were examined per pancreas.

Figure 2:
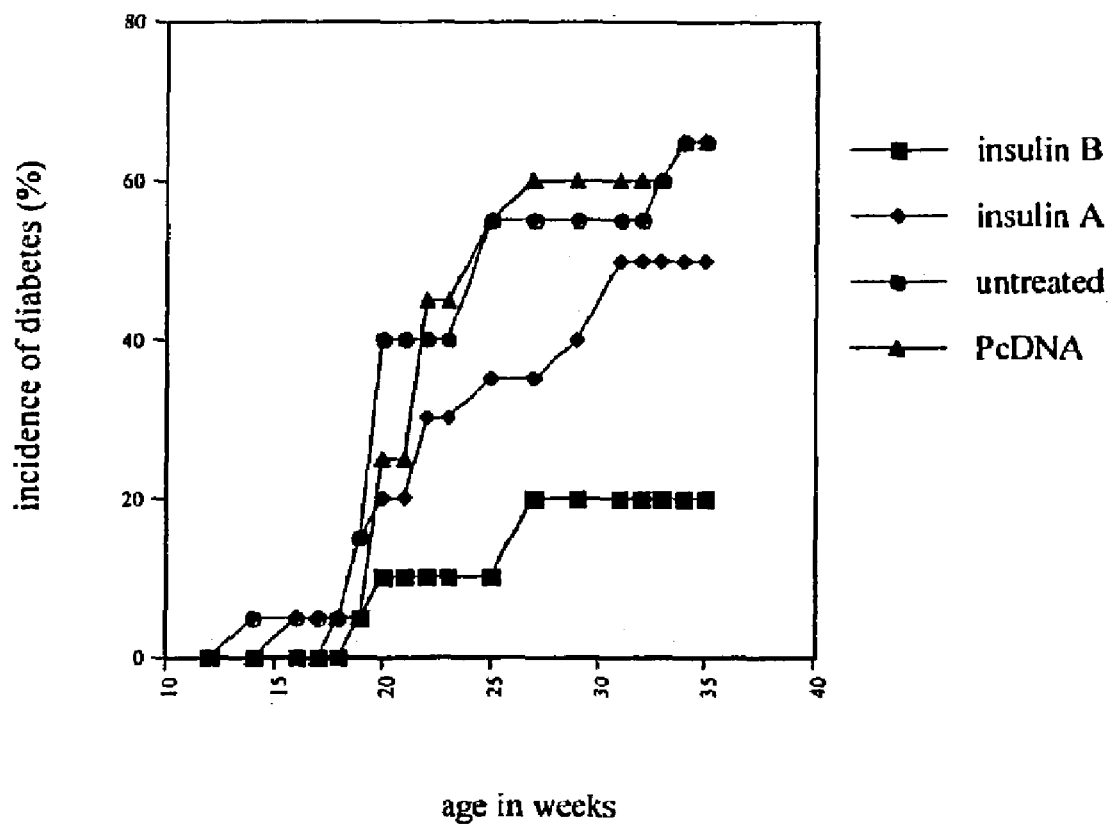
FIG. 2. DNA encoding a peptide of the self-protein insulin prevents development of diabetes in NOD mice. Groups of 4 week-old pre-diabetic NOD mice were treated with a DNA self-vector encoding the immunodominant peptide of the insulin B chain (residues 9-23) (insulin B), an insulin A chain peptide (insulin A), vector alone (pcDNA), or no treatment.

Polynucleotide therapy comprising the administration of a self-vector encoding the self-peptide insulin B (9-23) was carried out in the NOD mouse model. Groups of 10 4-week-old NOD mice were injected in the quadricep muscles with 50 μl of 0.25% bupivicaine followed 48 hours later by injection of 100 μg self-plasmid DNA. Self-plasmid DNA was injected two more times at 10-day intervals (50 μg per quadricep). Mice were monitored for diabetes, as determined by glucosuria and hyperglycemia, weekly for >30 weeks. Results represent two independent experiments. In the untreated and plasmid control (pcDNA) injected groups, 70% of the mice developed diabetes by 34 weeks of age (FIG. 2). In the insB-pcDNA injected group, however, only 20% developed diabetes by the same age (p=0.02 by $X^2$ analysis). Furthermore, the onset of disease was markedly delayed in this group as well, from <14 weeks for the first animal to become diabetic in the untreated group, to >23 weeks for the insB-pcDNA treated group. The diabetes incidence rate for the pcDNA and untreated control groups was 3 times the rate for the insB-pcDNA group (0.035 and 0.036 for the pcDNA and untreated groups,. respectively, compared to 0.012 for insB-pcDNA group.)

In the case of the self-peptide (InsB-pcDNA) treated NOD mice insulitis was observed even though the animals showed no clinical signs of diabetes. Pancreata were removed from immunized and control animals at 7 weeks of age, a time at which the initial infiltration of the islets was clearly visible by histological staining of NOD pancreata. A minimum of twenty-five islets for each of five animals in each group were scored for insulitis. Staining of pancreata from older (16-week-old) mice yielded similar results. Although animals injected with self-vector comprising DNA encoding the self-peptide showed no clinical signs of diabetes, infiltrate was visible at levels comparable to those in the sick control animals. Hence treatment with insulin DNA does not affect trafficking of lymphocytes to the islets of Langerhans.

Figure 3:
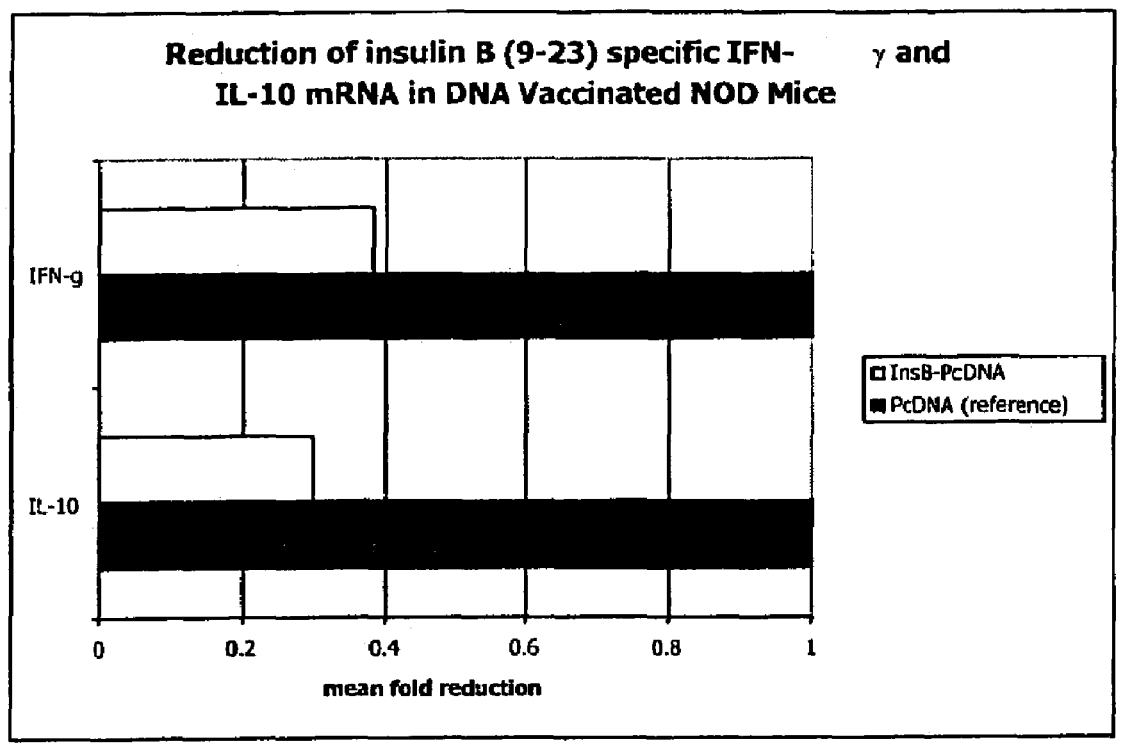
FIG. 3. Quantitative PCR measurement of cytokine expression in LNC from NOD mice. Quantitative PCR measurement of cytokine expression by pancreatic LNC from vaccinated NOD mice cultured with 10 μg/ml insulin B (9-23) peptide. Pancreatic LNC from NOD mice vaccinated twice at a ten-day interval with either pcDNA or InsB-pcDNA were harvested 5 days after the second injection. Cells were cultured in the presence of insulin B (9-23) peptide for 72 hours, then pelleted for quantitative PCR analysis of cytokine mRNA levels. pcDNA control vaccinated levels (solid bars) were used as a standard against which the insB-pcDNA vaccinated values (hatched bars) were compared.

Polynucleotide therapy with Insulin B (9-23) DNA induced an antigen-specific response in the pancreatic lymph nodes. In order to detect antigen-specific responses in vitro, we used quantitative PCR to assess levels of cytokine mRNA production (FIG. 3). In three independent experiments, groups of animals were injected twice with either the insB-pcDNA self-vector or the pcDNA control plasmid. Five days after the second injection, pancreatic lymph nodes were harvested and single-cell suspension plated with 10 μg/mL insulin B (9-23) peptide. After 72 hours the cells were pelleted, and subjected to quantitative PCR analysis for IL-4, TGF-β, IL-10, and IFN-γ message levels. Quantitative PCR comparison of cytokine message levels in pancreatic lymph node cells showed a significant reduction in IFN-γ and IL-10 levels in the insB-pcDNA treated animals compared to pcDNA-treated controls. IFN-γ levels from insB-pcDNA-treated lymph nodes were 38% that of pcDNA-treated lymph nodes (p<0.05) in response to insulin B peptide stimulation. Furthermore, IL-10 levels in InsB-pcDNA treated mice were 30% of pcDNA control levels (p<0.01). Changes in mRNA levels of IL-4 and TGF-β were not significant over the three experiments.

EXAMPLE 6

Polynucleotide Therapy Comprising Administration of DNA Encoding the Self-Polypeptide Insulin and Self-Proteins Glutamic Acid Decarboxylase and Tyrosine Phosphatase IA-2 for Treatment of Insulin Dependent Diabetes Mellitus NOD mice are treated with polynucleotide therapy comprising DNA encoding the whole pro-insulin polypepide along with DNA encoding glutamic acid decarboxylase (GAD) 65 kDa, and the islet tyrosine phosphatase IA-2. The cDNAs encoding proinsulin, GAD 65, and IA-2 were isolated and cloned into the expression self-cassette pTARGET vector. The DNA is purified using Qiagen Endo-free Mega-prep kits (Qiagen, Valencia, Calif.). NOD mice are injected at 3 to 4 weeks of age in the quadricep with 0.1 ml of 0.25% bupivicaine-HCL (Sigma, St. Louis, Mo.) in PBS (0.05 ml per quadricep). Two days following, mice are injected with 0.05 ml of each self-plasmid DNA at 1.0 mg/ml in phosphate buffered saline with 0.9 mM calcium in each quadricep. The plasmid DNA is injected two more times at ten-day intervals. Mice are tested weekly for glucosuria by Chemstrip (Boehringer Mannheim Co., Indianapolis, Ind.), and diabetes is confirmed by plasma glucose measurement using the One Touch II meter (Johnson & Johnson, Milpitas, Calif.). Animals having repeated plasma glucose levels greater than 250 mg/dl are considered diabetic.

EXAMPLE 7

Polynucleotide Therapy Comprising Administration of DNA Encoding the Self-Polypeptide Insulin and/or Self-Proteins Glutamic Acid Decarboxylase and Tyrosine Phosphatase IA-2 for Treating and Reversing Overt Hyperglycemia in Established Insulin Dependent Diabetes Mellitus NOD mice were identified to have overt clinical diabetes based on glucosuria detected using Chemstrip (Boehringer Mannheim Co., Indianapolis, Ind.) analysis of urine, with confirmation of diabetes by plasma glucose measurement using the One Touch II meter (Johnson & Johnson, Milpitas, Calif.). NOD mice with overt clinical diabetes were treated with polynucleotide therapy comprising DNA encoding the self-peptide insulin B (9-23) (insB-pcDNA) described in the example above. The sequence of the insulin B (+) strand is 5'-CCGGAATTCGCCATGAGCCACCTAGTA-GAAGCACTATACCTCGTATGCGGCGAAC-GAGGTTAGTCTAGAGC-3' (SEQ ID NO:5) and this polynucleotide was designed to incorporate EcoRI and XbaI restriction sites for cloning. The product was cloned into the multiple cloning region of expression self-cassette pcDNA3.1+ (Invitrogen; Carlsbad, Calif.). Purification of the self-plasmid DNA was carried out using Qiagen Endo-free Mega-prep kits (Qiagen, Valencia, Calif.). Treatment of mice with overt clinical diabetes based on glucosuria and elevated serum glucose with DNA encoding the self-peptide insulin B (9-23) (insB-PcDNA) reversed hyperglycemia and glucosuria, thereby reversing established diabetes. Treatment of animals with DNA encoding the self polypeptide insulin in combination with glutamic acid decarboxylase and tyrosine phosphatase is significantly increases the efficacy of DNA therapy for the treatment and reversal of established autoimmune diabetes.

EXAMPLE 8

Polynucleotide Therapy Comprising Administration of DNA Encoding Self-Proteins for Treatment of Human Insulin Dependent Diabetes Mellitus The self-plasmid DNA constructed in example 5 is modified for administration to humans and comprises DNA encoding the human islet cell self-proteins including the tyrosine phosphatase IA-2; glutamic acid decarboxylase (GAD) both the 65 kDa and 67 kDa forms; proinsulin; islet cell antigen 69 KDa (ICA69). The DNA are isolated using PCR and cloned into the expression self-cassette as described previously.

Therapeutically effective amounts of the self-vector comprising polynucleotide encoding one or more self-protein(s), -polypeptide(s) or -peptide(s) is administered in accord with the teaching of this invention. For example, therapeutically effective amounts of self-vector are in the range of about 0.001 micrograms to about 1 gram. A preferred therapeutic amount of self-vector is in the range of about 10 micrograms to about 5 milligrams. A most preferred therapeutic amount of self-vector is in the range of about 0.025 mg to about 5 mg. The DNA therapy is delivered monthly for 6-12 months, and then every 3-12 months as a maintenance dose. Alternative treatment regimens may be developed and may range from daily, to weekly, to every other month, to yearly, to a one-time administration depending upon the severity of the disease, the age of the patient, the self-protein(s), -polypeptide(s) or -peptide(s) being administered and such other factors as would be considered by the ordinary treating physician. In the preferred embodiment the DNA is delivered by intramuscular injection. Alternatively, the DNA self-vector is delivered as an inhaled agent, intranasally, orally, subcutaneously, intradermally, intravenously, impressed through the skin, and in the case of treatment of IDDM attached to gold particles delivered by gene gun to or through the dermis. The DNA is formulated in phosphate buffered saline with physiologic levels of calcium (0.9 mM). Alternatively the DNA is formulated in solutions containing higher quantities of Ca++, between 1 mM and 2M. The DNA is formulated with other cations such as zinc, aluminum, and others.

Human diabetes patients treated with the disclosed DNA therapy will be monitored for disease activity based on decreased requirement for exogenous insulin, alterations in serum autoantibody profiles, decrease in glycosuria, and decrease in diabetes complications such as cataracts, vascular insufficiency, arthropathy, and neuropathy.

EXAMPLE 9

Polynucleotide Therapy Comprising Administration of DNA Encoding the Self-Protein Type II Collagen for Prevention of Autoimmune Synovitis and Rheumatoid Arthritis RA arises from pathogenic T cells that evade mechanisms promoting self-tolerance. Collagen-induced arthritis (CIA) in mice is a model of T cell-mediated autoimmunity that shares many features with RA, including synovitis and bony erosions that histologically resemble those in RA. The relapsing model of CIA has clinical relapses and remissions of inflammatory erosive synovitis in a similar fashion to that observed in human RA patients (Malfait et al, Proc Natl Acad Sci USA, 97:9561-6, 2000). CIA is induced by injecting genetically susceptible strains of mice with type II collagen (CII) in complete Freund's adjuvant.

The cDNA encoding murine type II collagen was isolated using the polymerase chain reaction. Additional synovial self-proteins such as collagens type IV and IX, and heat shock protein 65 may be included in the polynucleotide therapy. DNA encoding the described peptides was obtained using oligonucleotide primers to amplify the relevant fragments of DNA by PCR from murine CII cDNA. An in frame methionine start of translation site as well as Xho I and Xba I restriction endonuclease sites was incorporated within the oligonucleotide primers. The PCR-generated DNA fragments were cloned into the Xho I and Xba I restriction endonuclease sites of the expression self-cassette pTARGET Vector (Promega, Madison, Wis.), a mammalian expression vector driven by the CMV promoter. The isolated clones were sequenced to confirm that the desired DNA sequence has been produced.

Male DBA/1LacJ (H-$2^q$) mice between 6-9 weeks of age at the start of the experiment are used. 100 μg of each of the purified self-plasmids comprising DNA encoding the synovial joint self proteins were injected intramuscularly into the tibialis anterior muscle 3 times at weekly intervals prior to induction of disease for the prevention of CIA experiments, or following onset of clinical CIA in the treatment of relapsing CIA experiments. After DNA treatment, mice were challenged intradermally at the base of the tail with 100 μg purified bovine CII protein in complete Freund's adjuvant (CFA) to induce acute CIA. The mice are followed daily for 12 weeks for clinical evidence of CIA based on the visual scoring system (Coligan et al., John Wiley and Sons, Inc 15.5.1-15.5.24, 1994): 0, no evidence of erythema and swelling; 1, erythema and mild swelling confined to the mid-foot (tarsals) or ankle joint; 2, erythema and mild swelling extending from the ankle to the mid-foot; 3, erythema and moderate swelling extending from the ankle to the metatarsal joints; and 4 erythema and severe swelling encompassing the ankle, foot and digits. The clinical score for each animal is the sum of the visual score for each of its four paws. Histologic analysis is performed on joints from mice that develop clinical arthritis. The first paw from the limb with the highest visual score is decalcified, sectioned, and stained with hematoxylin and eosin as previously described (Williams et al., Proc Natl Acad Sci U S A 91: 2762-2766, 1994). The stained sections are examined for lymphocytic infiltration, synovial hyperplasia and erosions as previously described (Williams et al., Proc Natl Acad Sci U S A 91: 2762-2766, 1994).

EXAMPLE 10

Polynucleotide Therapy Comprising Administration of DNA Encoding Self-Protein Type II Collagen for Treatment of Established Autoimmune Synovitis Animals with established ongoing CIA are treated with self-vector DNA encoding CII, BiP, and/or GP-39 to reverse established ongoing CIA. The mice are followed daily for 12 weeks for clinical evidence of CIA based on the visual scoring system (Coligan et al., John Wiley and Sons, Inc 15.5.1-15.5.24, 1994): Treatment with self DNA encoding CII, BiP, GP-39 and/or additional proteins present in synovial joints may reduce the severity of arthritis based on the visual scoring system.

EXAMPLE 11

Polynucleotide Therapy Comprising Administration of DNA Encoding Self Synovial Proteins for the Prevention of, or Treatment of, Human Rheumatoid Arthritis and other Autoimmune Diseases Targeting Joints The self-plasmid DNA constructed in the previous two examples is modified for administration to humans and comprises DNA encoding the human self-proteins, such as proteins expressed in synovial joints including type II collagen, BiP, gp39, collagen type IV, glucose-6-phosphate isomerase and/or fibrin. The DNA is isolated using PCR and cloned into the expression self-cassette as described previously. 100 μg of plasmid DNA is administered in phosphate buffered saline with calcium intramuscularly on a monthly basis. It is also possible to administer the DNA in different dosing regimens, formulated in different buffers, or via different routes of administration as discussed above in Example 1.

Humans with new-onset or ongoing RA, diagnosed based on the American College of Rheumatology Criteria (4/7 criteria required for diagnosis: (i) symmetrical polyarthritis, (ii) involvement of the MCPs, PIPs, or wrists, (iii) involvement of more than 3 different joint areas, (iv) joint erosions on X rays of hands or feet, (v) positive rheumatoid factor test, (iv) greater than 1 hour of morning stiffness, and (vii) nodules on extensor surfaces) are treated with self polynucleotides encoding type II collagen, BiP, gp39, collagen type IV, glucose-6-phosphate isomerase and/or fibrin. The efficacy of the DNA therapies for RA is monitored based on the fraction of patients with a reduction in their tender and swollen joint count by greater than 20% (an American College of Rheumatology 20% Response, ACR20), 50% (ACR50), and 70% (ACR70). Additional measures for human RA include inflammatory markers (including ESR and CRP) reduction in steroid usage, reduction in radiographic progression (including erosions and joint space narrowing) and improvement in disability status scores (such as the Health Assessment Questionnaire—HAQ). Changes in autoantibody titers and profiles will also be monitored. An identical approach will be used for related arthritides such as psoriatic arthritis, reactive arthritis, Reiter's syndrome, Ankylosing spondylitis, and polymyalgia rheumatica.

Recent studies have suggested that certain autoantibodies with high specificity for rheumatoid arthritis (e.g., BiP, anti-citrulline antibodies, anti-filaggrin antibodies) may precede the clinical diagnosis by months, or even years. This raises the possibility that patients could be identified prior to disease onset, and effectively treated using a preventative polynucleotide therapeutic. Healthy, asymptomatic patients will be screened for the presence of a diagnostic autoantibody, including but not limited to one of the serological tests described above. Patients with a positive test will be treated with a polynucleotide therapeutic as described above and in other examples, in an attempt to prevent disease onset and severity. Subsequent diagnosis and response will be monitored using the above criteria.

EXAMPLE 12

Polynucleotide Therapy Comprising Administration of DNA Encoding Uveal Self-Proteins for Prevention of Autoimmune Uveitis Experimental autoimmune uveitis (EAU) is a T cell-mediated autoimmune disease affecting the uvea and retina in mice, and shares many clinical, immunological, and histopathological features with human autoimmune uveitis. DNA encoding S-antigen and interphotoreceptor retinoid binding protein (IRBP) were isolated using PCR and cloned into the expression self-cassette pTARGET as described previously 100 μg of each of the purified self-plasmids is injected 3 times at weekly intervals into the tibialis anterior muscle of B10.IIIR mice prior to induction of EAU. The DNA therapy is initiated following injection at the site of administration with bupivicane, cardiotoxin, or another pre-conditioning agent, or without such an agent. After DNA treatment, B10.RIII mice are challenged for EAU with the immunodominant IRBP 161-80 peptide emulsified in complete Freund's adjuvant (CFA). The mice are followed for 8 weeks for clinical evidence of EAU based fundoscopic examination using a standard scoring system (Colligan et al): 0, no disease; 0.5 (Trace), 1-2 very small peripheral focal lesions, minimal vasculitis/vitritis; 1, mild vasculitis, <5 focal lesions, <1 linear lesion; 2, multiple (>5) chorioretinal lesions and/or infiltrations, severe vasculitis, <5 linear lesions; 3, pattern of linear lesions, large confluent lesions, subretinal neovascularization; 4, large retinal detachment, retinal atrophy. Groups of mice are periodically sacrificed and histologic analysis and scoring preformed on representative eyes.

EXAMPLE 13

Polynucleotide Therapy Comprising Administration of DNA Encoding Uveal Self-Proteins for Treating Established Autoimmune Uveitis DNA encoding S-antigen and interphotoreceptor retinoid binding protein (IRBP) is isolated using PCR and cloned into the expression self-cassette pTARGET as described previously. B10.RIII mice are induced to develop EAU with the immunodominant IRBP 161-80 peptide emulsified in complete Freund's adjuvant (CFA). Animals with established ongoing EAU can be effectively treated by periodic administration of 100 µg of each of the purified self-plasmids. The self polynucleotide can be administered weekly, or at another interval, into the tibialis anterior muscle of B10.IIIR mice following development of clinical EAU. Efficacy is demonstrated based on a 12-weeks period of clinical monitoring for disease activity of EAU based fundoscopic examination using a standard scoring system (Colligan et al).

EXAMPLE 14

Polynucleotide Therapy Comprising Administration of DNA Encoding Uveal Self-Proteins for Treating Human Autoimmune Uveitis Using PCR human S-antigen, interphotoreceptor retinoid binding protein (IRBP), rhodopsin, and recoverin are isolated and cloned into a DNA expression self-cassette as described in Example 1. The self-vector constructed in example 7 is modified to comprise the polynucleotide encoding one or more of the self-protein(s), -polypeptide(s) or -peptide(s) selected from the group consisting of human S-antigen, interphotoreceptor retinoid binding protein, rhodopsin and recovering. Therapeutically effective amounts of the self-vector comprising polynucleotide encoding one or more self-protein(s), -polypeptide(s) or -peptide(s) is administered in accord with the teaching of this invention. For example, therapeutically effective amounts of self-vector are in the range of about 0.001 micrograms to about 1 gram. A preferred therapeutic amount of self-vector is in the range of about 10 micrograms to about 5 milligrams. A most preferred therapeutic amount of self-vector is in the range of about 0.025 mg to about 5 mg. The DNA therapy is delivered monthly for 6-12 months, and then every 3-12 months as a maintenance dose. Alternative treatment regimens may be developed and may range from daily, to weekly, to every other month, to yearly, to a one-time administration depending upon the severity of the disease, the age of the patient, the self-protein(s), -polypeptide(s) or -peptide(s) being administered and such other factors as would be considered by the ordinary treating physician.

In a preferred embodiment the DNA is delivered by intramuscular injection. Alternatively, the DNA self-vector is delivered as an inhaled agent, intranasally, orally, subcutaneously, intradermally, intravenously, impressed through the skin, and in the case of treatment of autoimmune uveitis attached to gold particles delivered to or through the dermis. In another embodiment, the DNA is formulated in phosphate buffered saline with physiologic levels of calcium (0.9 mM). Alternatively the DNA can be formulated is solutions containing higher quantities of Ca++, between 1 mM and 2M. The DNA could be formulated with other cations such as zinc, aluminum, and others.

EXAMPLE 15

Polynucleotide Therapy Comprising Administration of DNA Encoding Mitochondrial Enzyme Self-Protein for Preventing Primary Biliary Cirrhosis The murine model of primary biliary cirrhosis (PBC) is experimental autoimmune cholangitis (EAC) and uses i.p. sensitization with mammalian pyruvate dehydrogenase complex (PDC) or with synthetic PDC peptides in female SJL/J mice (Jones, J Clin Pathol 53:813-21, 2000). Anti-mitochondrial antibodies were observed in many strains, but NSDC was observed in a single strain of mice (SJL/J), suggesting that additional response factors are required for the induction of IBEC damage. Mice are sensitized i.p. with purified bovine PDC (500 µg in 100 µL saline mixed 1:1 (v/v) in incomplete Freund's adjuvant (IFA) at a concentration of 10 mg/mL). All sensitizations are performed at 8-12 weeks of age. Tail vein bleeds are performed prior to antigen challenge and at 4, 8, 12, 16, 20 and 30 weeks post-sensitization. At the same intervals of time liver function tests including bilirubin, alkaline phosphatase, alanine amino transferase (ALT), and aspartate aminotransferase (AST) are performed. Animals (10 for each group) are sacrificed at 30 weeks post-sensitization. Liver histology is evaluated using haematoxylin & eosin stain and periodic acid Schiff. Bile duct abnormalities, necro-inflammatory changes in portal tracts and granulomatous infiltration are also examined.

DNA encoding PDC-E2 and -E3 is isolated using PCR and cloned into the expression self-cassette pTARGET (Promega, Madison, Wis.), amplified in E. coli and purified using an endotoxin-free plasmid purification kit (Qiagen™) according to the manufacturer's instructions as described previously. Polynucleotide therapy comprising DNA encoding self-protein(s) PDC-E2 and -E3 is administered to animals prior to inducing disease. Selection of the self-protein(s), polypeptide(s) or peptide(s) to be administered is determined based on a series of experiments as described previously and contains about 1 to 8 antigen self-protein(s), polypeptide(s) or peptide(s), preferably 2 to 6, and most preferably 3 to 5 antigens in total. A vector comprising DNA encoding a cytokine, such as IL-4, may be administered with the self-vector.

EXAMPLE 16

Polynucleotide Therapy Comprising Administration of DNA Encoding Mitochondrial Enzyme Self-Protein for Prevention pf Primary Biliary Cirrhosis, and Treatment of Established Primary Biliary Cirrhosis DNA encoding human PDC-E2 and -E3 is isolated using PCR and cloned into the expression self-cassette of a suitable mammalian expression vector, amplified in E. coli, and purified using an endotoxin-free plasmid purification method. Polynucleotide therapy comprising DNA encoding self-protein(s) PDC-E2 and -E3 is administered to humans with established PBC. A vector comprising DNA encoding a cytokine, such as IL-4, may be administered with the self-vector. The efficacy of the DNA therapy for PBCs in humans is determined by measuring serial liver function tests including bilirubin, alkaline phosphatase, alanine amino transferase (ALT), and aspartate aminotransferase (AST), as well as the delay in time to progression to liver failure. Following percutaneous liver, biopsy, liver histology is evaluated by haematoxylin & eosin stain and periodic acid Schiff. Bile duct abnormalities, necro-inflammatory changes in portal tracts and granulomatous infiltration are also examined for evidence of disease activity.

Patients with PBC, or at risk to develop PBC, can be efficiently diagnosed by identifying serum autoantibodies directed against mitochondrial proteins such as the pyruvate dehydrogenase complex. Asymptomatic human patients will be tested using available serlogic tests such as ELISA, Western blot, or protein array for the presence of diagnostic autoantibodies. Patients with a positive serological test will be treated prophylactically with polynucleotide therapy as described above to prevent disease onset. The efficacy of the DNA therapy for PBCs in humans is determined by measuring serial liver function tests including bilirubin, alkaline phosphatase, alanine amino transferase (ALT), and aspartate aminotransferase (AST), as well as the delay in time to progression to liver failure. Following percutaneous liver biopsy, liver histology is evaluated by haematoxylin & eosin stain and periodic acid Schiff. Bile duct abnormalities, necro-inflammatory changes in portal tracts and granulomatous infiltration are also examined for evidence of disease activity. Serum autoantibody profiles will also be analyzed.

EXAMPLE 17

Polynucleotide Therapy Comprising Administration of DNA Encoding Amyloid β Protein for Treating Alzheimer's Disease A self-vector comprising DNA encoding the human amyloid β (Aβ polypeptide is constructed. As described previously, the cassette has transcriptional and translational regulatory sequences for expression of the DNA in the recipient cells.

Figure 4:
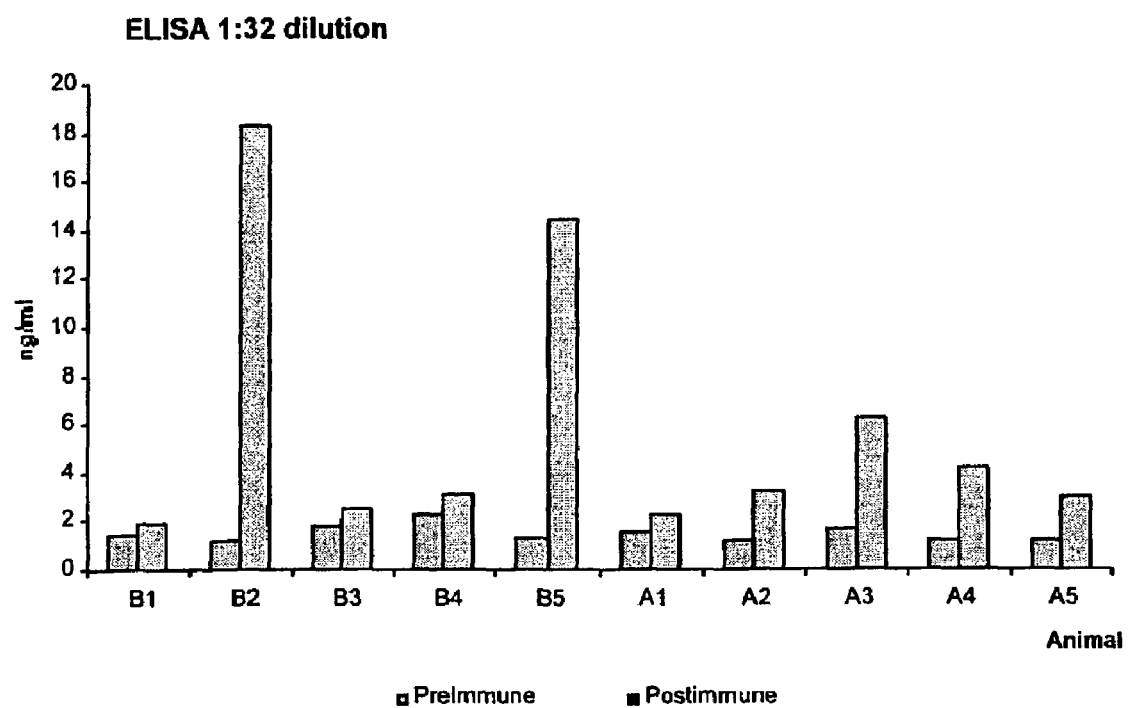
FIG. 4. DNA encoding amyloid beta induces protective anti-amyloid beta antibody titers. Mice were immunized with DNA encoding amyloid beta (Aβ) amino acids 1-42, and boosted 2 weeks later. Pre-treatment and four weeks after the second immunization, serum were obtained and ELISA analysis performed to determine anti-amyloid beta titers. The left bar for each animal represents pre-treatment titers, and the right bar represents post-treatment titers. B1-B4 were animals treated with phosphate buffered saline (containing 0.9 mM Ca++) with immunostimulatory CpG sequences. Animals B5, A1 and A2 were treated with DNA encoding amyloid beta in tris EDTA (containing no Ca++) with immunostimulatory CpG sequences. A3-A5 were treated with self vector only DNA (pTARGET) in tris EDTA (containing no Ca++) with immunostimulatory CpG sequences.

This self-vector comprising DNA encoding the self-peptide Aβ was administered to mice by intramuscluar injection. Forty-eight hours prior to administration of the self-vector, 50 μl of 0.25% bupivicane was injected by intramuscular injection into each of the two quadriceps muscles. Self-vector comprising DNA encoding Aβ, the self-peptide was purified using standard techniques, including an endotoxin removal step. The DNA was resuspended and stored in endotoxin-free, pyrogen-free water. Prior to injection the self-vector comprising the DNA encoding Aβ, the self-peptide was formulated at a final concentration of 1 mg/ml in PBS. Fifty microliters of this DNA formulation was then administered by intramuscular injection into each of the two quadriceps muscles. Additionally, immunostimulatory CpG oligonucleotides were administered at a dose of 10 μg per animal intramuscularly. A second boost of bupivicane and DNA with CpG oligos was given two weeks after the initial immunizaiton. Sera was then drawn from mice 4 to 6 weeks after the initial DNA was administered in order to be tested for the presence of antibodies against the Aβ peptide. Antibody levels were measured by standard ELISA techniques (FIG. 4). Normal mice treated according to the above protocol develop significant antibody titers against the Aβ peptide.

Experiments using this protocol with the self-vector comprising DNA encoding Aβ are conducted in human Aβ transgenic mice. The transgenic mice are constructed by injecting single cell embryos with the human Aβ gene construct and then reintroducing these embryos into appropriate host strains of mice (Games et al., Nature 373:523-527, 1995); (Hsiao et al., Science 274:99-102, 1996). The resultant progeny are then screened for the presence of the Aβ gene construct within the genome. These mice display characteristic pathophysiologic and behavioral abnormalities that mimic human Alzheimer's disease. Both young pre-symptomatic mice and older symptomatic mice are treated with the self-vector comprising DNA encoding construct. The parameters for efficacy that are measured include improvement on cognitive behavioral testing and in histopathology. The young pre-symptomatic mice will be examined 12-18 months after the DNA treatment to determine the incidence of cognitive deficits and amyloid plaques on histology. The older symptomatic mice will be examined 3-6 months after the DNA treatment for improvement in the absolute clinical score on behavioral testing and for reduction in gross numbers of amyloid plaques on histology.

EXAMPLE 18

Polynucleotide Therapy Comprising Administration of DNA Encoding Amyloid β Protein for the Prevention and Treatment of Human Alzheimer's Disease A self-vector comprising DNA encoding the human amyloid β Aβ polypeptide is constructed. As described previously, the cassette has transcriptional and translational regulatory sequences for expression of the DNA in the recipient cells. Treated subjects include human patients with a high clinical likelihood of developing Alzheimer's disease, or with evidence for early cognitive impairment or other evidence for future development of Alzheimer's, or for patients with clinically definite Alzheimer's disease. This self-vector comprising DNA encoding the self-peptide Aβ is administered to by intramuscluar injection. Self-vector comprising DNA encoding Aβ, the self-peptide is purified using standard techniques, including an endotoxin removal step. The DNA is resuspended and stored in endotoxin-free, pyrogen-free water. Prior to injection the self-vector comprising the DNA encoding Aβ, the self-peptide is formulated at a final concentration of 1 mg/ml in PBS. One milliliter of this DNA formulation is then administered by intramuscular injection into the quadriceps muscle. Additionally, the self-vector construct can contain multimers of the Aβ encoding DNA linked by an intervening sequence, such that a multimeric Aβ polypeptide is encoded. In this way, not only is the primary peptide structure targeted as an immunogen, but the secondary structure (such as a β pleated sheet formed by multiple Aβ peptides) is also targeted as an immunogen. Boosters of self polynucleotide are given two to four weeks after the initial immunization, and repeated until sufficient anti-amyloid beta antibodies, levels that correlate with reduction of clinical disease, are achieved. Every 3-4 months sera is then drawn from humans to monitor the presence and titers of antibodies against the Aβ. This is measured by standard ELISA techniques. Additional A β self polynucleotide boosters are delivered to maintain therapeutic titers of anti-Aβ antibodies. Efficacy in humans is demonstrated by slowing of the progression of cognitive deficits and/or improvement in cognitive function.

EXAMPLE 19

A Method for Treating Parkinson's Disease with DNA Therapy Encoding α-Synuclein

A DNA self-vector is constructed encoding the human α-synuclein polypeptide comprising the appropriate control and regulatory elements. The cassette, vector employed, and administration are similar to that described in Example 6. The production of antibodies against α-synuclein is measured. The DNA construct will then be administered to both young pre-symptomatic mice and older symptomatic mice transgenic for the human α-synuclein gene. Several transgenic mouse models for the alpha-synuclein gene are now available. One of these transgenic lines develops intracellular inclusions and has motor impairments (Masliah et al., Science 287:1265-1269, 2000). These treated animals are then assessed for improvement in both clinical and pathophysiologic parameters of disease. The young pre-symptomatic mice will be examined 9-12 months after the DNA self-vector treatment to determine the incidence of motor deficits and intracellular inclusions on histology. The older symptomatic mice will be examined 3-6 months after the DNA self-vector treatment for improvement in the absolute clinical score on motor testing and for reduction in gross numbers of intracellular inclusions on histology.

EXAMPLE 20

A Method for Treating Huntington's Disease with DNA Therapy Encoding Huntington Protein A DNA self-vector is constructed encoding various lengths of the CAG trinucleotide repeat and is administered by route and regimen as described in Example 6. The production of antibodies against Huntington protein is measured. The DNA construct is administered to both young pre-symptomatic mice and older symptomatic mice transgenic for the mutant human huntingtin gene with an increased number of CAG trinucleotide repeats. A mouse transgenic for the mutant huntingtin gene posseses clinical and pathologic features nearly identical to the human disease. These mice develop intracellular inclusions consisting of mutant huntingtin and have motor abnormalities as in the human disease. A recent study demonstrated that if the expression of the mutant gene was terminated the disease histopathology was reversed and the clinical symptoms improved (Yamamoto et al., Cell 101:57-66, 2000). The DNA treated animals are assessed for improvement in both clinical and pathophysiologic parameters of disease. The young pre-symptomatic mice are examined 9-12 months after the DNA treatment to determine the incidence of motor deficits and intranuclear huntingtin inclusions on histology. The older symptomatic mice are examined 3-6 months after the DNA treatment for improvement in the absolute clinical score on motor testing and for reduction in gross numbers of intranuclear inclusions on histology.

EXAMPLE 21

A Method for Preventing and Treating Huntington's Disease with DNA Therapy Encoding Huntingtin Protein Humans with established Huntington's disease, or who have tested positive for the mutant human Huntingtin gene and are thus susceptible to develop Huntington's disease, can be treated with self polynucleotide encoding Huntingtin protein to prevent development of or to treat established Huntington's disease. A DNA self-vector is constructed encoding various lengths of the CAG trinucleotide repeat and is administered intramuscularly, followed by a boost 4-8 weeks later. It can be administered with immunostimmulatory DNA sequences and/or fused to C3d to increase the efficacy of the self-polynucleotide therapy. The production of antibodies against Huntingtin protein is measured, and additional DNA self-vector boosts are delivered to achieve anti-Huntingtin antibody titers that correlate with a therapeutic level. Efficacy is monitored based on clinical improvement in the neurologic features of Huntington's disease.

EXAMPLE 22

A Method for Treating Prion Disease with DNA Therapy Encoding Prion Self-Protein A DNA self-vector is constructed encoding the prion protein domains involved in beta sheet formation. The plasmid vector is administered as described in Example 6. The production of antibodies against the prion protein is measured. The DNA construct is administered to both young pre-symptomatic mice and older symptomatic mice in a transgenic model for prion disease. These mice are transgenic for a prion gene containing mutation which confers on these mice a slowly progressive neurodegenerative disorder that mimics the behavioral and pathophysiologic abnormalities of human prion disease (Chiesa et al., Neuron 21:1339-1351, 1998). The young pre-symptomatic mice are examined 9-12 months after the DNA treatment to determine the incidence of cognitive and motor deficits along with abnormal histology. The older symptomatic mice are examined 3-6 months after the DNA treatment for improvement in the absolute clinical score on cognitive and motor testing and for reduction in severity of abnormalities on histological examination.

EXAMPLE 23

A Method for Treating Obesity with DNA Encoding Self-Proteins Involved in Regulating Feeding Behavior, Adipogenesis, and/or Metabolism DNA self-vector comprising DNA encoding one or more of the self-protein(s), -polypeptide(s) or -peptide(s) selected from the group consisting of syndecan-3, perilipin, orexin, galanin, and glucogon-like peptide receptor, and other proteins as would be known to one of ordinary skill in the art using the teaching of this invention, involved in regulating feeding behavior, adipogenesis, and/or metabolism is constructed after obtaining the DNA encoding the self-proteins, -polypeptide, or -peptide as described previously using PCR. These DNA self-vectors(s) are administered to mice by intramuscluar injection. Forty-eight hours prior to administration of the DNA, 50 µl of 0.25% bupivicane is injected by intramuscular injection into each of the two quadriceps muscles. Plasmid DNA is purified using standard techniques, including an endotoxin removal step. The DNA self-vector is resuspended and stored in endotoxin-free, pyrogen-free water. Prior to injection the DNA self-vector is formulated at a final concentration of 1 mg/ml in PBS with 0.9 mM calcium. Fifty microliters of this DNA self-vector formulation is then administered by intramuscular injection into each of the two quadriceps muscles. In one embodiment the DNA self-vector is administered without an adjuvant, in another embodiment the DNA is administered with immunostimulatory CpG oligonucleotides are administered at a dose of 10 µg per animal intramuscularly or another agent. A second boost of bupivicane and DNA with CpG oligos is given two weeks after the initial immunization. Sera is then drawn from mice 4 to 6 weeks after the initial DNA was administered in order to be tested for the presence of antibodies against the encoded self protein. This is measured by standard ELISA techniques. This DNA self-vecor therapy is evaluated individually and in combination for its ability to reduce weight gain and promote weight loss in C57BL/6 mice fed high-fat diets that promote obesity (55% fat from calories [catalogue # 93075, Harlan Taklad, Madison, Wis.], in contrast to regular mouse chow with only 9% calories from fat).

EXAMPLE 24

A Method for Preventing Osteoarthritis with DNA Encoding Self-Protein(s) Involved in Regulating Cartilage Remodeling, Degradation, and Growth DNA encoding cathepsins, plasmin, collagenases, and metaloproteinases is isolated using PCR and cloned into a plasmid DNA expression vector similar to that described in Example 1. Del1 mice carrying 6 copies of the pro alpha1(II) collagen transgene with a short deletion mutation get osteoarthritis that appears at 3 months of age (Salminen et al., Arthritis Rheum 44:947-955, 2001); (Rintala et al., J Anat 190:201-208, 1997). Starting at 4 weeks of age these mice receive every-other-week injections of DNA self-vector encoding cathepsins, plasmin, collagenases and metaloproeinases individually or in combinations. Groups of mice are sacrificed at monthly intervals to perform histologic analysis of their knee cartilage.

EXAMPLE 25

A Method for Preventing Spinal Cord Injury with DNA Therapy Encoding the Self-Protein Nogo-A A target of therapy of spinal cord injury is a protein designated Nogo-A. Antibodies against Nogo-A have been shown to promote axonal regrowth in animal models of spinal cord injury. Self-vectors are constructed comprising DNA encoding the mouse, rat, and human sequence of two regions of the Nogo-A molecule that have been identified as potentially responsible for the inhibitory capacity of this molecule, namely an extracellular 66 amino acid loop and an intracytoplasmic C-terminal region termed AS472. The DNA is cloned into an appropriate DNA expression vector forming a self-vector of this invention and administered to produce a neutralizing antibody response against these regions of Nogo-A. To test the neutralizing effect of the generated antibodies; an in vitro assay is used to assess 3T3 fibroblast spreading, dorsal root ganglia (chick E12 DRG cultures) neurite outgrowth, and mouse P4 cerebellar granule neuron sprouting, in the presence of the recombinant Nogo proteins. The DNA constructs are tested in proven animal models for spinal cord injury. These models include the rat spinal cord crush and spinal cord transection models. Three different experimental treatment protocols are followed: namely, preventive DNA self-vector treatment (DNA self-vector administration followed by spinal cord lesion), acute treatment (DNA self-vector administration immediately after lesion) and chronic treatment (prolonged DNA self-vector administration to assess the potential for growth restoration in chronically injured neurons). Axonal recovery is measured through the use of standard histological techniques and immunohistochemistry for axonal markers. Motor axon regeneration is tested using anterograde tracing with biotin dextran amine for corticospinal tract, and immunohistochemistry for serotoninergic (raphespinal) and noradrenergic (coerulospinal) neurons. Functional recovery is assessed using standardized methods for clinical evaluation. Motor recovery tests such as the 21-point BBB locomotion scale, grid walk, narrow-beam crossing and climbing test is used (Ramon-Cueto et al., Neuron 25:425-435, 2000); (Merkler et al., J Neurosci 21:3665-3673, 2001). Electromyographic recordings of leg muscles are used in the evaluation of hindlimb motor recovery. Sensitivity is tested using response to light touch (contact placing), joint bending (proprioception) and tail flick (pain) tests.

EXAMPLE 26

A Method for Preventing and Treating Graft Versus Host Disease with DNA Therapy Encoding Major Histocompatibility Self-Protein(s) and Additional Self Proteins Graft versus host disease (GVHD) causes significant morbidity and mortality in patients receiving allogeneic hematopoietic cell transplants. GVHD is mediated by graft immune cells attacking self-proteins expressed by the recipient's cells. Using bone marrow cell transfer from Balb/c ($H-2^d$) to Balb/k ($H-2^k$) mice, DNA encoding the $H-2^d$ class I and Class II MHC self-protein(s) is shown to reduce GVHD. For hematopoietic stem cell transplants, bone marrow is obtained from the femurs of Balb/c mice, and cells positively selected for expression of c-Kit using the MiniMACS/MidiMACS separation system (Miltenyi Biotech, Aburn, Calif.). The c-Kit selected cells were injected into the tail veins of Balb/k recipients 24 hours following split-dose lethal irradiation of 800 cGy delivered in 2 fractions. Recipient mice pre-treated with 3 weekly doses of self-vector comprising DNA encoding $H-2^d$ class I and II MHC self-protein(s) to reduce GVHD. GVHD is monitored based on measurement of liver enzymes (aspartate amino transferase, alanine aminotransferase, alkaline phosphatase, bilirubin) and histologic analysis of organs commonly affected in GVHD (skin, gastrointestinal tract, liver, etc) for evidence of inflammation and necrosis (acute GVHD) as well as chronic inflammation, fibrosis and atrophy (chronic GVHD). Mixed lymphocyte cultures is performed to assess the extent of tolerance induction, based on reduced responses of graft lymphocytes to irradiated host antigen presenting cells.

DNA self-vectors encoding human MHC class I and II alleles are prepared as described previously. Hematopoietic stem cell transplant recipients are tested to determine the specific MHC class I and II alleles they express. Using DNA therapy encoding the recipient's class I and II alleles the graft cells to be transplanted are pretreated in vitro to prevent GVHD. DNA encoding these self-MHC molecules are used to treat post-transplant recipients with ongoing GVHD. DNA therapy may reduce GVHD-associated post-transplant mortality and to reduce clinical manifestations of GVHD including skin rashes, gastrointestinal involvement, and involvement of other organs including the liver (monitored by examination of serum for markers of liver injury, including aspartate amino transferase, alanine aminotransferase, alkaline phosphatase, bilirubin).

EXAMPLE 27

Figure 5:
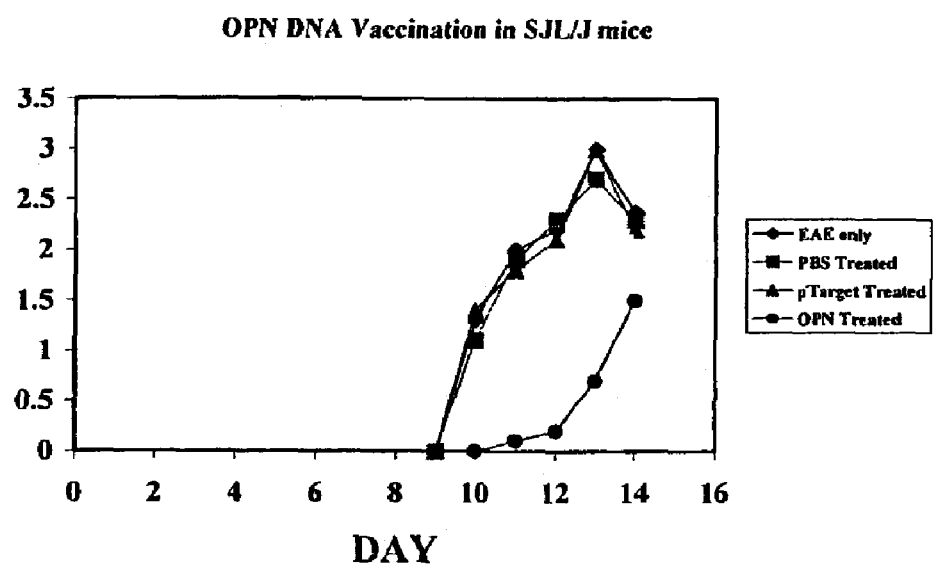
FIG. 5. Treatment with DNA encoding the self-protein osteopontin reduces the incidence and severity of EAE. C57B6 mice were treated with DNA encoding osteopontin prior to induction of EAE with MOGp35-55 in complete Freund's adjuvant. Clinical scores for EAE are indicated on the vertical axis.

A Method to Treat Multiple Sclerosis and Other Autoimmune Diseases with DNA Encoding Osteopontin Osteopontin is a pleiotrophic molecule recently identified to play pathogenic roles in multiple sclerosis and its animal model, EAE. Osteopontin may also play central roles in inflammatory arthritis and other human autoimmune diseases. Treatment of mice with DNA encoding the self protein osteopontin induces an anti-osteopontin immunoglobulin response in the host that inhibits the detrimental impact of osteopontin in perpetuating the disease. Self-vector DNA encoding osteopontin was generated by cloning DNA encoding osteopontin into the pCDNA3 mammalian expression vector. pCDNA3 contains the CMV promoter and SV-40 large T antigen poly adenylation signal. This osteopontin-encoding self-vector was produced in E. coli and endotoxin-free DNA purified using the Qiagen Endo-free Mega-prep kits (Qiagen, Valencia, Calif.). Mice are injected in the quadricep with 0.1 ml of 0.25% bupivicaine-HCL (Sigma, St. Louis, Mo.) in PBS (0.05 ml per quadricep). Two days following, mice are injected with 0.05 ml of each self-plasmid DNA at 1.0 mg/ml in phosphate buffered saline with 0.9 mM calcium in each quadricep. The plasmid DNA is injected two more times at 2 to 4 week intervals. The efficacy of osteopontin-encoding self-vector induction of anti-osteopontin antibodies can be enhanced by co-delivery of CpG immunostimulatory oligonucleotides (described below) and/or treatment with DNA encoding osteopontin fused to one or more C3d components (described below). Enzyme-linked immunosorbent assays were used to monitor levels of anti-osteopontin antibodies, with induction of anti-osteopontin antibodies representing efficacy of the therapy. Mice were subsequently challenged to develop EAE with a myelin peptide (typically PLPp139-151) in complete Freund's adjuvant, and mice pre-treated with self-vector encoding osteoponin have a reduced incidence and severity of EAE as demonstrated in FIG. 5. Alternatively, strains of mice susceptible to chronic relapsing EAE (for example, SJL mice) can be induced to develop EAE (for example, with PLPp139-151 in complete Freund's adjuvant) and osteopontin-self-vector therapy initiated on bi-weekly intervals in mice with established EAE to induce antibodies against osteopontin to treat the disease. Efficacy is measured based on a reduction in the overall disease severity and number of new episodes of clinical paralysis using standard scoring systems (described above).

In humans with multiple sclerosis osteopontin-self-vector therapy is initiated following diagnosis. Efficacy is monitored based on induction of anti-osteopontin antibodies in the patient with multiple sclerosis, as measured by ELISA analysis. Efficacy is further demonstrated based on reduction in the number and size of lesions on brain MRI scanning, reduction of the number of disease relapses (episodes of clinical paralysis), and slowing of progression to disability.

EXAMPLE 28

A Method for Prevention and Treatment of Tissue Transplant Rejection with DNA Encoding Self Tissue Transplant Proteins Currently one of the greatest limitations to transplantation of tissues and organs (kidney, liver, heart, lung, blood transfusions, pancreatic, islet cell, hematopoietic cell, etc) is immune rejection of the tissue transplant by the recipient. Immune rejection is mediated by the recipients' immune system which recognizes allelic variations in the tissue transplant proteins. These tissue transplants become self, based on these allelic variations of the relevant self-proteins being encoded in the genome of the tissue transplant. Transplantation of the tissue and its genome into a recipient makes these proteins self-proteins for the recipient. Tissue transplant rejection is mediated by recipient immune responses against the MHC class I and II proteins in the tissue transplant, and against other histocompatibility and additional antigens with allelic variation in the tissue transplant as compared to the recipient.

Using tissue transplants between Balb/c ($H-2^d$) and Balb/k ($H-2^k$) mice, DNA self-vectors encoding the $H-2^d$ class I and Class II MHC molecules as administered to the transplant recipient reduces rejection of solid organ tissue transplants. Using standard protocols, hearts are transplanted from $H-2^d$ mice into ectopic abdominal locations in $H-2^k$ mice (ectopic transplantation enables close monitoring of the transplanted heart by simple palpation). Recipient mice are pre-treated (prior to transplant) with 3 weekly doses of pTARGET containing DNA encoding $H-2^d$ class I and II MHC molecules, and/or post-transplant with weekly or bi-weekly or monthly treatments with DNA encoding $H-2^d$ class I or II molecules. Pre-treatment and/or post-transplant treatment with DNA self-vector encoding the self-MHC and other self-proteins of the tissue transplant prolongs graft survival in recipient mice, as monitored by palpation of the transplanted heart.

DNA self-vectors encoding human MHC class I and II alleles are generated as described previously. Transplant donors and recipients are tested to determine the specific MHC class I and II alleles they express. Using DNA self-vector therapy comprising administration of self-vectors encoding the tissue transplant donor's class I and II MHC alleles, recipients of transplanted organs are pretreated to prevent tissue transplant rejection. DNA encoding self-MHC molecules are administered to treat tissue-transplant rejection in post-transplant recipients. DNA therapy comprising administration of self-vector reduces immune organ transplant rejection and prolong survival of the tissue transplants.

EXAMPLE 29

A Method for Prevention or Treatment of Immune-Mediated Encephalomyelitis Following Small Pox Vaccination One of the major limitations of small pox vaccination is the complication of post-vaccinial acute disseminated encephalomyelitis that occurs in approximately 1:1000 patients receiving the currently available small pox vaccine. This post-vaccinial acute disseminated encephalomyelitis is mediated by vaccine-induced autoimmune responses directed against myelin and other central nervous system proteins.

Polynucleotide therapy of this invention to treat human small pox vaccination-induced immune-mediated encephalomyelitis is carried out as follows. DNA sequences encoding one or more of the human myelin self-proteins are cloned into pTARGET or another suitable DNA self-vector. DNA encoding those myelin self-proteins targeted by such autoimmune responses include myelin basic protein, proteolipid protein, myelin associated glycoprotein, cyclic nucleotide phosphodiesterase, myelin-associated glycoprotein, myelin-associated oligodendrocytic basic protein and alpha-B-crystalin. The DNA is purified free of bacterial endotoxin for delivery to humans as a therapeutic agent as described previously. The DNA self-vector therapy is delivered monthly or bimonthly for 6-12 months, and then every 3-12 months as a maintenance dose. Alternative treatment regimens may be developed and may range from daily, to weekly, to every other month. Human patients treated with the described DNA therapy are monitored for disease activity based on the progression of clinical symptoms (including motor power, sensation, and cognitive measures) and MRI monitoring for number and extent of central nervous system lesions.

EXAMPLE 30

A Method for Use of Immunostimmulatory DNA Sequences to Increase Anti-Self-Polypeptide Immunoglobulin Titers in Combination with Therapy with DNA Encoding a Self Polypeptide Treatment of mice with DNA encoding self-polypeptides alone generally induces weak immune responses with low antibody titers against the encoded self-polypeptides because of the barriers imposed by tolerance to self. In order to induce high antibody titers against self-polypeptides to treat diseases caused or promoted by pathogenic self-proteins, adjuvants are added to the self-vector DNA to boost its immunogenic potential. One such adjuvant is nucleotide sequences that are known to be immunostimulatory. It has been reported that so-called CpG sequences are able to boost the immune response against an antigen encoded within DNA (Krieg et al., Nature 374:546-549, 1995; Klinman et al. PNAS (USA) 93:2879-2883, 1996; Sato et al. J Rheumatol. 26: 294-301, 1999). CpG sequences are incorporated into the DNA self-vector formulations either endogenously by increasing the number of CpG sequences present within the plasmid or by adding exogenous CpG containing oligonucleotides. The CpG sequences in either case are of the motif purine-purine-C-G-pyrimidine-pyrimidine. Multiple endogenous CpG sequences are incorporated within non-coding regions of the plasmid using site-specific mutagenesis. Exogenous CpG oligonucleotides contain anywhere from one to ten CpG sequences and are from 10 to 100 nucleotides in length. Additionally, the backbone of these oligonucleotides is modified in order to reduce the chance of degradation, for example with a phosphorothioated backbone. Immunostimulatory CpG oligonucleotides are administered at a dose of 10 to 100 µg per animal intramuscularly. This strategy is applied to any polynucleotide encoding a self-polypeptide where an increase in antibody titers is desired.

As described in Example 12, exogenous CpG oligonucleotides are used to boost the antibody response against the self-protein amyloid β (Aβ) as administered by DNA. The self-vector comprising DNA encoding the self-peptide Aβ was administered to mice by intramuscluar injection. Forty-eight hours prior to administration of the self-vector, 50 µl of 0.25% bupivicane was injected by intramuscular injection into each of the two quadriceps muscles. Alternatively, DNA therapy comprises administration of self-vector effective with no pre-conditioning regimen. Self-vector comprising DNA encoding Aβ was purified using standard techniques, including an endotoxin removal step. The DNA was resuspended and stored in endotoxin-free, pyrogen-free water. Prior to injection the self-vector comprising the DNA encoding Aβ was formulated at a final concentration of 1 mg/ml in PBS. Fifty microliters of this DNA formulation was then administered by intramuscular injection into each of the two quadriceps muscles. Additionally, immunostimulatory CpG oligonucleotides were administered at a dose of 10 µg per animal intramuscularly. A second boost of bupivicane and DNA self-vector with CpG oligos was given two weeks after the initial immunization. Sera were then drawn from mice 4 to 6 weeks after the initial DNA was administered in order to test for the presence of antibodies against the Aβ peptide. This was measured by standard ELISA techniques. Normal mice treated according to this protocol develop significant antibody titers against the Aβ peptide. Titers were significantly increased when CpG oligonucleotides were used as an adjuvant.

EXAMPLE 31

Polynucleotide Therapy Comprising Administration of DNA Encoding a Library of Self-Proteins Expressed in a Organ or Tissue Targeted by the Autoimmune Response Another strategy for the treatment of autoimmunity is to administer DNA encoding many or all of the self-proteins present within a tissue or organ under immune attack. cDNA expression libraries contain cDNA encoding many or the vast majority of the self-proteins expressed in a specific tissue, organ, or cell type. Such cDNA expression libraries are generated in the self-vector to enable expression of the polypeptides they encode upon administration to a host. Animals and humans with established multiple sclerosis are treated with self-vector encoding a library of cDNA expressed in oligodendrocytes in the brain. Animal and humans with rheumatoid arthritis are treated with self-vector encoding a library of cDNA expressed in synovial joints which are the target of the autoimmune response in rheumatoid arthritis. Animals and humans with autoimmune diabetes are treated with self-vector encoding a library of cDNA expressed in beta cells of the pancreas. Self-vector encoding cDNA expressed in the beta cells of the pancreas can also be utilized to prevent development of clinical diabetes in individuals identified to have a high risk of developing autoimmune diabetes. Alternatively, instead of using the whole cDNA library a large subset of the cDNA expression library encoded in self-vector can be used to treat autoimmunity.

EXAMPLE 32

Polynucleotide Therapy Comprising Administration of DNA Encoding One or More Self Protein(s), -Polypeptide(s), or -Peptide(s) and an Immunomodulatory Molecule for Various Diseases The methods described in Examples 1, 2 and 9 through 23 describing the idenfication of a self-protein(s), -polypeptide(s), -peptide(s), preparation of a self-vector and administration for treatment of various diseases. These methods in those examples are followed with the modification that the self-vector is administered with an immunomodulatory molecule, including for example, immunostimulatory sequences (ISS), C3d, IL-4, IL-10, and IL-13.

Polynucleotide therapy comprising DNA encoding one or more self-protein(s), -polypeptide(s), or -peptide(s) with additional immunomodulatory molecules for treating or preventing autoimmune diseases is set forth in Table 7.

Polynucleotide therapy comprising DNA encoding one or more self-protein(s), -polypeptide(s), or -peptide(s) with additional immunomodulatory molecules for treating or preventing neurodegenerative diseases is set forth in Table 8.

Polynucleotide therapy comprising DNA encoding one or more self-protein(s), -polypeptide(s), or -peptide(s) with additional immunomodulatory molecules for treating or preventing various diseases is set forth in Table 9.

TABLE 7

| Autoimmune Disease | Polynucleotide Therapy Comprising DNA Encoding Self-Protein(s), -Polypepetide(s) Or -Peptide(s) and Additional DNA Encoding Immunomodulatory Proteins, Peptides or Polypeptides |
|---|---|
| Multiple sclerosis | myelin basic protein (MBP) + IL-4; MBP + IL-10; MBP + IL-13; proteolipid protein (PLP) + IL-4; PLP + IL-10; PLP + IL-13; myelin associated glycoprotein (MAG); MAG + IL-4; MAG + IL-10; MAG + IL-13; cyclic nucleotide phosphodiesterase (CNPase) + IL-4; CNPase + IL-10; alpha-B-crystalin + IL-4; alpha-B-crystalin + IL-10; alpha-B-crystalin + IL-13; MBP + PLP + MAG + IL-4; MBP + PLP + MAG + IL-10; MBP + PLP + MAG + CNPase + alpha-B-crystalin + IL-4; oligodendrocyte cDNA library; oligodendrocyte cDNA library + IL-4; oligodendrocyte cDNA library + IL-10; oligo-dendrocyte cDNA library + IL-13 |
| Guillian Barre Syndrome | peripheral myelin protein I (P1) + IL-4; P1 + IL-10; P1 + IL-13; peripheral myelin protein II (P2) + IL-4; P2 + IL-10; P2 + IL-13; schwan cell cDNA library + IL-4; schwan cell cDNA library + IL-10; schwan cell cDNA library + IL-13 |
| Insulin Dependent Diabetes Mellitus | tyrosine phosphatase IA2 + IL-4; IA2 + IL-10; IA2 + IL-13; IA-2β; IA-2β + IL-4; IA2-b + IL-10; IA2-b + IL-13; glutamic acid decarboxylase (65 and 67 kDa forms) (GAD) + IL-4; GAD + IL-10; GAD + IL-13; carboxy-peptidase H (CH) + IL-4; CH + IL-10; CH + IL-13; insulin + IL-4 insulin + IL-10; insulin + IL-13; proinsulin + IL-4; proinsulin + IL-10; proinsulin + IL-13; heat shock proteins (HSPs) + IL-4; HSPs + IL-10; HSPs + IL-13; glima 38 + IL-4; islet cell antigen 69 KDa + IL-4; p52 + IL-4; ganglioside antigens + IL-4; islet cell glucose transporter GLUT-2 + IA2 + IL-4; GLUT2 + IA2 + IL-10; GLUT + IA2 + IL-13; GLUT + IA2 + GAD + IL-4; GLUT2 + IA2 + GAD + IL-10; GLUT2 + IA2 + GAD + IL-13; GLUT2 + IA2 + GAD + carboxy-peptidase H + proinsulin + HSPs + glima 38 + insulin; insulin + IA2 + GAD + IL-13; insulin + IA2 + GAD + carboxypeptidase H + proinsulin + HSPs + glima 38 + GLUT2 + IL-4; insulin + IA2 + GAD + IL-13; insulin + IA2 + GAD + carboxypeptidase H + proinsulin + HSPs + glima 38 + GLUT2 + IL-13; pancreatic β cell cDNA library + IL-4; pancreatic β cell cDNA library + IL-10; pancreatic β cell cDNA library + IL-13 |
| Rheumatoid Arthritis | Immunoglobulin (Ig) + IL-4; Ig + IL-10; Ig + IL-13; fibrin + IL-4; fibrin + IL-10; fibrin + IL-13; fibrin + peptidyl arginine deiminase (PAD) + IL-4; type II collagen (CII) + IL-4; CII + IL-10; CII + IL-13; BiP + IL-4; BiP + IL-10; BiP + IL-13; glucose-6-phosphate isomerase (G6PI) + IL-4; G6PI + IL-10; G6PI + IL-13; GP-39 + IL-4; GP-39 + IL-10; GP-39 + IL-13; fibrin + CII + BIP + G6PI + GP-39 + IL-4; fibrin + CII + BIP + G6PI + GP-39 + IL-10; fibrin + CII + BIP + G6PI + GP-39 + IL-13; chondrocyte cDNA library + IL-4; chondrocyte cDNA library + IL-10; chondrocyte cDNA library + IL-13; synovial cell cDNA library + IL-4; synovial cell cDNA library + IL-13; chondrocyte and synovial cell cDNA libraries + IL-4 |
| Autoimmune Uveitis | S-antigen (SAg) + IL-4; Sag + IL-10; SAg + IL-13; interphotoreceptor retinoid binding protein (IRBP) + IL-4; IRBP + IL-10; IRBP + IL-13; rhodopsin + IL-4; rhodopsin + IL-13; recoverin + IL-4; recoverini + IL-13; SAg + IRBP + IL-4; SAg + IRBP + IL-13; SAg + IRBP + rhodopsin + recoverin + IL-4; SAg + IRBP + rhodopsin + recoverin + IL-13; uveal cDNA library; uveal cDNA library + IL-4; uveal cDNA library + IL-10; uveal cDNA library + IL-13 |
| Primary Biliary Cirrhosis | pyruvate dehydrogenase complexes (2-oxoacid dehydrogenase complex proteins) (PDs) + IL-4; PDs + IL-10; PDs + IL-13; biliary tract cDNA library + IL-4 |
| Autoimmune Hepatitis | cytochrome P450 + IL-4; cytochrome P450 + IL-10; cytochrome P450 + IL-13; hepatocyte cDNA library + IL-4; hepatocyte cDNA library + IL-13 |
| Pemphigus vulgaris | Desmoglein-1 (DG-1) + IL-4; DG-1 + IL-13; desmoglein-3 (DG-3) + IL-4; DG-3 + IL-10; DG-3 + IL-13; DG-1 + DG-3; DG-1 + DG-3 + IL-4; keratinocyte cDNA library + IL-4 |
| Myasthenia Gravis | acetylcholine receptor (AChR) + IL-4; AChR + IL-10; AChR + IL-13 |
| Autoimmune gastritis Pernicious Anemia | H$^+$/K$^+$ ATPase + IL-4; intrinsic factor + IL-4 intrinsic factor + IL-4 |
| Polymyositis and dermatomyositis | histidyl tRNA synthetases + IL-4; histidyl tRNA synthetases + IL-13; myocyte cDNA library + IL-4; myocyte cDNA library + IL-13 |
| Autoimmune Thyroiditis | thyroglobulin + IL-4; thyroglobulin + IL-10; thyroglobulin + IL-13; thyroid peroxidase + IL-4; thyroid peroxidase + IL-13; thyroglobulin + thyroid peroxidase + IL-4; thyroid cDNA library + IL-4 |
| Graves's Disease | Thyroid-stimulating hormone receptor + IL-4 |
| Psoriasis | skin cDNA library + IL-4; skin cDNA library + IL-10; skin cDNA library + IL-13; |
| Vitiligo | tyrosinase + IL-4; tyrosinase + IL-13; tyrosinase-related protein-2 + IL-4 melanocyte cDNA library + IL-4; melanocyte cDNA library + IL-10; melanocyte cDNA library + IL-13; SOX9 + IL-4; SOX10 + IL-4 |
| Systemic Lupus Eryth. | nuclear antigens + IL-4; nuclear antigens + IL-13 |
| Celiac Disease | transglutaminase + IL-4; transglutaminase + IL-13 |

TABLE 8

| Neurodegenerative Disease | Polynucleotide Therapy Comprising DNA Encoding Self-Protein(s), -Polypepetide(s) Or -Peptide(s) and Additional DNA Encoding Immunomodulatory Proteins, Peptides or Polypeptides |
|---|---|
| Alzheimer's disease | amyloid β protein (Aβ) + immunostimmulatory sequences (ISS); Aβ + C3d; Aβ + ISS + C3d; tau + ISS; tau + C3d; tau + ISS + C3d |
| Parkinson's disease | α-synuclein + ISS; α-synuclein + C3d; α-synuclein + ISS + C3d |
| Huntington's disease | Huntingtin protein + ISS; Huntingtin protein + C3d; Huntingtin protein + ISS + C3d |
| Prion disease | Prion protein + ISS; Prion protein + C3d; Prion protein + ISS + C3d |

TABLE 9

| Disease | Polynucleotide Therapy Comprising DNA Encoding Self-Protein(s), -Polypepetide(s) Or -Peptide(s) And Additional DNA Encoding Immunomodulatory Proteins, Peptides, or Polypeptides |
|---|---|
| Obesity | syndecan-3 + ISS + C3d; perilipin + ISS + C3d; Orexin + ISS + C3d; Galanin + ISS + C3d; glucogon-like peptide receptor + ISS + C3d; syndecan-3 + ISS; perilipin + ISS; Orexin + ISS; Galanin + ISS; glucogon-like peptide receptor + ISS; syndecan-3 + C3d; perilipin + C3d; Orexin + C3d; Galanin + C3d; glucogon-like peptide receptor + C3d |
| Osteoarthritis | cathepsins + ISS; cathepsins + ISS + C3d; plasmin + ISS; plasmin + C3d; plasmin + ISS + C3d; collagenases + ISS; collagenases + C3d; collagenases + ISS + C3d; metalloproteinases + ISS; metalloproteinases + C3d; metalloproteinases + ISS + C3d |
| Spinal cord injury | Nogo-1 + ISS; Nogo-1 + C3d; Nogo-1 + ISS + C3d |
| Hypertension | angiotensin-converting enzyme (ACE) + ISS; ACE + C3d; ACE + ISS + C3d |
| Peptic ulcer disease | $H^+/K^+$ ATPase + ISS; $H^+/K^+$ ATPase + C3d; $H^+/K^+$ ATPase + ISS + C3d; gastin + ISS; gastrin + C3d; gastrin + ISS + C3d |
| Autoimmunity | osteoponin + ISS; osteoponin + C3d; osteoponin + ISS + C3d |
| Aging | superoxide dismutase + ISS + C3d; superoxide dismutase + ISS; superoxide dismutase + C3d |
| Depression | serotonin 5HT2 receptor + ISS; serotonin 5HT2 receptor + C3d; serotonin 5HT2 receptor + ISS + C3d; $\alpha_1$-adrenergic receptor + C3d; $\alpha_1$-adrenergic receptor + ISS + C3d; $\alpha_1$-adrenergic receptor + C3d + ISS |
| Gout | Xanthine oxidase + ISS; xanthine oxidase + C3d; xanthine oxidase + ISS + C3d |
| Migraine headaches | serotonin $5HT_{1B}$ + ISS; serotonin $5HT_{1B}$ + C3d; serotonin $5HT_{1B}$ + ISS + C3d; serotonin $5HT_{1D}$ + ISS; serotonin $5HT_{1D}$ + ISS + C3d |
| Hyperlipidemia | HMG CoA-reductase + ISS; HMG CoA-reductase + ISS + C3d; HMG CoA-reductase + C3d; apolipoprotein A + ISS; apolipoprotein A + C3d; apolipoprotein A + ISS + C3d; apolipoprotein B100 + ISS; apolipoprotein B100 + C3d; apolipoprotein B100 + ISS + C3d |
| Coronary artery disease | Angiotensin-converting enzyme (ACE) + ISS; ACE + C3d; ACE + ISS + C3d; apolipoprotein A + ISS; apolipoprotein A + C3d; apolipoprotein A + ISS + C3d; apolipoprotein B100 + ISS; apolipoprotein B100 + C3d; apolipoprotein B100 + ISS + C3d |

EXAMPLE 33

Polynucleotide Therapy Comprising Administration of DNA Encoding a Self-Protein, -Polypeptide, or -Peptide in Combination with DNA Encoding Co-Stimulatory Molecules, Molecules Capable of Modulating Co-Stimulation, or other Immune Modulating Molecules Studies examining co-stimulatory molecule blockade, including CD40/CD40L blockade (anti-CD40/CD40L antibodies) and B7-CD28 blockade (CTLA4-lg) have demonstrated significant efficacy in both animal models and human clinical trials for the treatment of autoimmunity, and may be used with DNA polynucleotide therapy of autoimmune disease. B7-1 and B7-2 bind CD28 and CTLA4 on the surface of T cells. Signals delivered through CD28 stimulate T cells, while engagement of CTLA4 is inhibitory. We generate and use DNA encoding a transmembrane form of CTLA4-specific immunoglobulin (Ig) in combination with DNA polynucleotide therapy to treat CIA. DNA encoding a membrane-bound form of CTLA4-specific Ig, a co-stimulatory molecule, is produced by grafting DNA encoding the Ig transmembrane region onto the CTLA4-specific Ig heavy chain cDNA (amplified from a hybridoma from ATCC producing CTLA4-specific Mab) using RT-PCR. DNA polynucleotide therapies of this invention in combination with DNA encoding co-stimulatory molecules or other immune modulating molecules, for example CD153 and Fas, may be used in the treatment of autoimmune disease.

EXAMPLE 34

Treatment of an Animal Model of Multiple Sclerosis Using IMS in Combination with DNA Encoding Multiple Self-Proteins A DNA polynucleotide therapy composed of full-length cDNAs encoding the four major components of myelin, MBP, MAG, MOG, and PLP treated relapsing disease in the EAE animal model when given after initial disease onset. Moreover, with the addition of DNA encoding IL-4 to the myelin DNA polynucleotide therapy, the efficacy of treatment is further enhanced by a decrease in relapse rate. However, despite the reduction in relapses, the overall disease severity is still comparable to the control group. Female SJL/J mice were immunized subcutaneously with 100 µg $PLP_{139-151}$ in PBS emulsified in CFA, consisting of IFA and 0.5 mg heat-inactivated *Mycobacterium tuberculosis*. Twelve days post immunization, at the time of disease onset, mice were injected in both quadriceps with a total of 0.1 ml 0.25% Bupivacaine-HCL in PBS. Two days later, selected mice were injected intramuscularly in both quadriceps with a DNA cocktail mixture containing 25 µg each of four separate pTARGET (Promega Corp. Wisconsin) plasmids encoding full-length murine PLP, MAG, MOG, and MBP plus 50 µg pTARGET plasmid encoding full-length murine IL-4 in a total volume of 0.2 ml. DNA injections were given at weekly intervals over the course of six weeks. At the same time as initial DNA vaccination, 50 µg IMS in a volume of 200 µl PBS was administered intraperitoneally alone or with DNA vaccination. IMS was given every other week over the course of six weeks.

Figure 6:
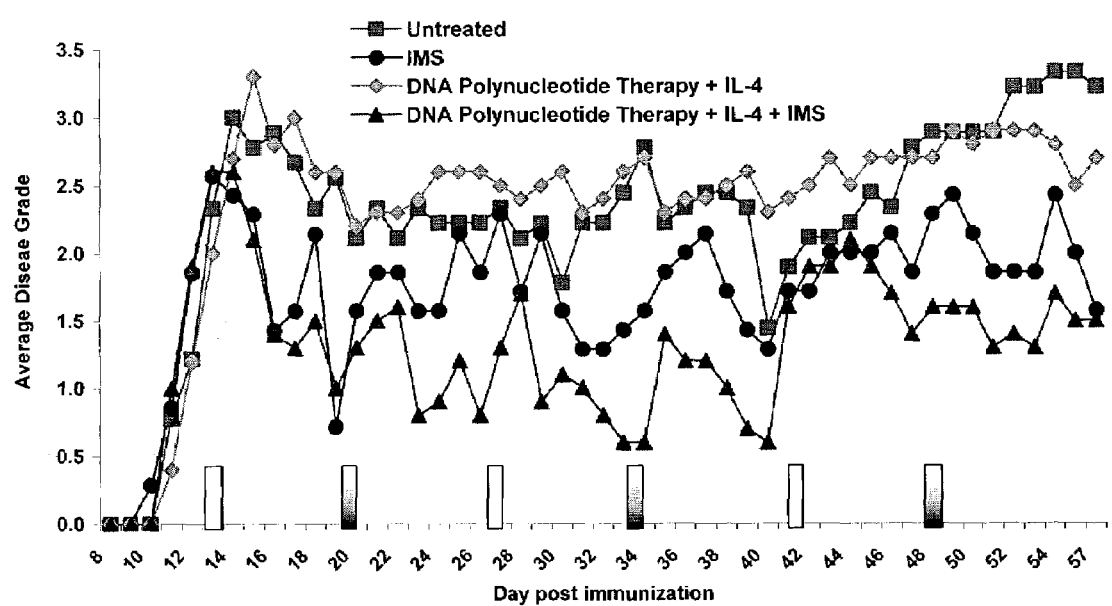
FIG. 6. Polynucleotide therapy with Inhibitory IMS suppresses $PLP_{139-151}$ mediated EAE. On day 0, seven-week old female SJL/J mice were immunized subcutaneously with 100 μg $PLP_{139-151}$ in PBS emulsified in CFA, consisting of IFA and 0.5 mg heat-inactivated *Mycobacterium tuberculosis*. Animals were clinically scored daily beginning on day 7. On day 12, mice were injected in both quadriceps with a total of 0.1 ml 0.25% Bupivacaine-HCL in PBS. Two days later, selected mice were injected intramuscularly in both quadriceps with DNA polynucleotide encoding full-length murine PLP, MAG, MOG, and MBP each on a separate pTARGET plasmid (25 μg of each) plus 50 μg pTARGET plasmid encoding full-length murine IL-4 in a total volume of 0.2 ml TE. DNA injections were given at weekly intervals for six weeks. At the same time as initial DNA treatment, 50 μg IMS in a volume of 200 μl PBS was administered intraperitoneally alone or with DNA polynucleotide treatment. IMS was given every other week for six weeks.

Compared to untreated mice and mice treated with DNA polynucleotide therapy plus a plasmid encoding IL-4, mice treated with IMS alone had an overall decreased mean disease severity throughout the entire disease course (FIG. 6). The reduction of overall mean disease severity was significantly more dramatic when mice were treated with DNA cocktail plus IL-4 in combination with IMS (FIG. 6).

Figure 7:
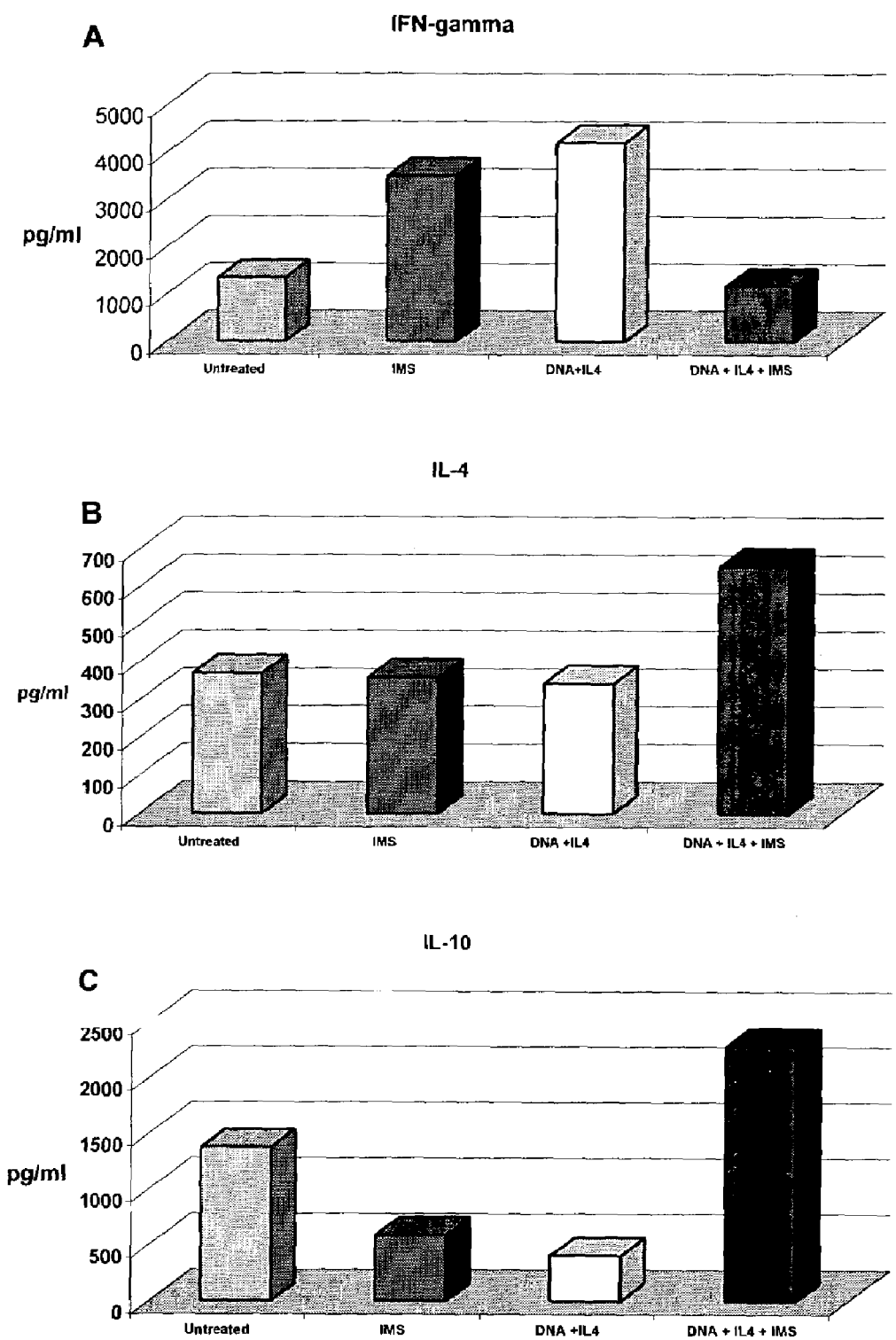
FIG. 7. Cytokine profile EAE treated groups. Fifty-seven days after EAE disease induction, mice were sacrificed and inguinal and axillary lymph nodes from each mouse were extracted and pooled according to the respective groups. Cells were isolated and stimulated with 10 μg/ml in $PLP_{139-151}$ in enriched RPMI media and 10% FCS. Three days later, cells were restimulated with human-rIL2 for three more days. Supernatants were collected and tested for cytokine profile by sandwich ELISA using standard murine (A) IFN-gamma, (B) IL-4 and (C) IL-10 ELISA kits from BD Pharmingen.

Fifty-seven days after EAE disease induction, mice were sacrificed and inguinal and axillary lymph nodes from the mice were extracted and pooled according to the respective groups. Cells were isolated and stimulated with 10 µg/ml in $PLP_{139-151}$ in enriched RPMI media and 10% FCS. Three days later, cells were restimulated with human-rIL2. Three days after restimulation, supernatants were collected and screened for IFN-γγ, IL-4 and IL-10 production by sandwich ELISA. The cytokine profile for untreated mice and mice treated with IMS alone or with DNA polynucleotide therapy plus IL-4 all had a Th1-bias of increased IFN-γ production (FIG. 7). The group treated with DNA polynucleotide therapy plus IL-4 in combination with IMS had a Th2-bias with increased IL-4 and IL-10 production.

EXAMPLE 35

Treatment of Insulin Dependent Diabetes Mellitus Using IMS in Combination with DNA Encoding the Self-Protein Insulin Nonobese diabetic (NOD) mice develop spontaneous autoimmune diabetes, and share many clinical, immunological, and histopathological features with human insulin-dependent diabetes mellitus (IDDM). The disease is characterized by inflammation of the pancreatic islets of Langerhans and destruction of the β cells, leading to hyperglycemia and overt diabetes. Both $CD4^+$ and $CD8^+$ T cells are required for disease development. Reactivity to several autoantigens, including insulin, IA-2, and glutamic acid decarboxylase, have been identified.

The efficacy of IMS treatment in combination with DNA encoding the self-protein insulin was initiated during invasive insulitis but before the complete onset of IDDM. NOD/Lt female mice were obtained at 7 weeks of age and housed in a restricted access room. Mice were tested weekly for elevated blood glucose levels (BGL) beginning at 10 weeks of age using the One Touch Ultra Blood Glucose Monitoring System. Treatment was initiated when the BGL was between 200 to 250 mg/dl. Mice were added sequentially to each group as they became available, beginning at the age of 15 weeks. Mice were injected in both quadriceps with a total of 0.2 ml 0.25% Bupivacaine-HCL in PBS. Two days later, mice were injected intramuscularly in both quadriceps with pVAX1 vector at 50 µg/dose or a DNA cocktail mixture containing 50 µg each of three separate pVAX1 plasmids encoding full-length murine Preproinsulin-1, Preproinsulin-2, and IL4 in a total volume of 0.2 ml PBS. Injections were given at weekly intervals for four weeks. At the same time as initial DNA vaccination, 50 µg IMS in a volume of 200 µl PBS was. administered intraperitoneally alone or with DNA vaccination. IMS was given at weekly intervals for four weeks.

Figure 8:
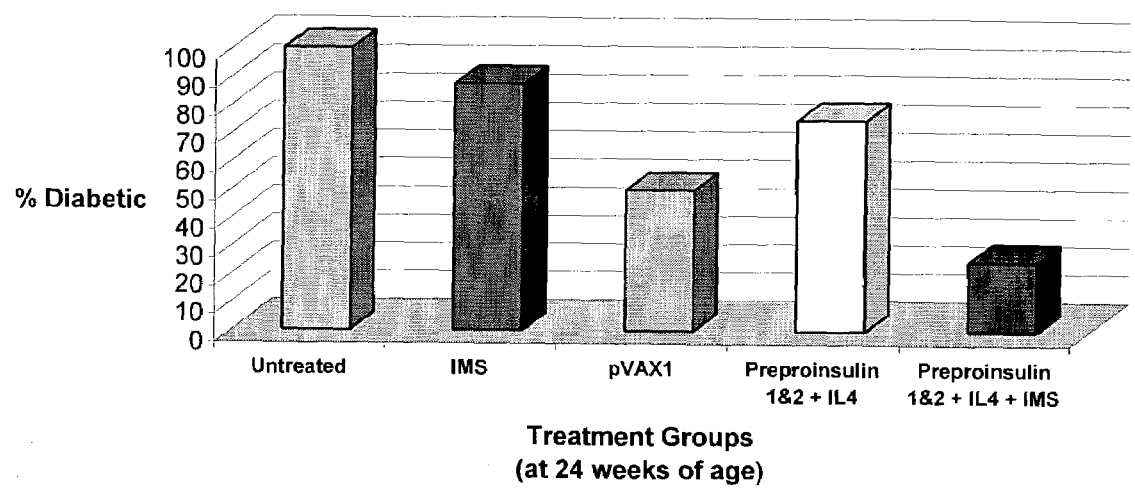
FIG. 8. DNA Polynucleotide Therapy and IMS treats diabetes in NOD mice. NOD/Lt female mice were obtained at 7 weeks of age and housed in a restricted access room. Mice were tested weekly for elevated blood glucose levels (BGL) beginning at 10 weeks of age using the One Touch Ultra Blood Glucose Monitoring System. Treatment was initiated when the BGL was between 200 to 250 mg/dl. Mice were added sequentially to each group as they became available, beginning at the age of 15 weeks. Mice were injected in both quadriceps with a total of 0.2 ml 0.25% Bupivacaine-HCL in PBS. Two days later, mice were injected intramuscularly in both quadriceps either with: 1) DNA polynucleotide encoding full-length murine preproinsulin-1 and preproinsulin-2 each on a separate pVAX1 vector at 50 μg/dose; or, 2) DNA polynucleotide encoding full-length murine preproinsulin-1 and preproinsulin-2 each on a separate pVAX1 vector at 50 μg/dose plus a pVAX1 plasmid encoding IL4 in a total volume of 0.2 ml PBS. Injections were given at weekly intervals for four weeks. At the same time as initial DNA treatment, 50 μg IMS in a volume of 200 μl PBS was administered intraperitoneally alone or with DNA polynucleotide treatment. IMS was given at weekly intervals for four weeks. Percent diabetic is defined as mice with a sustained BGL of over 250 mg/dl.

The percent diabetic is defined as mice with a sustained BGL of over 250 mg/dl. After four treatment injections, mice receiving IMS alone had a diabetes incidence of 87.5% by week 24 (FIG. 8). Mice receiving empty pVAX1 (Invitrogen, CA) plasmid had a diabetes incidence of 50%. Mice treated with a combination of DNA polynucleotide encoding autoantigens and the cytokine IL-4, together with immune modulatory sequences, developed only 20% diabetes incidence compared with 100% diabetes incidence in the untreated group by week 24 (FIG. 8). In this experiment, DNA plasmids were injected IM, while IMSs were injected IP, strongly suggesting that DNA plasmids (ISSs) and IMSs were targeting different cell populations. Moreover, NOD mice were not exposed to ISSs in this study. Taken together, this surprising and unexpected result demonstrates that IMSs effectively treat a naturally occurring autoimmune disease.

Numerous modifications may be made to the foregoing systems without departing from the basic teachings thereof. Although the present invention has been described in substantial detail with reference to one or more specific embodiments, those of skill in the art will recognize that changes may be made to the embodiments specifically disclosed in this application, yet these modifications and improvements are within the scope and spirit of the invention, as set forth in the claims which follow. All publications or patent documents cited in this specification are incorporated herein by reference as if each such publication or document was specifically and individually indicated to be incorporated herein by reference. Citation of the above publications or documents is not intended as an admission that any of the foregoing is pertinent prior art, nor does it constitute any admission as to the contents or date of these publications or documents.

---

What is claimed is:

1. A method of decreasing the severity of insulin dependent diabetes mellitus in a subject, the method comprising
   (a) administering intramuscularly a DNA plasmid vector comprising a polynucleotide encoding an autoantigen targeted in insulin dependent diabetes mellitus (IDDM), wherein the autoantigen comprises proinsulin; and
   (b) administering an immune modulatory sequence selected from the group consisting of 5'-Purine-Pyrimidine-[X]-[Y]-Pyrimidine-Pyrimidine-3' and 5'-Purine-Purine-[X]-[Y]-Pyrimidine-Pyrimidine-3' wherein X and Y are any naturally occurring or synthetic nucleotide, except that X and Y cannot be cytosine-guanine, whereby a decrease in the severity of insulin dependent diabetes mellitus in the subject is indicated by one or more measures selected from the group consisting of decreased hyperglycemia, increased plasma insulin, decreased glucosuria, decreased insulitis, decreased destruction of beta-cells, and decreased presence of autoantibodies.

2. The method of claim 1, wherein the immune modulatory sequence is incorporated into the DNA plasmid vector.

3. The method of claim 1, wherein the immune modulatory sequence is not incorporated into the DNA plasmid vector.

4. The method of claim 1, wherein the immune modulatory sequence is administered systemically.

5. The method of claim 1, wherein the immune modulatory sequence is administered intramuscularly.

6. The method of claim 1, further comprising administering a cytokine selected from the group consisting of IL-4, IL-10 and IL-13.

7. The method of claim 1, wherein the DNA plasmid vector comprises a polynucleotide encoding a second autoantigen targeted in IDDM.

8. The method of claim 7, wherein the second autoantigen is selected from the group consisting of insulin, insulin B chain, preproinsulin, proinsulin, glutamic acid decarboxylase (GAD) 65 kDa and 67 kDa forms, and tyrosine phosphatase IA2.

9. A method of decreasing hyperglycaemia in a subject predisposed to IDDM, the method comprising
   (a) administering intramuscularly a DNA plasmid vector comprising a polynucleotide encoding an autoantigen targeted in IDDM, wherein the autoantigen comprises proinsulin; and
   (b) administering an immune modulatory sequence selected from the group consisting of 5'-Purine-Pyrimidine-[X]-[Y]-Pyrimidine-Pyrimidine-3' and 5'-Purine-Purine-[X]-[Y]-Pyrimidine-Pyrimidine-3' wherein X and Y are any naturally occurring or synthetic nucleotide, except that X and Y cannot be cytosine-guanine, whereby the hyperglycaemia in the subject predisposed to IDDM is decreased.

10. The method of claim 9, wherein the subject has IDDM.

11. The method of claim 9, wherein the immune modulatory sequence is incorporated into the DNA plasmid vector.

12. The method of claim 9, wherein the immune modulatory sequence is not incorporated into the DNA plasmid vector.

13. The method of claim 9, wherein the immune modulatory sequence is administered systemically.

14. The method of claim 9, wherein the immune modulatory sequence is administered intramuscularly.

15. The method of claim 9, wherein the DNA plasmid vector comprises a polynucleotide encoding a second autoantigen targeted in IDDM.

16. The method of claim 15, wherein the second autoantigen is selected from the group consisting of insulin, insulin B chain, preproinsulin, proinsulin, glutamic acid decarboxylase (GAD) 65 kDa and 67 kDa forms, and tyrosine phosphatase IA2.

17. A method of reducing insulitis in a subject predisposed to IDDM, the method comprising
   (a) administering intramuscularly a DNA plasmid vector comprising a polynucleotide encoding an insulin autoantigen targeted in IDDM, wherein the autoantigen comprises proinsulin; and
   (b) administering an immune modulatory sequence selected from the group consisting of 5'-Purine-Pyrimidine-[X]-[Y]-Pyrimidine-Pyrimidine-3' and 5'-Purine-Purine-[X]-[Y]-Pyrimidine-Pyrimidine-3' wherein X and Y are any naturally occurring or synthetic nucleotide, except that X and Y cannot be cytosine-guanine, whereby the insulitis in the subject predisposed to IDDM is reduced.

18. The method of claim 17, wherein the subject has IDDM.

19. The method of claim 17, wherein the immune modulatory sequence is incorporated into the DNA plasmid vector.

20. The method of claim 17, wherein the immune modulatory sequence is not incorporated into the DNA plasmid vector.

21. The method of claim 17, wherein the immune modulatory sequence is administered systemically.

22. The method of claim 17, wherein the immune modulatory sequence is administered intramuscularly.

23. The method of claim 17, wherein the DNA plasmid vector comprises a polynucleotide encoding a second autoantigen targeted in IDDM.

24. The method of claim 23, wherein the second autoantigen is selected from the group consisting of insulin, insulin B chain, preproinsulin, proinsulin, glutamic acid decarboxylase (GAD) 65 kDa and 67 kDa forms, and tyrosine phosphatase IA2.

25. A method of inhibiting an auto immune response against an islet cell in a subject in need thereof, the method comprising
(a) administering intramuscularly a DNA plasmid vector comprising a polynucleotide encoding an insulin autoantigen targeted in IDDM, wherein the autoantigen comprises proinsulin; and
(b) administering an immune modulatory sequence selected from the group consisting of 5'-Purine-Pyrimidine-[X]-[Y]-Pyrimidine-Pyrimidine-3' and 5'-Purine-Purine-[X]-[Y]-Pyrimidine-Pyrimidine-3' wherein X and Y are any naturally occurring or synthetic nucleotide, except that X and Y cannot be cytosine-guanine, whereby the autoimmune response against the islet cell in the subject is inhibited.

26. The method of claim 25, wherein the subject has IDDM.

27. The method of claim 25, wherein the immune modulatory sequence is incorporated into the DNA plasmid vector.

28. The method of claim 23, wherein the immune modulatory sequence is not incorporated into the DNA plasmid vector.

29. The method of claim 25, wherein the immune modulatory sequence is administered systemically.

30. The method of claim 25, wherein the immune modulatory sequence is administered intramuscularly.

31. The method of claim 25, wherein the DNA plasmid vector comprises a polynucleotide encoding a second autoantigen targeted in IDDM.

32. The method of claim 31, wherein the second autoantigen is selected from the group consisting of insulin, insulin B chain, preproinsulin, proinsulin, glutamic acid decarboxylase (GAD) 65 kDa and 67 kDa forms, and tyrosine phosphatase IA2.

33. A method of delaying onset of IDDM in a subject in need thereof, the method comprising
(a) administering intramuscularly a DNA plasmid vector comprising a polynucleotide encoding an insulin autoantigen targeted in IDDM, wherein the autoantigen comprises proinsulin; and
(b) administering an immune modulatory sequence selected from the group consisting of 5'-Purine-Pyrimidine-[X]-[Y]-Pyrimidine-Pyrimidine-3' and 5'-Purine-Purine-[X]-[Y]-Pyrimidine-Pyrimidine-3' wherein X and Y are any naturally occurring or synthetic nucleotide, except that X and Y cannot be cytosine-guanine, whereby IDDM in the subject is delayed.

34. The method of claim 33, wherein the immune modulatory sequence is incorporated into the DNA plasmid vector.

35. The method of claim 33, wherein the immune modulatory sequence is not incorporated into the DNA plasmid vector.

36. The method of claim 33, wherein the immune modulatory sequence is administered systemically.

37. The method of claim 33, wherein the immune modulatory sequence is administered intramuscularly.

38. The method of claim 33, wherein the DNA plasmid vector comprises a polynucleotide encoding a second autoantigen targeted in IDDM.

39. The method of claim 38, wherein the second autoantigen is selected from the group consisting of insulin, insulin B chain, preproinsulin, proinsulin, glutamic acid decarboxylase (GAD) 65 kDa and 67 kDa forms, and tyrosine phosphatase IA2.

* * * * *

UNITED STATES PATENT AND TRADEMARK OFFICE
CERTIFICATE OF CORRECTION

| | |
|---|---|
| PATENT NO. | : 7,544,669 B2 |
| APPLICATION NO. | : 10/302098 |
| DATED | : June 9, 2009 |
| INVENTOR(S) | : Fontoura et al. |

It is certified that error appears in the above-identified patent and that said Letters Patent is hereby corrected as shown below:

In the Specification:

At Column 1, line 5 please insert the following:

-- This invention was made with Government support under contract NS018235 awarded by the National Institutes of Health. The Government has certain rights in this invention. --

Signed and Sealed this

Fourth Day of August, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,544,669 B2  
APPLICATION NO. : 10/302098  
DATED : June 9, 2009  
INVENTOR(S) : Fontoura et al.

Page 1 of 1

It is certified that error appears in the above-identified patent and that said Letters Patent is hereby corrected as shown below:

In the Specification:

At Column 1, line 5 please insert the following:

-- This invention was made with Government support under contract NS018235 and contract 1R43AI511-A101, both awarded by the National Institutes of Health. The Government has certain rights in this invention. --

This certificate supersedes the Certificate of Correction issued August 4, 2009.

Signed and Sealed this

Twenty-second Day of September, 2009

David J. Kappos  
*Director of the United States Patent and Trademark Office*

UNITED STATES PATENT AND TRADEMARK OFFICE
CERTIFICATE OF CORRECTION

PATENT NO. : 7,544,669 B2  
APPLICATION NO. : 10/302098  
DATED : June 9, 2009  
INVENTOR(S) : Fontoura et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1042 days.

Signed and Sealed this  
Tenth Day of July, 2012

David J. Kappos  
*Director of the United States Patent and Trademark Office*

SEQUENCE LISTING

```
<160> NUMBER OF SEQ ID NOS: 6

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence:synthetic
      oligonucleotide immune modulatory sequence (IMS)
      core hexamer with flanking sequences
<220> FEATURE:
<221> NAME/KEY: misc_feature
<222> LOCATION: (1)..(8)
<223> OTHER INFORMATION: flanking sequence
<220> FEATURE:
<221> NAME/KEY: modified_base
<222> LOCATION: (9)..(10)
<223> OTHER INFORMATION: n = any purine (e.g., g, a or i)
<220> FEATURE:
<221> NAME/KEY: modified_base
<222> LOCATION: (11)
<223> OTHER INFORMATION: n = any natural or synthetic nucleotide except
      c
<220> FEATURE:
<221> NAME/KEY: modified_base
<222> LOCATION: (12)
<223> OTHER INFORMATION: n = any natural or synthetic nucleotide except
      g
<220> FEATURE:
<221> NAME/KEY: modified_base
```

```
<222> LOCATION: (13)..(14)
<223> OTHER INFORMATION: n = any pyrimidine (e.g., t, c or u)
<220> FEATURE:
<221> NAME/KEY: misc_feature
<222> LOCATION: (15)..(22)
<223> OTHER INFORMATION: flanking sequence

<400> SEQUENCE: 1
tgactgtgnn nnnnagagat ga                                              22

<210> SEQ ID NO 2
<211> LENGTH: 63
<212> TYPE: DNA
<213> ORGANISM: Artificial Sequence
<220> FEATURE:
<223> OTHER INFORMATION: Description of Artificial Sequence:
      polynucleotide encoding proteolipid protein (PLP) self-protein
      epitope PLP (139-151)

<400> SEQUENCE: 2
ctcgagacca tgcattgttt gggaaaatgg ctaggacatc ccgacaagtt ttctagatag     60
cta                                                                   63

<210> SEQ ID NO 3
<211> LENGTH: 63
<212> TYPE: DNA
<213> ORGANISM: Artificial Sequence
<220> FEATURE:
<223> OTHER INFORMATION: Description of Artificial Sequence:
      polynucleotide encoding proteolipid protein (PLP) self-protein
      epitope PLP (139-151) L144/R147

<400> SEQUENCE: 3
ctcgagacca tgcattgttt gggaaaacta ctaggacgcc ccgacaagtt ttctagatag     60
cta                                                                   63

<210> SEQ ID NO 4
<211> LENGTH: 71
<212> TYPE: DNA
<213> ORGANISM: Artificial Sequence
<220> FEATURE:
<223> OTHER INFORMATION: Description of Artificial Sequence:DNA encoding
      insulin A (+) strand control

<400> SEQUENCE: 4
ccggaattcg ccatgtgcac gtcaatctgt tcactgtacc agctagagaa ctactgcaac     60
tagtctagag c                                                          71

<210> SEQ ID NO 5
<211> LENGTH: 71
<212> TYPE: DNA
<213> ORGANISM: Artificial Sequence
<220> FEATURE:
<223> OTHER INFORMATION: Description of Artificial Sequence:DNA encoding
      self-peptide insulin B (9-23), insulin B (+)
      strand

<400> SEQUENCE: 5
ccggaattcg ccatgagcca cctagtagaa gcactatacc tcgtatgcgg cgaacgaggt     60
tagtctagag c                                                          71

<210> SEQ ID NO 6
<211> LENGTH: 4
<212> TYPE: PRT
<213> ORGANISM: Artificial Sequence
```

```
-continued

<220> FEATURE:
<223> OTHER INFORMATION: Description of Artificial Sequence:myelin basic
      protein (MBP) 87-99 dominant T and B cell response
      target

<400> SEQUENCE: 6

His Phe Phe Lys
1
```